United States Patent
Muller

(10) Patent No.: US 7,282,154 B2
(45) Date of Patent: *Oct. 16, 2007

(54) RED BLOOD CELL PROCESSING SYSTEMS AND METHODS WHICH CONTROL RED BLOOD CELL HEMATOCRIT

(75) Inventor: Matthew Muller, Lindenhurst, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/255,356

(22) Filed: Oct. 21, 2005

(65) Prior Publication Data

US 2006/0060540 A1 Mar. 23, 2006

Related U.S. Application Data

(60) Division of application No. 10/280,109, filed on Oct. 24, 2002, now Pat. No. 7,011,761, which is a continuation-in-part of application No. 09/931,146, filed on Aug. 16, 2001, now Pat. No. 6,537,445, which is a continuation of application No. 09/389,912, filed on Sep. 3, 1999, now Pat. No. 6,284,142.

(51) Int. Cl.
*B01D 21/30* (2006.01)

(52) U.S. Cl. .............. 210/739; 210/96.1; 210/512.1; 210/787; 494/1; 494/37

(58) Field of Classification Search ............ 210/85, 210/94, 96.1, 512.1, 739, 745, 787, 789; 494/1–5, 10, 37, 43, 45; 356/39; 417/14, 417/18; 604/4.01, 5.01, 6.11, 6.07; 422/72, 422/82.05; 436/164, 177

See application file for complete search history.

(56) References Cited

U.S. PATENT DOCUMENTS

| | | | |
|---|---|---|---|
| 4,416,654 A | 11/1983 | Schoendorfer et al. | |
| 4,464,167 A | 8/1984 | Schoendorfer et al. | |
| 4,637,813 A | 1/1987 | DeVries | |
| 4,810,090 A | 3/1989 | Boucher et al. | |
| 4,834,890 A | 5/1989 | Brown et al. | |
| 4,952,127 A | 8/1990 | Schmeisser et al. | |
| 5,048,524 A | 9/1991 | Bailey | |
| 5,149,503 A | 9/1992 | Kohno et al. | |
| 5,316,667 A | 5/1994 | Brown et al. | |

(Continued)

FOREIGN PATENT DOCUMENTS

WO PCT/US03/33311 10/2003

*Primary Examiner*—Joseph Drodge
(74) *Attorney, Agent, or Firm*—Cook, Alex, McFarron, Manzo, Cummings & Mehler, Ltd.

(57) ABSTRACT

Processing systems and methods comprise a separation device that, in use, performs a separation process including separation of red blood cells from blood or a suspension containing red blood cells. The systems and methods include an outlet line coupled to the separation device to remove red blood cells from the separation device, at least in part, while the separation process occurs. A sensor associated with the outlet line senses hematocrit of red blood cells removed from the separation device and generates a sensed hematocrit output. A controller is coupled to the separation device to control removal of red blood cells from the separation device based, at least in part, upon the sensed hematocrit output.

23 Claims, 31 Drawing Sheets

U.S. PATENT DOCUMENTS

| | | |
|---|---|---|
| 5,348,533 A | 9/1994 | Papillon et al. |
| 5,348,539 A | 9/1994 | Herskowitz |
| 5,385,539 A | 1/1995 | Maynard |
| 5,478,479 A | 12/1995 | Herrig |
| 5,494,592 A | 2/1996 | Latham et al. |
| 5,573,678 A | 11/1996 | Brown et al. |
| 5,605,842 A | 2/1997 | Langley et al. |
| 5,607,579 A | 3/1997 | Latham et al. |
| 5,611,997 A | 3/1997 | Langley et al. |
| 5,681,273 A * | 10/1997 | Brown ............... 604/6.07 |
| 5,693,232 A | 12/1997 | Brown et al. |
| 5,704,888 A | 1/1998 | Hlavinka et al. |
| 5,704,889 A | 1/1998 | Hlavinka et al. |
| 5,712,798 A | 1/1998 | Langley et al. |
| 5,730,883 A | 3/1998 | Brown |
| 5,792,372 A | 8/1998 | Brown |
| 5,804,079 A | 9/1998 | Brown |
| 5,958,250 A | 9/1999 | Brown et al. |
| 5,961,842 A | 10/1999 | Min et al. |
| 5,980,760 A | 11/1999 | Min et al. |
| 6,027,657 A | 2/2000 | Min et al. |
| 6,064,474 A | 5/2000 | Lee et al. |
| 6,106,727 A | 8/2000 | Krasnoff et al. |
| 6,241,649 B1 | 6/2001 | Zanella et al. |
| 6,284,142 B1 | 9/2001 | Muller |
| 6,294,094 B1 | 9/2001 | Muller et al. |
| 6,322,488 B1 | 11/2001 | Westberg et al. |
| 6,348,156 B1 | 2/2002 | Vishnoi et al. |
| 6,384,156 B1 | 5/2002 | Bernier et al. |
| 6,419,822 B2 | 7/2002 | Muller et al. |

* cited by examiner

RED BLOOD CELL PROCESSING SYSTEMS AND METHODS WHICH CONTROL RED BLOOD CELL HEMATOCRIT

RELATED APPLICATIONS

This application is a divisional application of U.S. application Ser. No. 10/280,109, filed Oct. 24, 2002, now U.S. Pat. No. 7,011,761 which is a continuation-in-part application of U.S. application Ser. No. 09/931,146 filed Aug. 16, 2001, now issued as U.S. Pat. No. 6,537,445, which is a continuation application of U.S. patent application Ser. No. 09/389,912, filed Sep. 3, 1999, now U.S. Pat. No. 6,284,142. Each of these applications is hereby incorporated by reference herein.

FIELD OF THE INVENTION

This invention relates to systems and methods for processing and collecting blood, blood constituents, or other suspensions of cellular material.

BACKGROUND OF THE INVENTION

Today people routinely separate whole blood, usually by centrifugation, into its various therapeutic components, such as red blood cells, platelets, and plasma.

Conventional blood processing methods use durable centrifuge equipment in association with single use, sterile processing systems, typically made of plastic. The operator loads the disposable systems upon the centrifuge before processing and removes them afterwards.

Conventional blood centrifuges are of a size that does not permit easy transport between collection sites. Furthermore, loading and unloading operations can sometimes be time consuming and tedious.

In addition, a need exists for further improved systems and methods for collecting blood components in a way that lends itself to use in high volume, on line blood collection environments, where higher yields of critically needed cellular blood components, like plasma, red blood cells, and platelets, can be realized in reasonable short processing times.

The operational and performance demands upon such fluid processing systems become more complex and sophisticated, even as the demand for smaller and more portable systems intensifies. The need therefore exists for automated blood processing controllers that can gather and generate more detailed information and control signals to aid the operator in maximizing processing and separation efficiencies.

SUMMARY OF THE INVENTION

According to one aspect of the invention, processing systems and methods comprise a separation device that, in use, performs a separation process including separation of red blood cells from blood or a suspension that contains red blood cells. The systems and methods include an outlet line coupled to the separation device to remove red blood cells from the separation device, at least in part, while the separation process occurs. According to this aspect of the invention, a sensor is associated with the outlet line to sense hematocrit of red blood cells removed from the separation device and to generate a sensed hematocrit output. A controller is coupled to the separation device to control removal of red blood cells from the separation device based, at least in part, upon the sensed hematocrit output.

In one embodiment, the controller controls removal of red blood cells by, e.g., adjusting flow rate of red blood cells in the outlet line based, at least in part, upon the sensed hematocrit output.

In one embodiment, the controller compares the sensed hematocrit output to a predetermined red blood cell hematocrit value and controls removal of red blood cells based, at least in part, upon the comparison.

In one embodiment, the controller monitors deviation between the sensed hematocrit output and a predetermined red blood cell hematocrit value and controls removal of red blood cells based, at least in part, upon the deviation, e.g., based upon the magnitude of the deviation, or the change of the deviation over time.

In one embodiment, the sensor optically senses the hematocrit of red blood cells removed from the separation device to generate the sensed hematocrit output.

According to another aspect of the invention, systems and methods employ a separation device that, in use, performs a separation process that includes separation of red blood cells and plasma from blood or a suspension containing red blood cells and plasma. An inlet line is coupled to the separation device to convey blood for suspension into the separation device at a controlled blood flow rate Qb, at least in part, while the separation process occurs. A plasma outlet line is coupled to the separation device to convey plasma from the separation device at a controlled plasma flow rate Qp, at least in part, while the separation process occurs. A red blood cell outlet line is coupled to the separation device to remove red blood cells from the separation device at a red blood cell flow rate Qrbc, at least in part, while the separation process occurs, whereby Qrbc=Qb−Qp. A sensor associated with the outlet line senses hematocrit of red blood cells removed from the separation device and generates a sensed hematocrit output. A controller coupled to the separation device controls a ratio between Qb and Qp based, at least in part, upon the sensed hematocrit output.

It has been discovered that, during separation of whole blood, at a determinable high threshold of red blood cell hematocrit HCTRBC, platelets will cease exiting the separation device with red blood cells. At this given high threshold value HCTRBC, platelets tend to remain with the plasma in the separation device, and thereby be subject to mixing with the plasma. Based upon this discovery, a blood processing set point for red blood cell hematocrit SET_HCTRBC can be set to approach, but not exceed, this high threshold red blood cell hematocrit value. Adjusting the ratio (QP)/(QWB) to achieve (SET_HCTRBC) during a given plasma collection procedure serves to optimize plasma collection parameters for that procedure, as well as mediate against or avoid over spill conditions. Using SET_HCTRBC as a control allows (QP) to be maximized to optimize procedure time and maximize red blood cell hematocrit, while inducing platelets to leave the chamber with the red blood cells to avoid an over spill condition.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
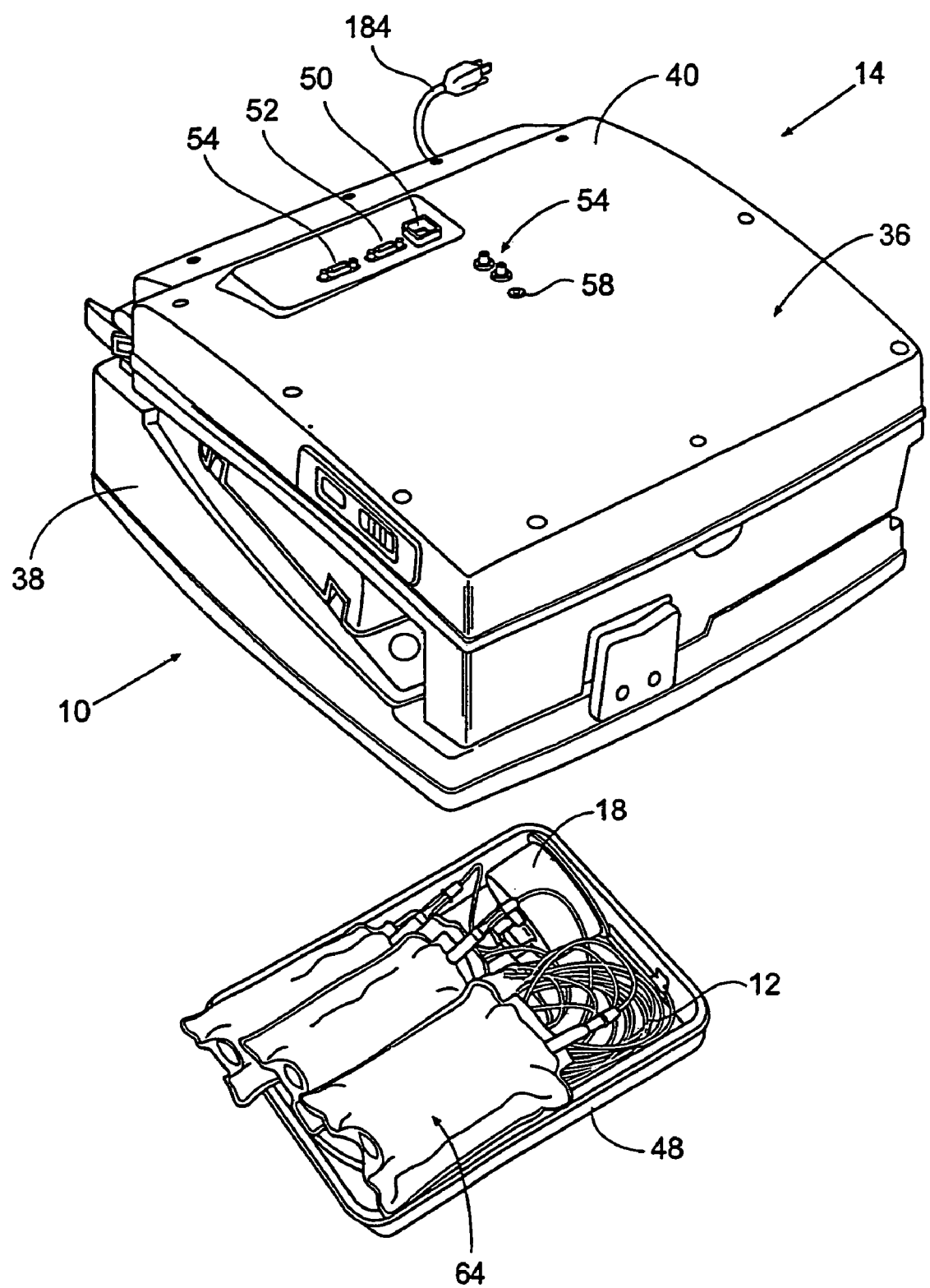
FIG. 1 is a perspective view of a fluid processing system, ideally suited for blood processing, comprising a blood processing device (shown in a closed condition for transport and storage) and a disposable liquid and blood flow set, which interacts with the blood processing device to cause separation and collection of one or more blood components (shown packaged in a tray for transport and storage before use).

FIG. 1 shows a fluid processing system 10 that embodies the features of the invention. The system 10 can be used for processing various fluids.

The system 10 is particularly well suited for processing whole blood and other suspensions of biological cellular materials. Accordingly, the illustrated embodiment shows the system 10 used for this purpose.

I. System Overview

The system 10 includes two principal components. These are: (i) a blood processing device 14—shown in FIG. 1 in a closed condition for transport and storage, and in FIGS. 2 and 3 in an opened condition for operation); and (ii) a liquid and blood flow set 12, which interacts with the blood processing device 14 to cause separation and collection of one or more blood components—the set 12 being shown in FIGS. 1 and 4 packaged in a tray 48 for transport and storage before use, and in FIGS. 5 and 6 removed from the tray 48 and mounted on the blood processing device 14 for use.

A. The Processing Device

The blood processing device 14 is intended to be a durable item capable of long term use. In the illustrated and preferred embodiment, the blood processing device 14 is mounted inside a portable housing or case 36. The case 36 presents a compact footprint, suited for set up and operation upon a table top or other relatively small surface. The case 36 is also intended to be transported easily to a collection site.

Figure 2:
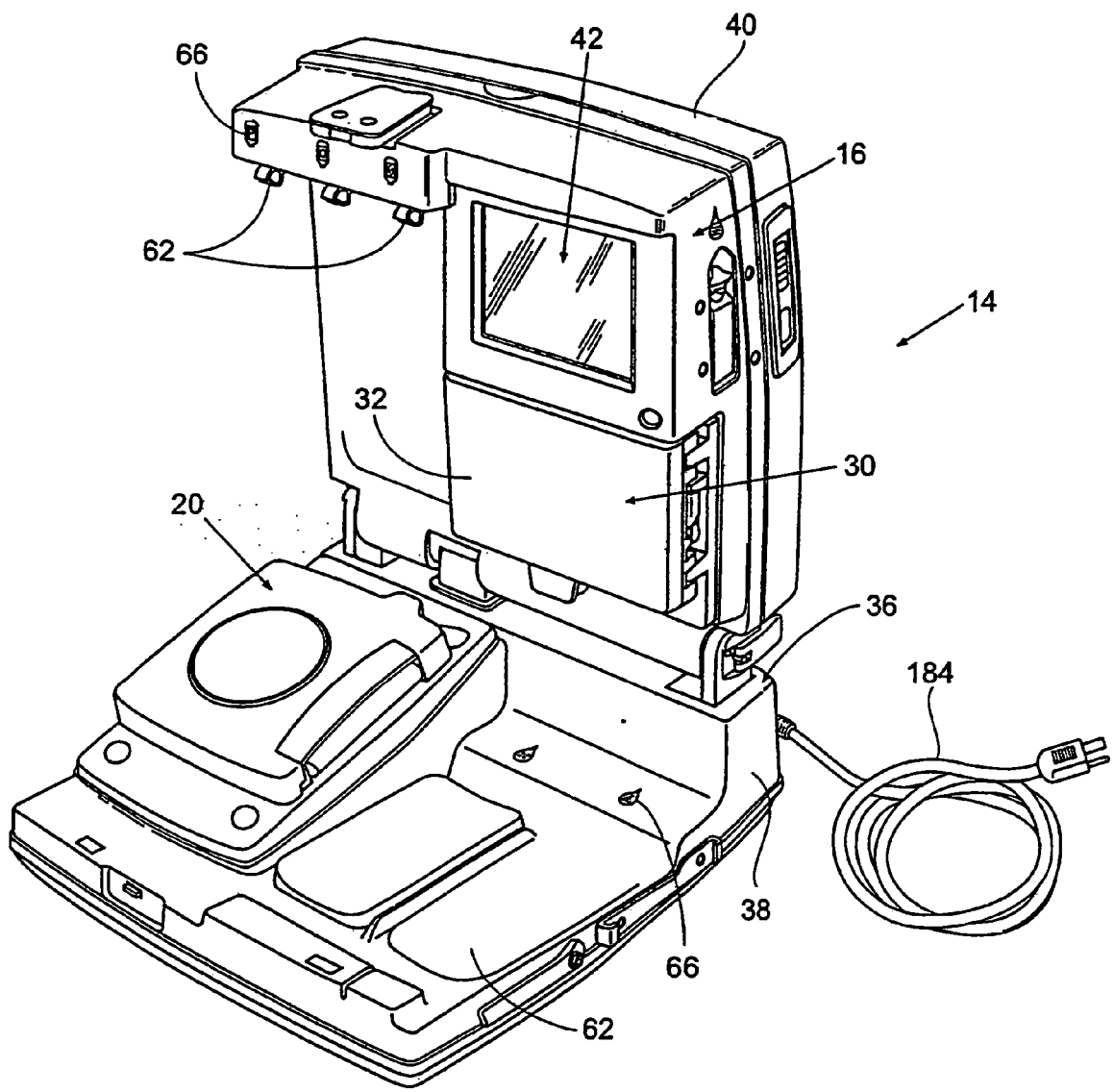
FIG. 2 is a perspective view of the blood processing device shown in FIG. 1, shown in an opened condition for operation.
Figure 3:
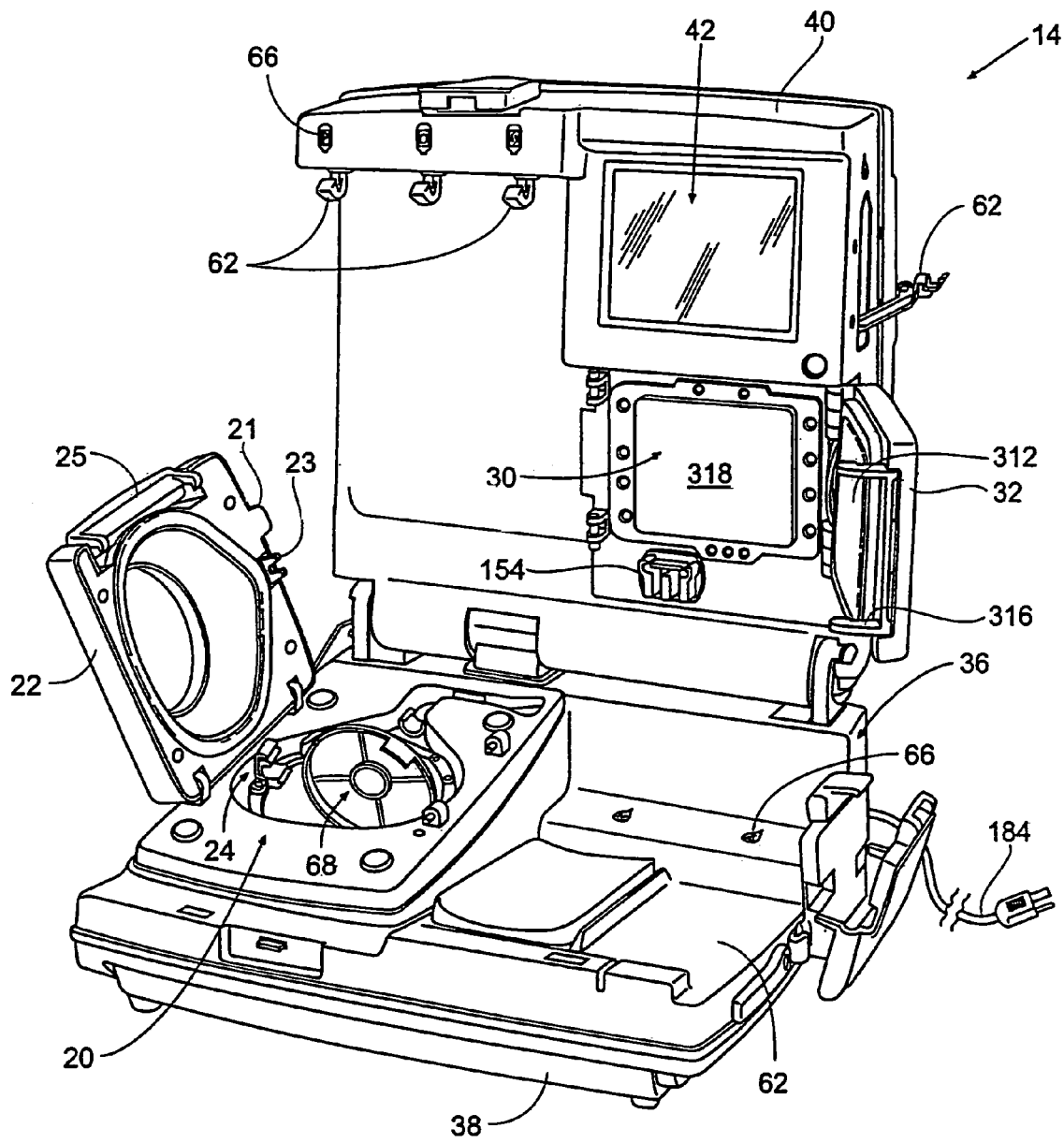
FIG. 3 is a perspective view of the blood processing device shown in FIG. 2, with the centrifugal station open to receive a blood processing chamber and the pump and valve station open to receive a fluid pressure-actuated cassette.
Figure 4:
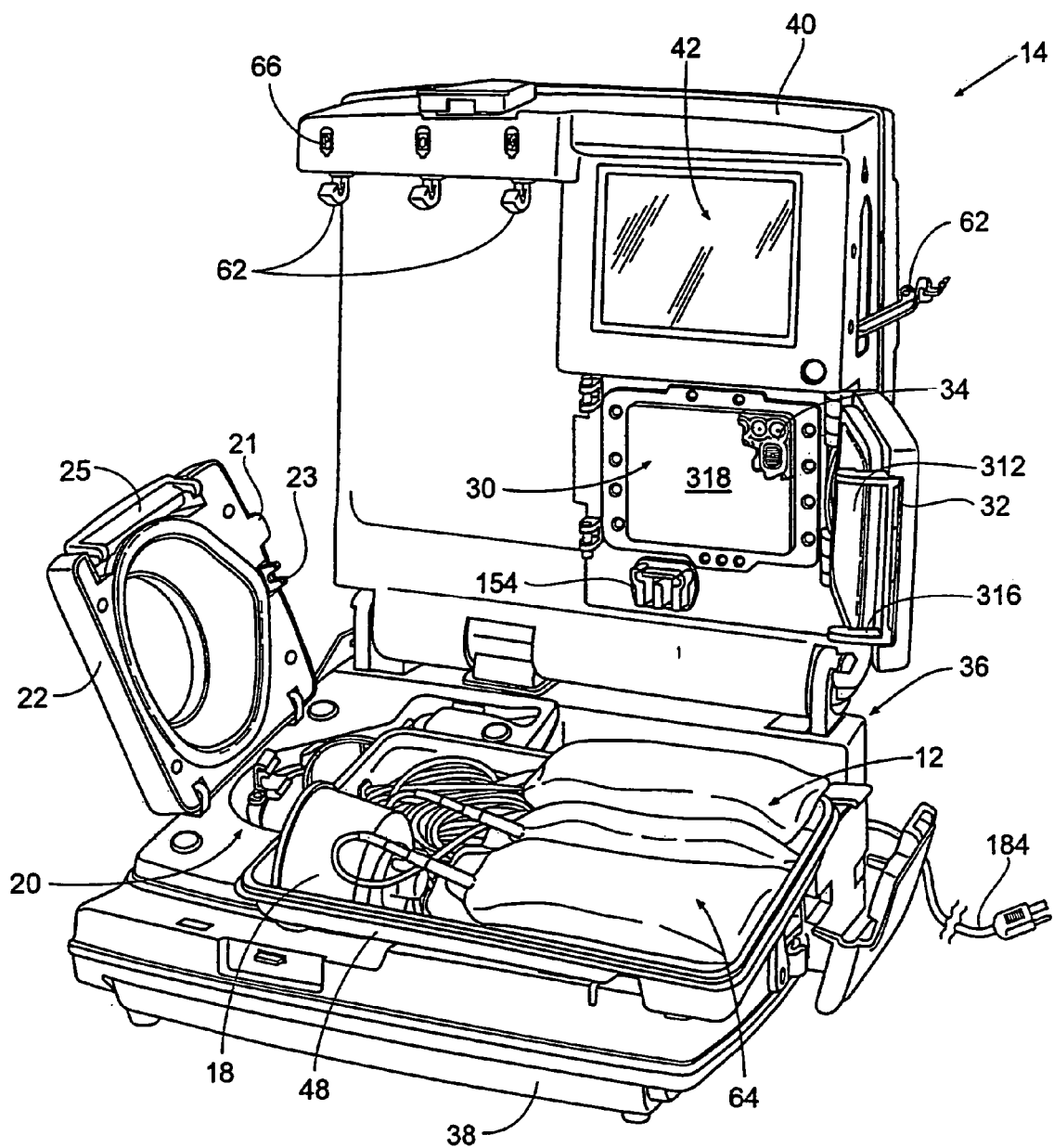
FIG. 4 is a perspective view of the blood processing device shown in FIG. 3, with the tray containing the disposable liquid and blood flow set positioned for loading the flow set on the device.

The case 36 includes a base 38 and a hinged lid 40, which closes for transport (as FIG. 1 shows) and which opens for use (as FIGS. 2 to 4 show). In use, the base 38 is intended to rest in a generally horizontal support surface. The case 36 can be formed into a desired configuration, e.g., by molding. The case 36 is preferably made from a lightweight, yet durable, plastic material.

A controller 16 is carried onboard the device 14. The controller 16 governs the interaction between the components of the device 14 and the components of the flow set 12 to perform a blood processing and collection procedure selected by the operator. In the illustrated embodiment, the controller 16 comprises a main processing unit (MPU), which can comprise, e.g., a Pentium™ type microprocessor made by Intel Corporation, although other types of conventional microprocessors can be used. The MPU can be mounted inside the lid 40 of the case 36. A power supply with power cord 184 supplies electrical power to the MPU and other components of the device 14.

Preferably, the controller 16 also includes an interactive user interface 42, which allows the operator to view and comprehend information regarding the operation of the system 10. In the illustrated embodiment, the interface 42 is implemented on an interface screen carried in the lid 40, which displays information for viewing by the operator in alpha-numeric format and as graphical images.

Further details of the controller 16 can be found in Nayak et al, U.S. Pat. No. 6,261,065, which is incorporated herein by reference. Further details of the interface can be found in Lyle et al, U.S. Pat. No. 5,581,687, which is also incorporated herein by reference.

As FIG. 1 shows, the lid 40 can be used to support other input/outputs to couple other external devices to the controller 16 or other components of the device 14. For example, an ethernet port 50, or an input 52 for a bar code reader or the like (for scanning information into the controller 16), or a diagnostic port 54, or a port 56 to be coupled to a pressure cuff 60 worn by a donor to enhance blood flow rates during blood processing (see, e.g., FIGS. 23 and 24), or a system transducer calibration port 58, can all be conveniently mounted for access on the exterior of the lid 40, or elsewhere on the case 36 of the device 14.

B. The Flow Set

Figure 5:
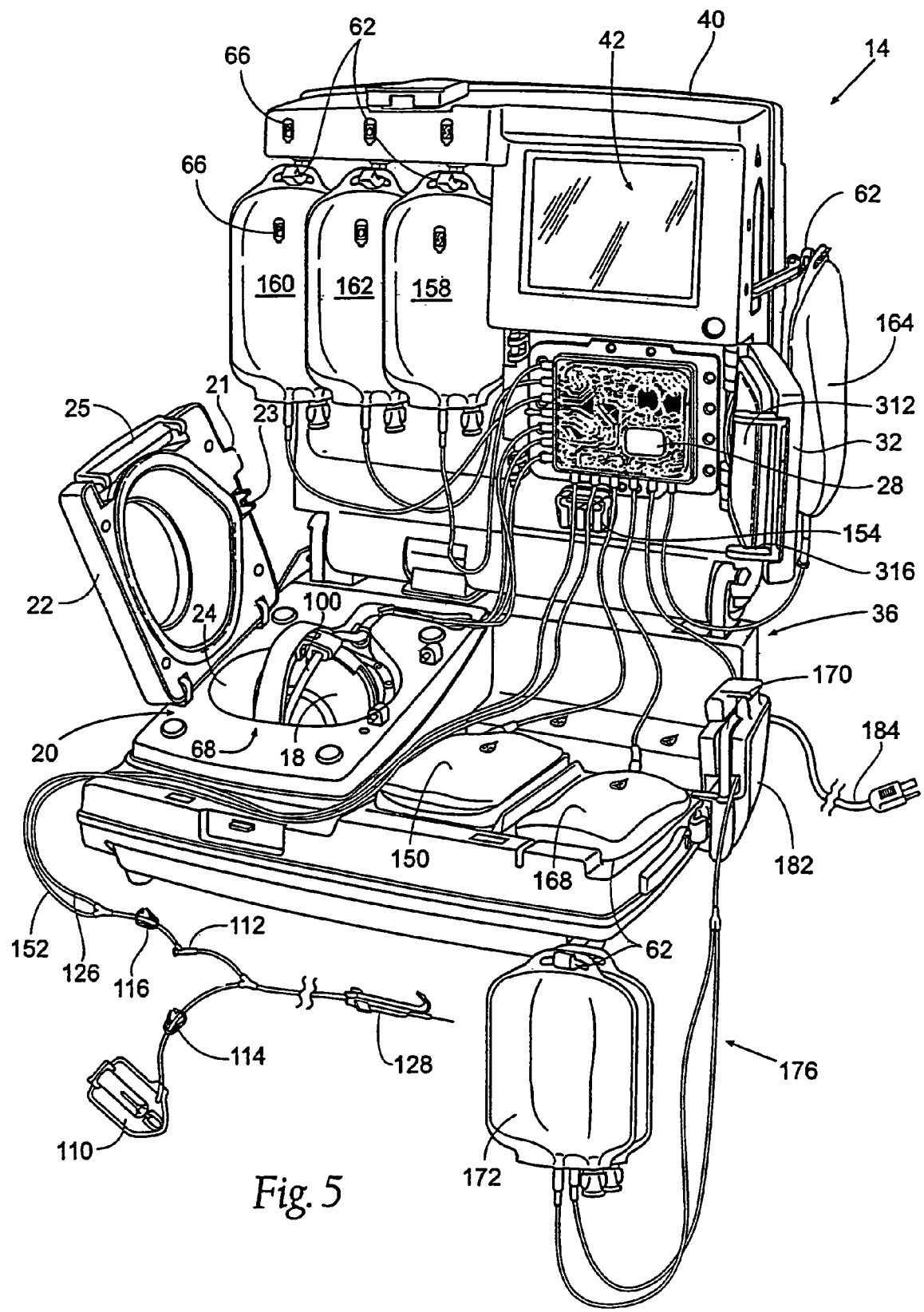
FIGS. 5 and 6 are, respectively, right and left side perspective views of the blood processing device shown in FIG. 2 after the liquid and blood flow set has been loaded onto the device for use.

The flow set 12, is intended to be a sterile, single use, disposable item. Before beginning a given blood processing and collection procedure, the operator loads various components of the flow set 12 in association with the device 14 (as FIGS. 4 and 5 show). The controller 16 implements the procedure based upon preset protocols, taking into account other input from the operator. Upon completing the procedure, the operator removes the flow set 12 from association with the device 14. The portion of the set 12 holding the collected blood component or components are removed from the device 14 and retained for storage, transfusion, or further processing. The remainder of the set 12 is removed from the device 14 and discarded.

The flow set includes a blood processing chamber 18, a fluid actuated pump and valve cassette 28, and an array associated processing containers 64 and flow tubing coupled to the chamber 18 and the cassette 28, as will be identified in greater detail later.

1. The Blood Processing Chamber

In the illustrated embodiment (see FIG. 5), the flow set 12 includes a blood processing chamber 18 designed for use in association with a centrifuge. The processing device 14 includes a centrifuge station 20 (see FIGS. 2 and 3, which receives the processing chamber 18 for use (see FIG. 5).

Figure 6:
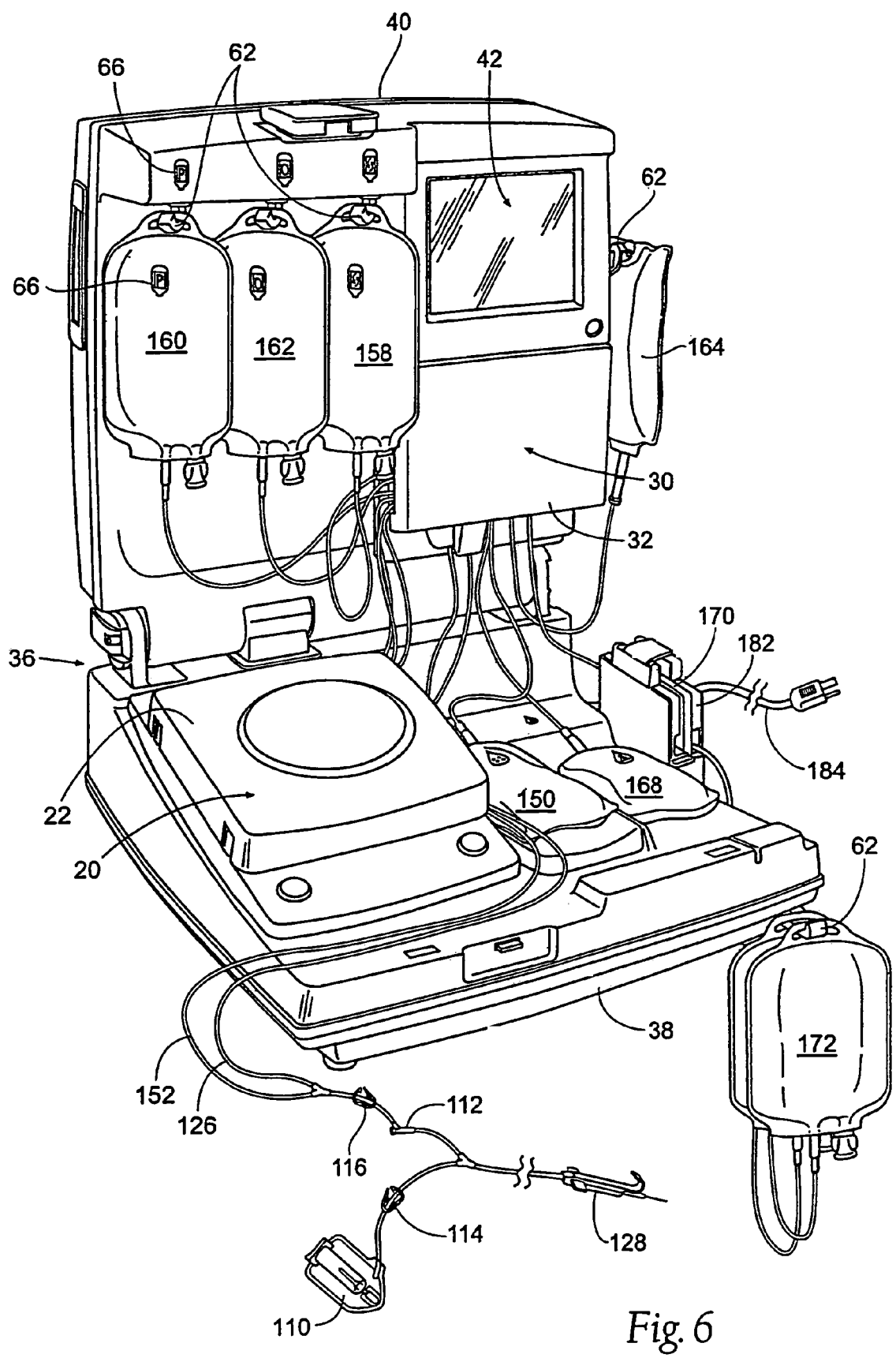

As FIGS. 2 and 3 show, the centrifuge station 20 comprises a compartment 24 formed in the base 38. The centrifuge station 20 includes a door 22. The door 22 opens (as FIGS. 3 and 5 show) to allow loading of the processing chamber 18 into the compartment 24. The door 22 closes (as FIGS. 2 and 6 show) to enclose the processing chamber 18 within the compartment 24 during operation.

The centrifuge station 20 rotates the processing chamber 18. When rotated, the processing chamber 18 centrifugally separates whole blood received from a donor into component parts, principally, red blood cells, plasma, and intermediate layer called the buffy coat, which is populated by platelets and leukocytes. As will be described later, the configuration of the chamber 18 can vary according to the intended blood separation objectives.

2. The Fluid Pressure-Actuated Cassette

In the illustrated embodiment, the set 12 also includes a fluid pressure-actuated cassette 28 (see FIG. 5). The cassette 28 provides a centralized, programmable, integrated platform for all the pumping and valving functions required for a given blood processing procedure. In the illustrated embodiment, the fluid pressure comprises positive and negative pneumatic pressure, although other types of fluid pressure can be used.

As FIG. 5 shows, the cassette 28 is mounted for use in a pneumatic actuated pump and valve station 30, which is located in the lid of the 40 of the case 36. The pump and valve station 30 includes a door 32 that is hinged to move between an opened position, exposing the pump and valve station 30 (see FIG. 3) for loading and unloading the cassette 28, and a closed position, enclosing the cassette 28 within the pump and valve station 30 for use (shown in FIG. 6). The pump and valve station 30 includes a manifold assembly 34 (see FIG. 4) located behind a valve face gasket 318. The manifold assembly 34 applies positive and negative pneumatic pressure to the cassette 28 through the gasket 318, when the cassette 28 is when mounted on the pump and valve station 30. The pneumatic pressures direct liquid flow through the cassette 28.

Further details of the cassette 28 and the operation of the pump and valve station 30 will be described later. Additional details can also be found in Nayak et al, U.S. Pat. No. 6,261,065, which has been incorporated herein by reference.

3. Blood Processing Containers and Tubing

Referred back to FIGS. 5 and 6, the flow set 16 also includes an array of tubes and containers in flow communication with the cassette 28 and the chamber 18. The arrangement of tubes and containers can vary according to the processing objectives. Representative blood processing procedures and the associated flow sets accommodating such procedures will be described later.

An umbilicus 100 forms a part of the flow set 16. When installed, the umbilicus 100 links the rotating processing chamber 18 with the cassette 28 without need for rotating seals. The umbilicus 100 can be made from rotational-stress-resistant plastic materials, such as Hytrel® copolyester elastomers (DuPont).

Figure 7:
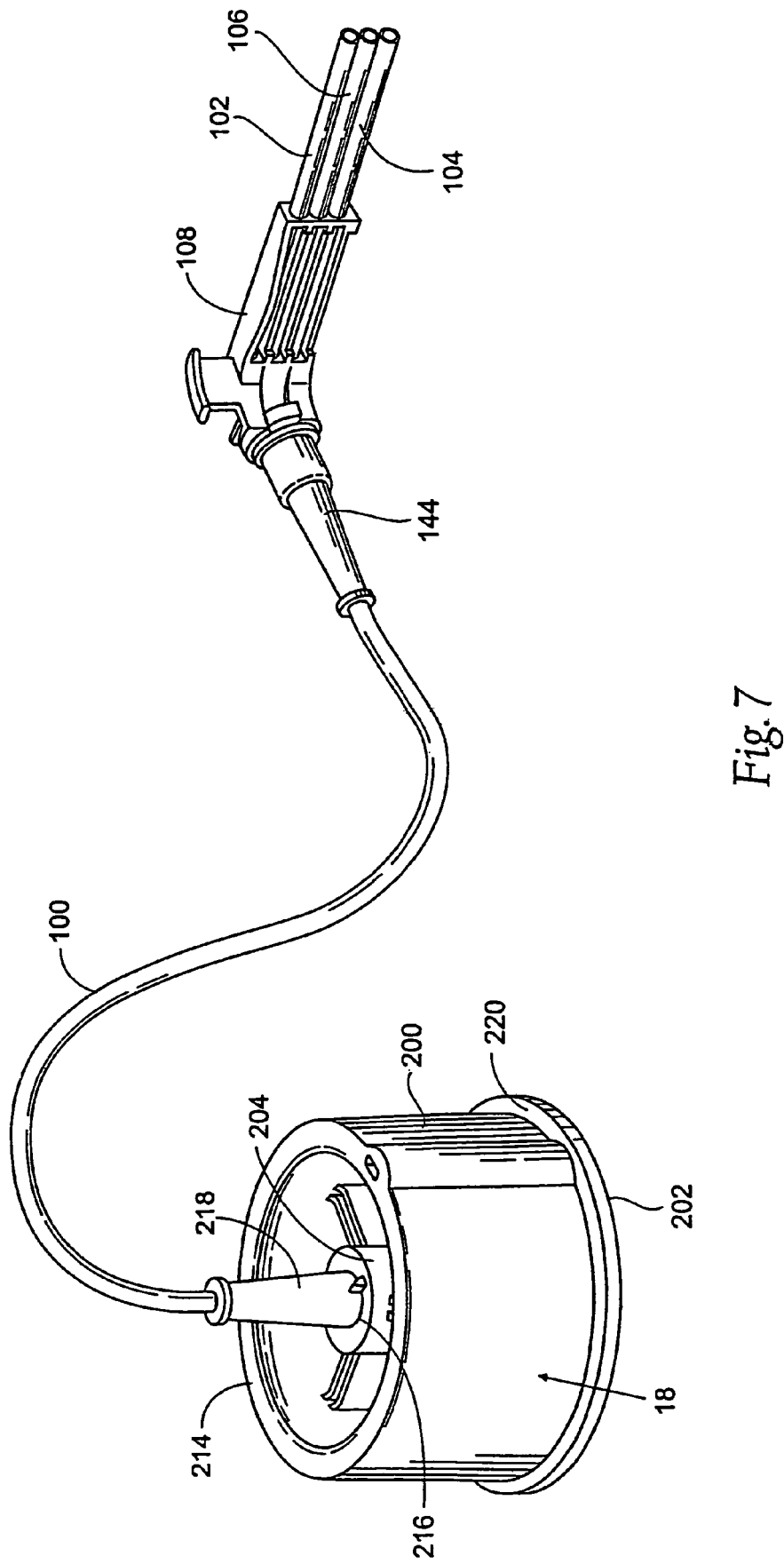
FIG. 7 is a perspective view of the blood processing chamber and attached umbilicus that forms a part of the liquid and blood flow set shown in FIGS. 5 and 6.

Referring now to FIG. 7, tubes 102, 104, and 106 extend from the proximal end of the umbilicus 100. The tube 102 conveys whole blood into the processing chamber 18 for separation. The tubes 104 and 106 convey, respectively, centrifugally separated red blood cells and plasma from the processing chamber 18. The plasma can either be rich or poor in platelets, depending upon the processing objectives.

As FIG. 7 shows, a fixture 108 gathers the tubes 102, 104, and 106 adjacent the umbilicus 100 in a compact, organized, side-by-side array outside the centrifuge station 20. The fixture 108 allows the tubes 102, 104, and 106 to be placed and removed as a group in association with an optical sensing station 46 (see FIGS. 9, 10, and 11), which is located adjacent to the centrifuge station 20 outside the chamber 18.

The optical sensing station 46 optically monitors the presence or absence of targeted blood components (e.g., red blood cells and platelets) in blood conveyed by the tubes 104 and 106. The sensing station 46 provides outputs reflecting the presence or absence of such blood components. This output is conveyed to the controller 16. The controller 16 processes the output and generates signals to control processing events based, in part, upon the optically sensed events. Further details of the operation of the controller to control processing events based upon optical sensing will be described later. Additional details can also be found in Nayak et al, U.S. Pat. No. 6,261,065, which has been incorporated herein by reference.

As shown (see FIGS. 5 and 6), the flow set 16 includes a phlebotomy needle 128, through which a donor can be coupled to the system 10 for blood processing. In FIGS. 5 and 6, the flow set 16 also includes a blood sampling assembly 110. The blood sampling assembly 110 allows for the collection of one or more samples of the donor's blood at the commencement of a given blood processing procedure, through the phlebotomy needle 128. A conventional manual clamp 114 (e.g., a Roberts Clamp) is provided to control blood flow into the sampling assembly 110.

As also shown in FIGS. 5 and 6, the flow set 16 can include an in-line injection site 112. The injection site 112 allows a technician to introduce saline or another physiologic liquid or medication into the donor, if necessary, using the phlebotomy needle 128, and without requiring an additional needle stick.

An additional in-line manual clamp 116 is desirably included upstream of the blood sampling assembly 110 and the injection site 112. This clamp 116 makes it possible to quickly isolate the donor from the flow set 16, if donor safety or comfort requires. Alternatively, a separate hemostat device (not shown) can be applied for the purpose.

As FIGS. 1 and 2 also show, the device 14 can include other components compactly arranged to aid blood processing. In addition to the centrifuge station 20 and pump and valve station 30, already described, the device includes one or more weigh stations 62 and other forms of support for containers. The arrangement of these components on the device 14 can, or course, vary.

In the illustrated embodiment (see FIG. 3), the weigh stations 62 comprise a series of container hangers/weigh sensors arranged along the top of the lid 40. In the illustrated embodiment, additional swing-out hangers/weigh sensors are also provided on the side of the lid 40 and the base. In use (see FIGS. 5 and 6), containers are suspended on the weigh stations 62. As FIGS. 5 and 6 also show, pictorial icons 66 applied to the lid 40 adjacent to the weigh stations 62 match pictorial icons 66 applied on the containers. By matching the icons 66, the operator is visually guided to place the proper containers on the intended weigh stations 62.

The weigh stations 62 can also comprise molded recesses in the base 38 to rest containers. Pictorial icons 66 on the base 38 adjacent the stations 62 match pictorial icons 66 on the containers to guide the operator in proper placement of containers during set up.

As blood or liquids are received into and/or dispensed from the containers during processing, the weigh stations 62 provide output reflecting weight changes over time. This output is conveyed to the controller 16. The controller 16 processes the incremental weight changes to derive fluid processing volumes. The controller generates signals to control processing events based, in part, upon the derived processing volumes. Further details of the operation of the controller 16 to control processing events will be described later. Additional details can also be found in Nayak et al, U.S. Pat. No. 6,261,065, which has been incorporated herein by reference.

4. Blood Processing Procedures

Under the control of the controller 16, the system 10 can be conditioned to perform different blood processing procedures. The MPU includes an application control manager that administers the activation of a library of control applications. Each control application prescribes procedures for carrying out given functional tasks using the centrifuge station 20 and the pump and valve station 30 in a predetermined way. The applications can, e.g., reside as process software in EPROM's in the MPU.

As will be described later, through selective application of pressure to the cassette 28, it is possible to use the same cassette 28 to carry out different blood collection procedures.

For the sake of illustration, the implementation of two clinical procedures will be described: (1) a plasma collection procedure; and (2) a double unit red blood cell collection procedure. During a plasma collection procedure, whole blood from a donor is centrifugally processed to yield up to 880 ml of plasma for collection. All red blood cells are returned to the donor. During a double unit red blood cell collection procedure, whole blood from a donor is centrifugally processed to yield up to two units (approximately 500 ml) of red blood cells for collection. All plasma constituent is returned to the donor.

Although not described in detail, other clinical procedures can be conducted by the system 10. For example, a plasma/red blood cell collection procedure can be performed, during which whole blood from a donor is centrifugally processed to collect up to about 550 ml of plasma and up to about 250 ml of red blood cells. The portion of the red blood cells not retained for collection are periodically returned to the donor during blood separation. Plasma collected in excess of the 550 ml target and red blood cells collected in excess of the 250 ml target are also returned to the donor at the end of the procedure. As another example, during the course of a plasma collection and/or red blood cell collection procedure, the buffy coat interface can be removed from the chamber 18 and collected. With subsequent processing to remove leukocytes, the buffy coat serves as a source of platelets.

Further details of the various blood collection procedures that the system 10 can accomplish are described in U.S. Pat. No. 6,261,065, which has been incorporated herein by reference.

II. Other Technical Features of the Blood Separation Components of the System

The blood processing chamber 18 and the centrifuge station 20 of the system 10 desirably possess other technical features that support the implementation of diverse blood processing protocols.

A. The Blood Processing Chamber

In the illustrated embodiment (see FIGS. 7 and 8), the processing chamber 18 is preformed in a desired shape and configuration, e.g., by injection molding, from a rigid, biocompatible plastic material, such as a non-plasticized medical grade acrilonitrile-butadiene-styrene (ABS). In this arrangement, the chamber 18 includes two principal components—a base component 200 and a lid component 202.

The base component 200 includes a center hub 204. The hub 204 is surrounded by inside and outside annular walls 206 and 208 that define a circumferential blood separation channel 210. One or more radial passages 212 extend from the hub 204 and communicate with the channel 210. Blood and other fluids are directed from the hub 204 into and out of the channel 210 through these passages 212. A molded wall 214 forms an axial boundary of the separation channel 210. The lid component 202 also forms another axial boundary of the separation channel 210. While both axial boundaries are shown to be generally flat (i.e., normal to the rotational axis), it should be appreciated that the axial boundaries can be tapered, rounded, V-shape, and the like.

The underside of the base component 200 includes a shaped receptacle 216 that receives a shaped mount 218 on the far end of the umbilicus 100. The mount 218 can be secured to the receptacle 216 in various ways—e.g., by a tight, dry press fit or by solvent bonding or by ultrasonic welding—to couple the umbilicus 100 in fluid communication with the channel 210. The far end of the umbilicus 100 and the base component 200 rotate as a unit.

All contours, ports, channels, and walls that affect the dynamics of the blood separation process are preformed in the base component 200 in one or more injection molding operations. The contours, ports, channels, and walls that are preformed in the base component 200 can vary, according to the particular separation objectives desired. Representative examples will be described in greater detail later.

B. The Centrifuge Station

The centrifuge station 20 (see FIG. 9) includes a centrifuge assembly 68. The centrifuge assembly 68 is constructed to receive and support the molded processing chamber 18 and umbilicus 100 for use.

Figure 9:
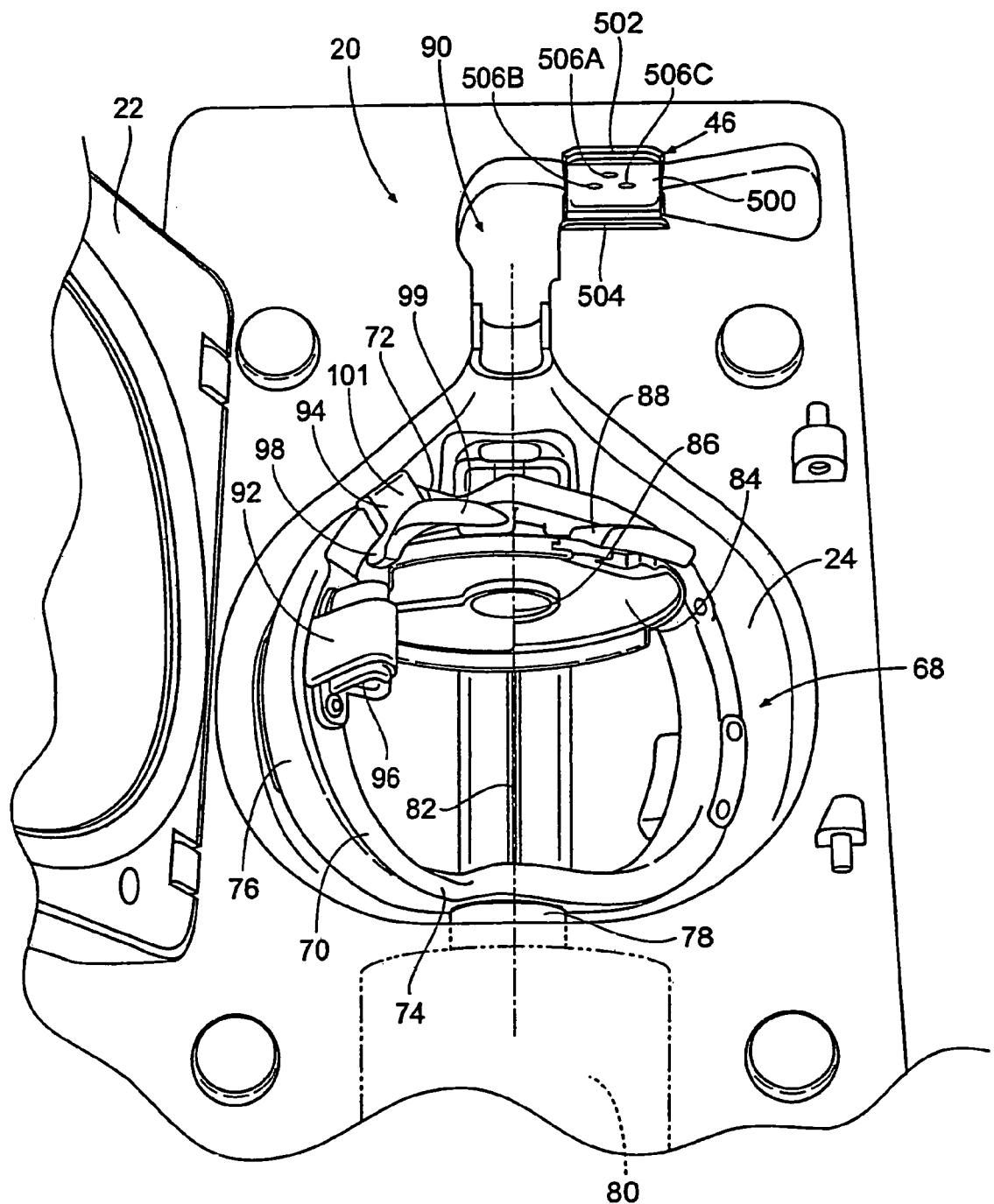
FIG. 9 is a perspective view of the interior of the centrifuge station of the device shown in FIGS. 5 and 6, with the station door opened to receive a blood processing chamber of a type shown in FIG. 7.

As illustrated in FIG. 9, the centrifuge assembly 68 includes a frame or yoke 70 having bottom, top, and side walls 72, 74, 76. The yoke 70 spins on a bearing element 78 (FIG. 9) attached to the bottom wall 72. An electric drive motor 80 is coupled to the bottom wall 72 of the yoke 70, to rotate the yoke 70 about an axis 82. In the illustrated embodiment, the axis 82 is essentially horizontal (see FIG. 3), although other angular orientations can be used. The motor 80 is capable of rotating the yoke 70 in either clockwise or counterclockwise directions, depending upon commands issued by the controller 16.

A carrier or rotor plate 84 spins within the yoke 70 about its own bearing element 86, which is attached to the top wall 74 of the yoke 70. The rotor plate 84 spins about an axis that is generally aligned with the axis of rotation 82 of the yoke 70.

As FIG. 7 shows, the top of the processing chamber 18 includes an annular lip 220, to which the lid component 202 is secured. As FIG. 10 shows, the rotor plate 84 includes a latching assembly 88 that removably grips the lip 220, to secure the processing chamber 18 on the rotor plate 84 for rotation.

Details of the latching assembly 88 can be found in co-pending U.S. patent application Ser. No. 09/976,829, filed Oct. 13, 2001 and entitled "Blood Separation Systems and Methods with Quick Attachment of a Blood Separation Chamber to a Centrifuge Rotor," which has been incorporated herein by reference.

Figure 10:
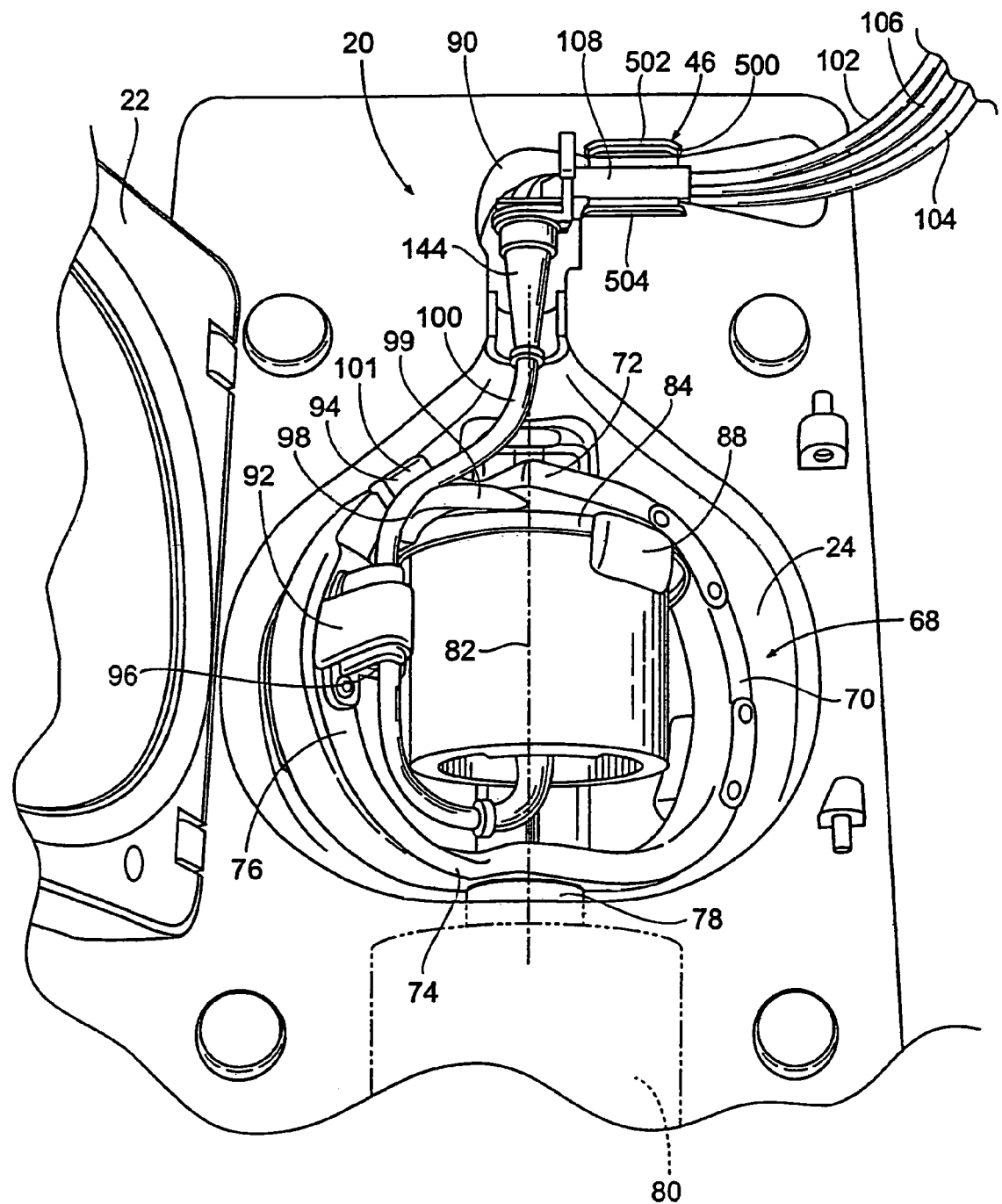
FIG. 10 is a perspective view of the interior of the centrifuge station shown in FIG. 9 after a blood processing chamber of a type shown in FIG. 7 has been loaded for use.

As FIG. 10 best shows, a sheath 144 on the near end of the umbilicus 100 fits into a preformed, recessed pocket 90 in the centrifuge station 20. The pocket 90 holds the near end of the umbilicus 100 in a non-rotating stationary position aligned with the mutually aligned rotational axes 82 of the yoke 70 and rotor plate 84.

Figure 11:
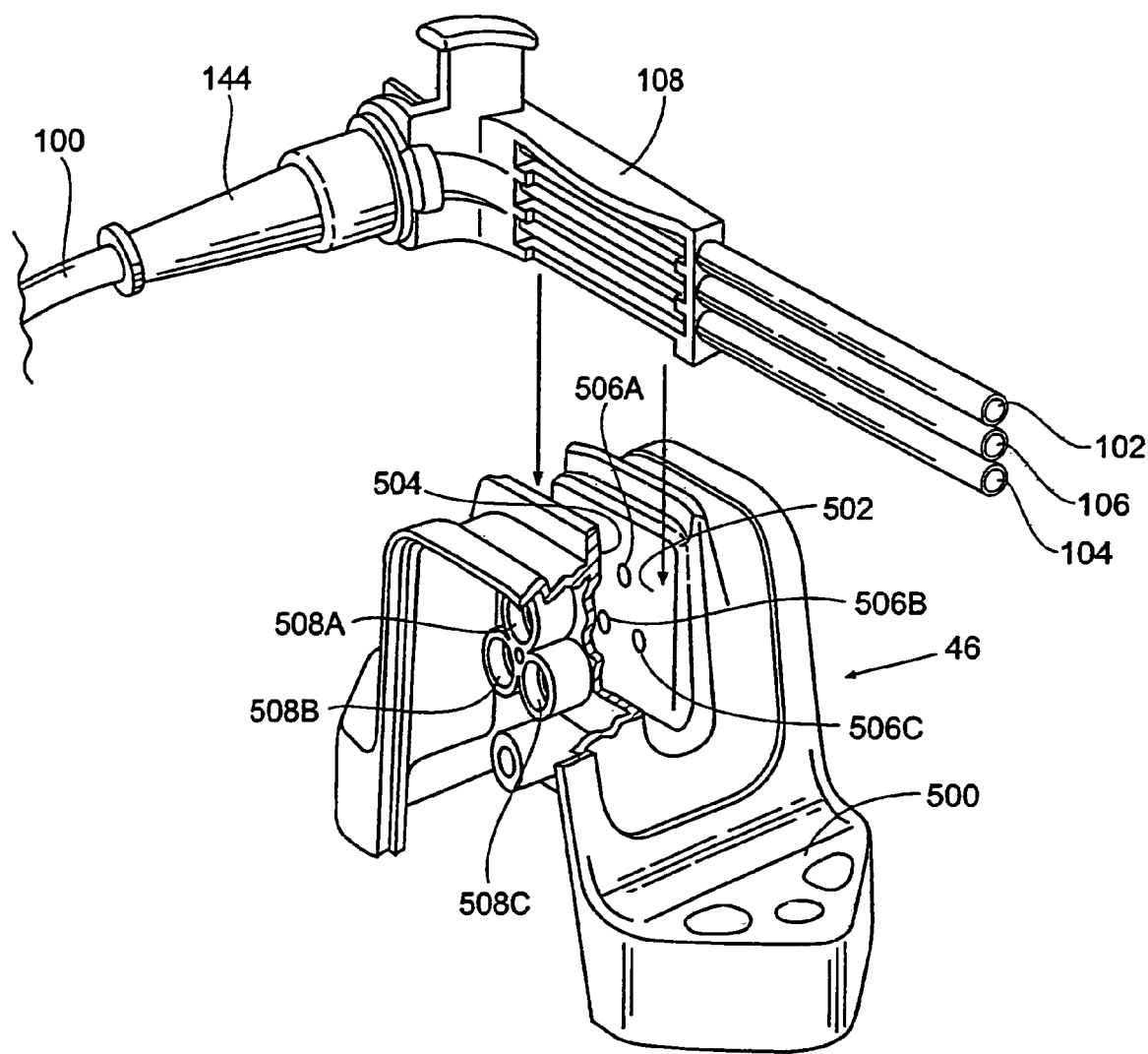
FIG. 11A is an enlarged perspective view of a fixture that is carried by the umbilicus shown in FIG. 7, showing its intended association with an optical sensing station that forms a part of the device shown in FIGS. 5 and 6.
FIG. 11B is a side section view of the optical sensing station shown in FIG. 11A.
FIG. 11C is an exploded perspective view of the optical sensing station shown in FIG. 11A.
FIG. 11D is a top view of the optical sensing station shown in FIG. 11A.
FIGS. 11E and 11F are schematic views of a circuit that can be used in association with the optical sensing station shown in FIG. 11A.
Figure 11B:
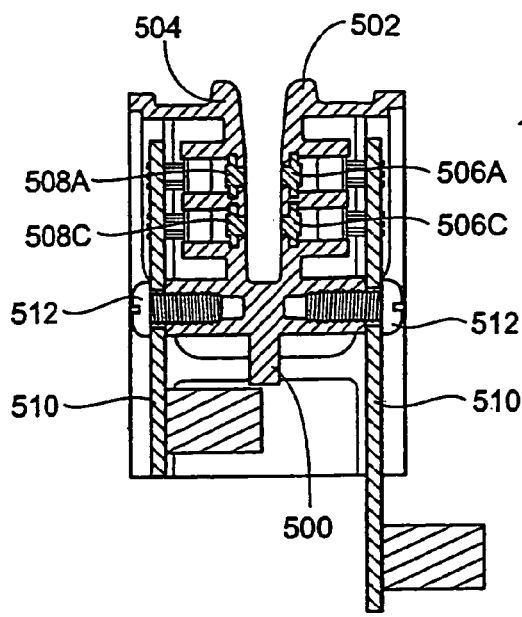
Figure 11C:
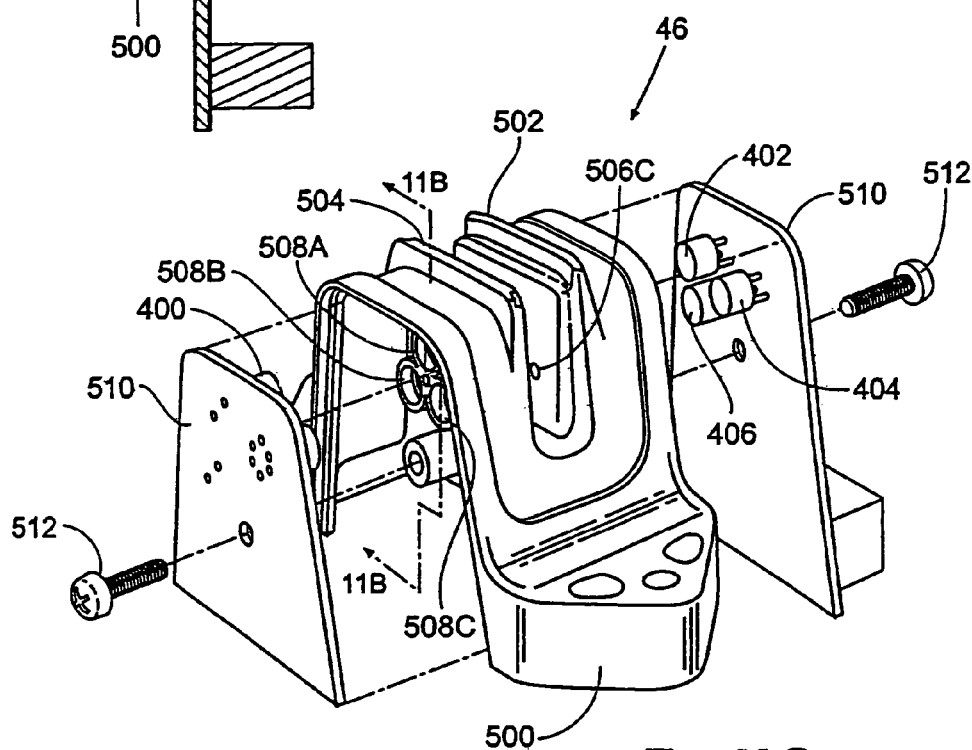
Figure 11D:
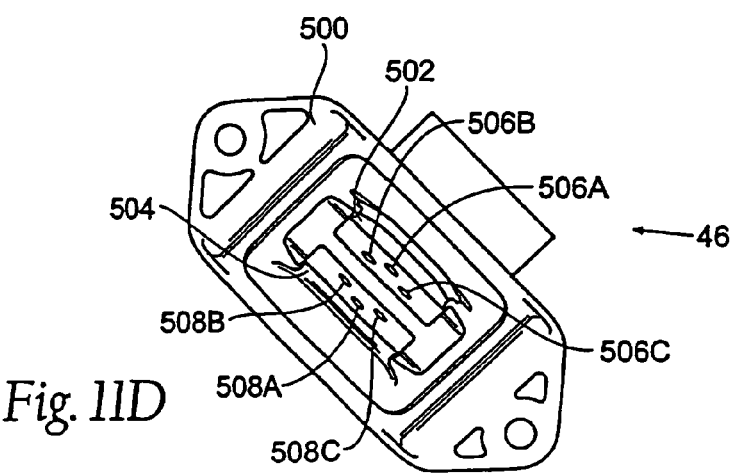

The preformed pocket 90 is also shaped to accommodate loading of the fixture 108 at the same time the umbilicus sheath 144 is inserted. The tubes 102, 104, and 106 are thereby placed and removed as a group in association with the sensing station 46, which is also located within the pocket 90, as FIG. 11 shows.

Umbilicus drive or support members 92 and 94 (see FIGS. 9 and 10) are carried by a side wall 76 of the yoke 70. When the rotor plate 84 is located in a prescribed rotational position, the support members 92 and 94 are presented on the left side of the processing chamber 18 to receive the umbilicus 100 at the same time that the sheath 144 and fixture 108 are manipulated for fitting into the pocket 90.

As FIG. 10 shows, one member 92 receives the mid portion of the umbilicus 100. The member 92 includes a surface against which the mid portion of the umbilicus 100 rests. The surface forms a channel 96, which faces generally toward the yoke 70. The channel 96 accommodates passage of the mid portion of the umbilicus 100, directing the upper portion of the umbilicus toward the other member 94. The channel 96 inhibits travel of the mid portion of the umbilicus 100 in radial directions toward and away from the rotational axis 82. However, the channel 96 permits rotation or twisting of the umbilicus 100 about its own axis. Before use, the surface of the channel 96 is generally convex. The convex configuration is intended to be sacrificial, in that the material of the convex surface is intended to be worn away during use by rotational contact with the umbilicus 100. The convex configuration is dynamically changed by contact with the umbilicus during use, to form an final contact configuration that is dictated by the mechanical and frictional interaction between the channel 96 and the umbilicus 100 during use.

The other member 94 receives the upper portion of the umbilicus 100, which the member 92 directs toward it. The member 94 includes a surface against which the upper portion of the umbilicus 100 rests. The surface forms a channel 98 inclined toward the top wall 72 of the yoke 70. The channel 98 generally faces away from the yoke 70, and is thereby in a reverse facing relationship with the channel 96. To provide a transitional path for the umbilicus between the two oppositely facing channels 96 and 98, the channel 96 is offset slightly outward from the channel 98. The channel 98 guides the upper portion of the umbilicus 100 toward the recessed pocket 90, which is located axially above the top wall 72 of the yoke 70, where the umbilicus sheath 144 and fixture 108 are fitted. Like the channel 96, the channel 98 inhibits travel of the upper portion of the umbilicus 100 in radial directions toward and away from the rotational axis 82. However, like the channel 96, the channel 98 permits rotation or twisting of the umbilicus 100 about its own axis.

Because the support channels 96 and 98 are arranged in a reverse facing relationship, the channels 96 and 98 mutually engage the mid region of the umbilicus in a complementary, "reverse grip" fashion regardless of the direction of rotation of the yoke 70.

The inward facing orientation of the channel 96 best captures the umbilicus during rotation of the yoke 70 in the counterclockwise direction (when viewed from the top of the rotor plate 84). This, in turn, stabilizes the remainder of the umbilicus for engagement with the channel 98 during rotation in this direction. The processing chamber 18 is intended, during blood processing operations, to be rotated in a counterclockwise direction.

The member 94 includes opposed side edges 99 and 101 that taper inward toward the outward facing channel 98. The tapered side edge 101 further guides the mid region of the umbilicus into engagement with the outward facing channel 98 in response to rotation of the yoke 70 in the counterclockwise direction.

The outward facing guide edge 99 of the channel 98 defines an enlarged curved surface or ramp that extends toward the rotational axis 82. The ramp 99 is sized and configured to accomplish self-loading the umbilicus into the channel 98 when the yoke is rotated in this clockwise direction (as viewed from the top of the rotor plate 84), which is the direction opposite to the direction of rotation intended for regular blood processing (i.e., counterclockwise). The ramp 99 also thereafter keeps the upper portion of the umbilicus 100 from slipping out of the channel 98 when the yoke 70 is rotated in a counterclockwise direction. This, in turn, stabilizes the remainder of the umbilicus for engagement with the channel 96 during rotation in this direction.

The configurations of the channels 96 and 98 thereby complement each other, to keep the mid region of the umbilicus in engagement with the channels 96 and 98 in response to rotation of the yoke 70 and regardless of the direction of rotation of the yoke 70.

In the illustrated embodiment, the channel surfaces 96 and 98 of the support members 92 and 94 are preferably fabricated from a low friction material, to thereby eliminate the need for external lubrication or rotating bearings on the umbilicus 100 itself. The material used can, e.g., comprise Teflon® polytetrafluoroethylene material (DuPont) or an ultra high molecular weight polyethylene. Made from such materials, the channel surfaces 96 and 98 minimize umbilicus drive friction and the presence of particulate matter due to umbilicus wear.

Further details of the support members 92 and 94 can be found in co-pending U.S. patent application Ser. No. 09/976,830, filed Oct. 13, 2001, and entitled "Blood Separation Systems and Methods with Umbilicus Driven Blood Separation Chambers," which is incorporated herein by reference.

Closing the centrifuge station door 20 positions a holding bracket 21 on the underside of the door 20 (see FIG. 5) in registry with the sheath 144. Another holding bracket 23 (as shown in FIG. 5) on the underside of the door 20 is positioned in registry with the fixture 108 when the door 20 is closed. A releasable latch 25 preferably holds the door 20 shut during operation of the centrifuge assembly 68 (as FIG. 6 shows).

During operation of the centrifuge assembly 68, the support members 92 and 94 carry the umbilicus 100 so that rotation of the yoke 70 also rotates the umbilicus 100 in tandem about the axis 82. Constrained within the pocket 90 at its near end (i.e., at the sheath 144) and coupled to the chamber 16 at its far end (i.e., by the mount 218), the umbilicus 100 twists upon the channel surfaces 96 and 98 about its own axis as it rotates about the axis 82, even as the channel surfaces 96 and 98 inhibit radial travel of the umbilicus relative to the rotation axis 82. The twirling of the umbilicus 100 about its axis as it rotates upon the channel surfaces 96 and 98 at one omega with the yoke 70 (typically at a speed of about 2250 RPM) imparts a two omega rotation to the processing chamber 18 secured for rotation on the rotor plate 84.

The relative rotation of the yoke 70 at a one omega rotational speed and the rotor plate 84 at a two omega rotational speed, keeps the umbilicus 100 untwisted, avoiding the need for rotating seals. The illustrated arrangement also allows a single drive motor 80 to impart rotation, through the umbilicus 100, to the mutually rotating yoke 70 and processing chamber 18 carried on the rotor plate 84. Further details of this arrangement are disclosed in Brown et al U.S. Pat. No. 4,120,449, which is incorporated herein by reference.

As before described, the channel surfaces 96 and 98 are desirably formed and oriented in a complementary fashion to accommodate rotation of the umbilicus 100 and the driving of the processing chamber 18 in either clockwise or counter clockwise directions. Thus, the chamber 18 can be rotated in one direction conducive to one desired processing objective, e.g., to accommodate priming and air venting prior to blood processing, and be rotated in an opposite direction conducive to a different processing objective, e.g., blood separation. Furthermore, the close juxtaposition of the umbilicus supports 92 and 94 to the umbilicus 100 when the rotor plate 84 is in the prescribed rotational position to accommodate mounting of the processing chamber 18, and the complementary orientations of the channels 96 and 98 formed in the supports 92 and 94, which lead the near end of the umbilicus toward the support pocket 90, make possible an "easy-load" sequence of intuitive steps, largely capable of being carried out in tandem, for loading the processing chamber 18 for use and unloading the processing chamber 18 after use. The contours and orientations of the channels 96 and 98 aid in "capturing" the umbilicus 100 as a result of rotation of the yoke 70 in either direction, to thereby properly orient the umbilicus 100 on the channel surfaces 96 and 98, even should the operator fail to load the umbilicus 100 entirely correctly in the first instance.

More particularly, the complementary features of the channels 96 and 98 can be advantageously used to self-load the umbilicus 100 for use. Desirably, once the processing chamber 18 is loaded onto the rotor plate 84, and the umbilicus sheath 144 has been placed into the pocket 90, while also initially placing the mid region of the umbilicus 100 into the channels 96 and 98, the yoke 70 can then be initially rotated at a moderate speed (e.g., 300 RPM) in the clockwise direction, which is the direction in which the yoke 70 is rotated during blood processing operations. Rotation in this direction makes use of the elongated ramp 99 to assure that the umbilicus 100 is fully loaded into the channel 98. Thereafter, the yoke 70 can be rotated at the moderate speed in the opposite (counterclockwise) direction, to assure that the position of the umbilicus 100 has been stabilized in both channels 96 and 98 for use. The yoke 70 can then be fully ramped up to a rotational speed in the counterclockwise direction conducive for blood processing.

C. Interface Control by Optical Sensing

Figure 12:
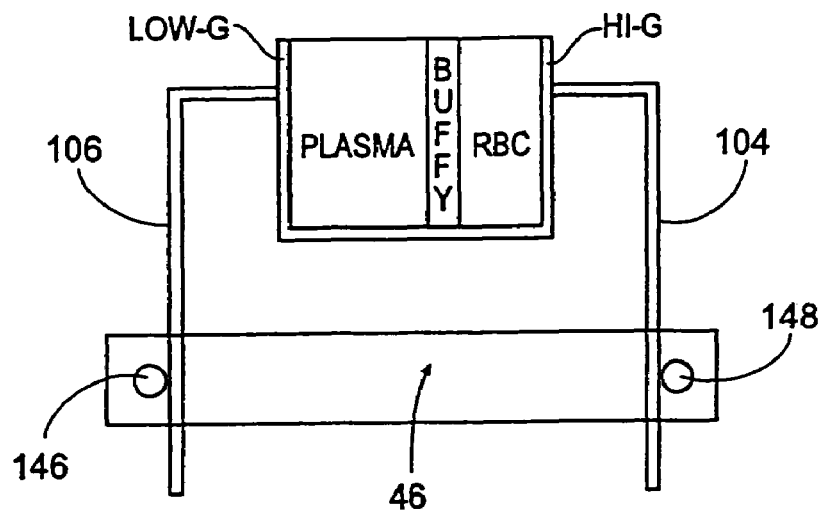
FIG. 12 is a diagrammatic view of the interior of the blood processing chamber of a type shown in FIG. 7, showing the separation of whole blood into a red blood cell layer, a plasma layer, and an intermediate buffy coat layer, with the position of the layers shown in a desired relationship.

In any of the above-described blood processing procedures, the centrifugal forces present within the processing chamber 18 separate whole blood into a region of packed red blood cells and a region of plasma (as diagrammatically shown in FIG. 12. The centrifugal forces cause the region of packed red blood cells to congregate along the outside or high-G wall of the chamber, while the region of plasma is transported to the inside or low-G wall of the chamber.

An intermediate region forms an interface between the red blood cell region and the plasma region. Intermediate density cellular blood species like platelets and leukocytes populate the interface, arranged according to density, with the platelets closer to the plasma layer than the leukocytes. The interface is also called the "buffy coat," because of its cloudy color, compared to the straw color of the plasma region and the red color of the red blood cell region.

It is desirable to monitor the location of the buffy coat, either to keep the buffy coat materials out of the plasma or out of the red blood cells, depending on the procedure, or to collect the cellular contents of the buffy coat. The system includes the optical sensing station 46 (also shown in FIGS. 11A to 11D), which houses two optical sensing assemblies 146 and 148 for this purpose. This arrangement is also diagrammatically shown in FIGS. 12, 13, and 14.

The first sensing assembly 146 in the station 46 optically monitors the passage of blood components through the plasma collection tube 106. The second sensing assembly 148 in the station 46 optically monitors the passage of blood components through the red blood cell collection tube 104.

The tubes 104 and 106 are made from plastic (e.g. polyvinylchloride) material that is transparent to the optical energy used for sensing, at least in the region where the tubes 104 and 106 are to be placed into association with the sensing station 46. The fixture 108 holds the tubes 104 and 106 in viewing alignment with its respective sensing assembly 148 and 146. The fixture 108 also holds the tube 102, which conveys whole blood into the centrifuge station 20, even though no associated sensor is provided. The fixture 108 serves to gather and hold all tubes 102, 104, and 106 that are coupled to the umbilicus 100 in a compact and easily handled bundle.

The first sensing assembly 146 is capable of detecting the presence of optically targeted cellular species or components in the plasma collection tube 106. The components that are optically targeted for detection vary depending upon the procedure.

For a plasma collection procedure, the first sensing assembly 146 detects the presence of platelets in the plasma collection tube 106, so that control measures can be initiated to move the interface between the plasma and platelet cell layer back into the processing chamber. This provides a plasma product that can be essentially platelet-free or at least in which the number of platelets is significantly minimized.

For a red blood cell-only collection procedure, the first sensing assembly 146 detects the interface between the buffy coat and the red blood cell layer, so that control measures can be initiated to move this interface back into the processing chamber. This maximizes the red blood cell yield.

Figure 13:
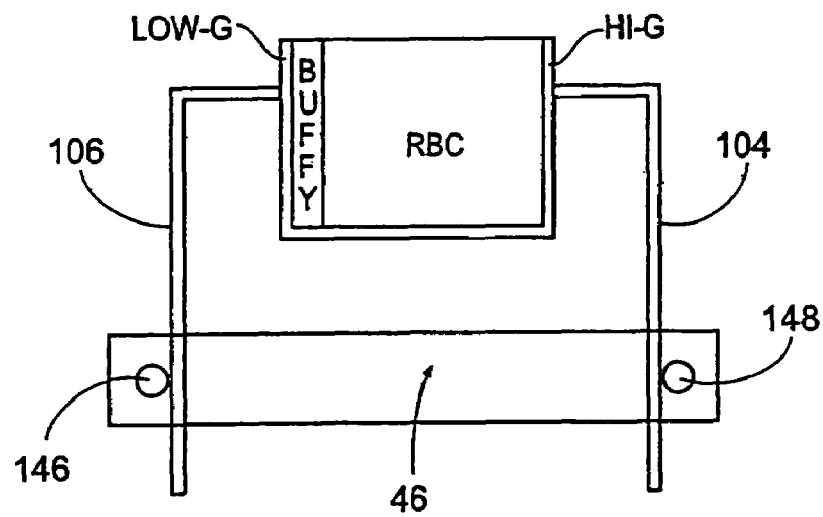
FIG. 13 is a diagrammatic view of the interior of the blood processing chamber of a type shown in FIG. 7, with the buffy coat layer having moved very close to the low-G wall, creating an undesired over spill condition that sweeps buffy coat components into the plasma being collected.

The presence of these cellular components in the plasma, as detected by the first sensing assembly 146, indicates that the interface is close enough to the low-G wall of the processing chamber to allow all or some of these components to be swept into the plasma collection line (see FIG. 13). This condition will also be called an "over spill."

The second sensing assembly 148 is capable of detecting the hematocrit of the red blood cells in the red blood cell collection tube 104. The decrease of red blood hematocrit below a set minimum level during processing that the interface is close enough to the high-G wall of the processing chamber to allow plasma to enter the red blood cell collection tube 104 (see FIG. 14). This condition will also be called an "under spill."

The construction of the sensing station 46 and the first and second sensing assemblies 146 and 148 can vary. In a desired implementation, the first sensing assembly 146 includes a light emitting diode (LED) 400 that can selectively emit either red or green light, and an oppositely facing photodiode 402, for measuring intensity of light transmitted through the plasma tube 106 by the LED 400. The different wavelengths (green and red) of the LED 400 are selected to have generally the same attenuation for platelets but significantly different attenuation for red blood cells. The first sensing assembly 146 can thereby differentiate between the presence of platelets in the plasma flow (to detect an over spill during a plasma collection procedure) and the presence of red blood cells in the plasma flow (to detect the buffy coat interface with red blood cells during a buffy coat collection procedure).

In a desired implementation, the second sensing assembly 148 includes an infrared LED 404 and two photodiodes 406 and 408 one 406 adjacent the infrared LED 404 and the other 408 facing opposite to the infrared LED 404. The photodiode 408 measures light intensity transmitted through the red blood cell tube 104 by the LED 404. The photodiode 406 measures reflected light intensity.

The sensing station 46 and the fixture 108 locate the red blood cell tube 104 in a desired distance relationship to the infrared LED 404 and photodiode 406, which has been observed to result in a linear correlation between measured reflected light intensity and red blood cell hematocrit. As an example, the intensity of reflected light measured at a predetermined radial distance (e.g., 7.5 mm) from an incident light source having a wavelength in the NIR spectrum (e.g., 805 nm) (i.e., LED 404) varies as a linear function with hematocrit for a hematocrit range of at least 10 and 90.

Thus, red blood cell hematocrit can be ascertained by monitored reflected light intensity using the infrared LED 404 and the photodiode 406.

The sensing station 46 can be constructed in various ways. In one implementation, shown in FIGS. 11A to 11D, the station 46 includes a molded body 500 comprising two facing plates 502 and 504. The plates 502 and 504 are spaced apart to receive the fixture 108 and to hold the red blood cell tube 104 and plasma tube 106 in precise alignment with the first and second sensing assemblies 146 and 148.

Each plate 502 and 504 includes an array of light pipes 506 A/B/C and 508 A/B/C that desirably comprise integrally molded components of the body 500. The light pipes 506 A/B/C and 508 A/B/C are in precise optical alignment with the LED's and photodiodes comprising the first and second sensing assemblies 146 and 148. These LED's and photodiodes are carried on circuit boards 510 that are mounted on the exterior of the body 500 facing the light pipes, e.g., using fasteners.

More particularly, the light pipe 506A of the plate 502 is in optical alignment with the photodiode 402 of the first sensing assembly 146. Correspondingly, the oppositely facing light pipe 508A of the plate 504 is in optical alignment with the red/green LED 400 of the first sensing assembly 146.

The light pipe 506B of the plate 502 is in optical alignment with the infrared LED 404 of the second sensing assembly 148. Correspondingly, the oppositely facing light pipe 508B of the plate 504 is in optical alignment with the transmitted light-detecting photodiode 408 of the second sensing assembly 148. The light pipe 506C of the plate 502 is in optical alignment with the reflected light-detecting photodiode 406 of the second sensing assembly 148. In this arrangement, the light pipe 508C of the plate 504 is empty.

Figure 11E:
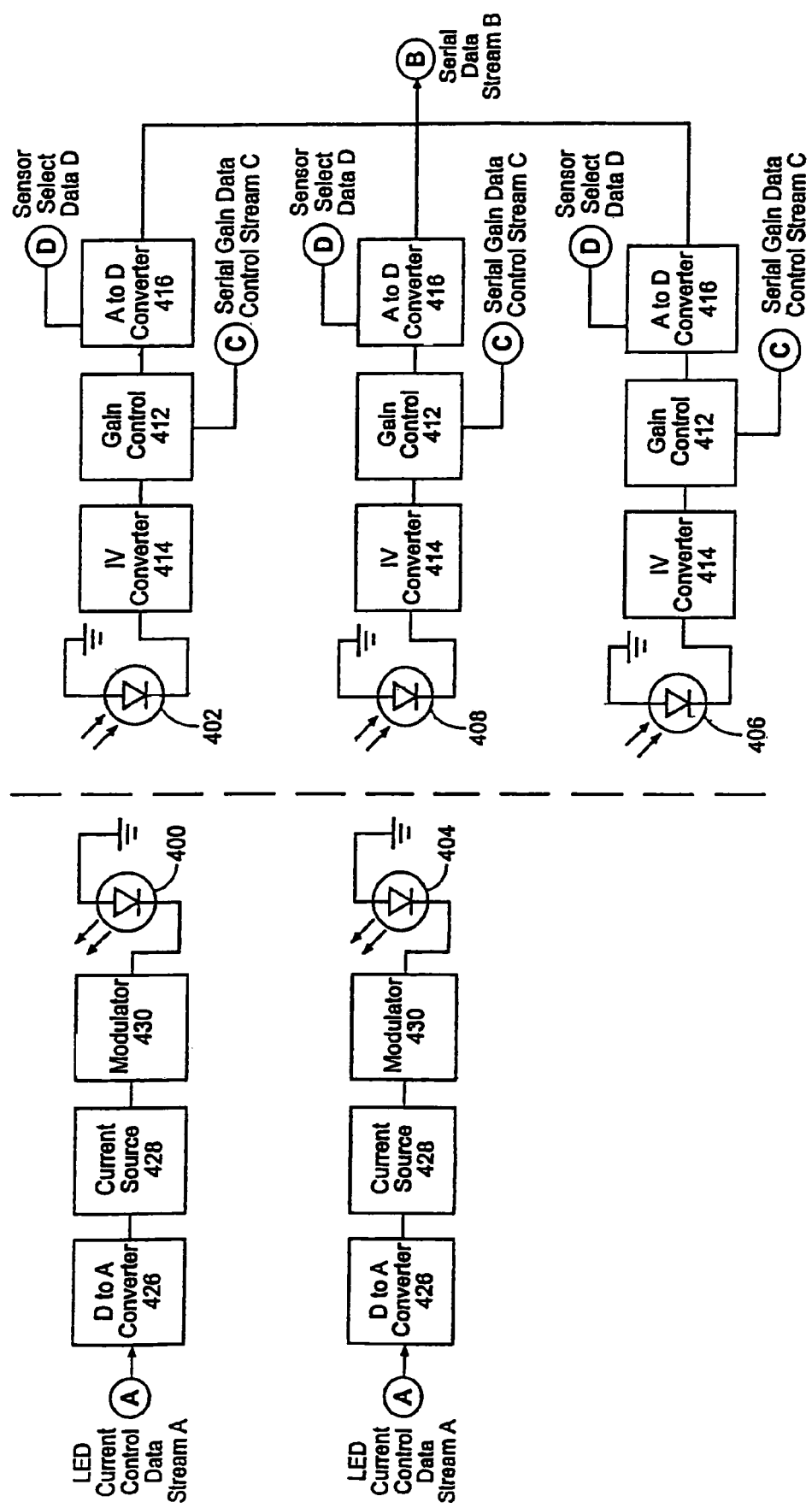
Figure 11F:
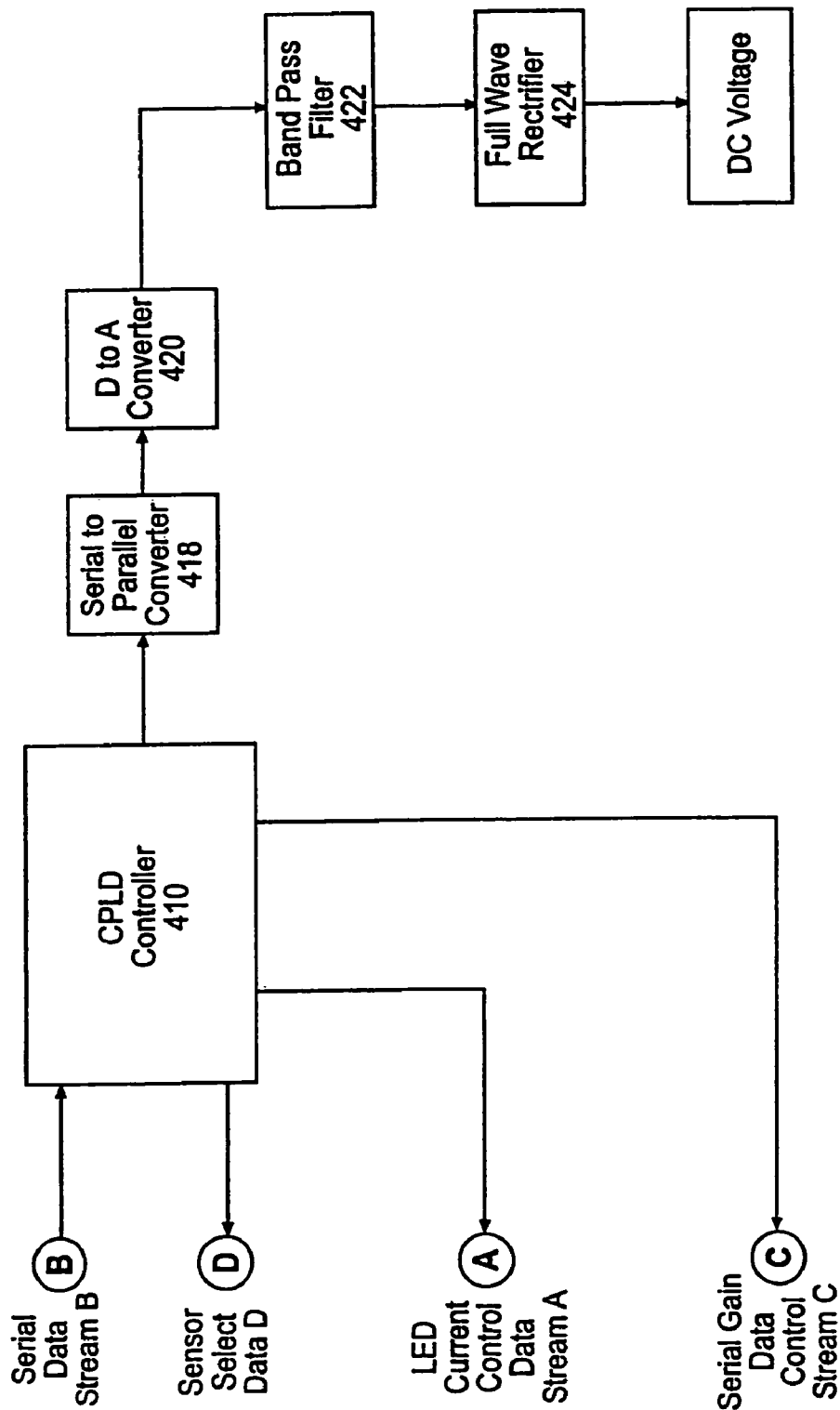

The control circuitry supporting the first and second sensing assemblies 146 and 148 can also vary. In a representative embodiment, (schematically shown in FIGS. 11E and 11F), a CPLD controller 410 (see FIG. 11F) receives a serial data stream (data stream B in FIGS. 11E and 11F) from a selected one of the photodiodes 402, 406, and 408, which is indicative a sensed light intensity (transmitted or reflected, as the case may be) sensed by the selected photodiode. The CPLD controller 410 generates a photodiode selection signal (selection signal C in FIGS. 11E and 11F) to select the photodiode 402, 406, or 408) for data stream receipt.

The CPLD controller 410 controls the gain of gain amplifiers 412 individually associated with each photodiode 402, 406, and 408 (see FIG. 1E), via a digital data stream (data stream C in FIGS. 11E and 11F), which is generated, by a serial output port contained within the controller 410. Each gain amplifier 412 receives a voltage signal from a current-to-voltage converter 414 individually associated with each photodiode 402, 406, 408, which converts the current output of each photodiode 404, 406, and 408 to a voltage. The amplified analog voltage output of each gain amplifier 412 is applied to individual analog-to-digital converters, which converts the analog voltage into the serial data stream for the selected photodiode (data stream B), which the CPLD controller 410 receives for further processing.

The serial data stream B received by the CPDL controller 410 is applied to a serial to parallel port 418 to create a parallel data stream. The original analog voltage from the selected gain amplifier 412 is reconstructed by a digital to analog converter 420 and applied to a bandpass filter 422. The bandpass filter 422 has a center frequency at the carrier frequency of the modulated source light (i.e., 2 KHz in the illustrated embodiment). The output of the bandpass filter 422 (which is sinusoidal) is sent to a full wave rectifier, which transforms the sinusoidal output to a DC output voltage proportional to the sensed light intensity.

A current source 428 is coupled to the LED's 400 and 404. The current source 428 uniformly supplies current to each LED 400 and 404, independent of temperature and the power supply voltage levels. A modulator 430 modulates the constant current at a prescribed frequency. The modulation 430 removes the effects of ambient light and electromagnetic interference (EMI) from the optically sensed reading. In combination with the uniform current source 428, the CPLD controller 410 also adjusts the magnitude of uniform current, and therefore the intensity of each LED 400 and 404. LED current control data is generated in serial form by the controller 410 (serial data stream A in FIGS. 11E and 11F). This serial data is applied to digital-to-analog converters 426, individually associated with each current source 428 for each LED 400 and 404.

The sensing assemblies 146 and 148 are operated by the controller 16, which periodically actuates the sensing assemblies 146 and 148 and samples the sensed intensity outputs. Desirably, a given sensor output used for control purposes comprises an average of multiple samples taken during a prescribed sampling period. For example, during a given sampling period (e.g., every 100 µsec), multiple samples (e.g., 64) are taken. An average of these multiple samples is derived. The variance of the sample average is also desirably determined by conventional methodologies, and the sample average is validated if the variance is less than a prescribed maximum. If the variance of the sample average is equal to or greater than the prescribed maximum, the sample average is not used for control purposes. Desirably, to provide a more dependable output, a running average of the last five validated sample averages is used as the control value. As will be described in greater detail later, the magnitude of the sample variance can also be used as a means for detecting the presence of air bubbles during an air purge conducted at the end of a given blood processing procedure.

Further details of optical sensing arrangements are disclosed in U.S. Pat. No. 6,261,065, which has been incorporated herein by reference.

III. Technical Features of the Pneumatically Actuated Flow Control Components of the System The cassette 28 and the pump and valve station 30 of the system 10 desirably also possess other technical features that support diverse blood processing protocols.

A. The Cassette

In a preferred embodiment (see FIG. 15), the cassette 28 comprises an injection molded body 300 made of a rigid medical grade plastic material. Flexible diaphragms 302 and 304, preferably made of flexible sheets of medical grade plastic, overlay, respectively, the front side and back sides of the cassette 28. The diaphragms 302 and 304 are sealed about their peripheries to the peripheral edges of the front and back sides of the cassette 28.

Figure 15:
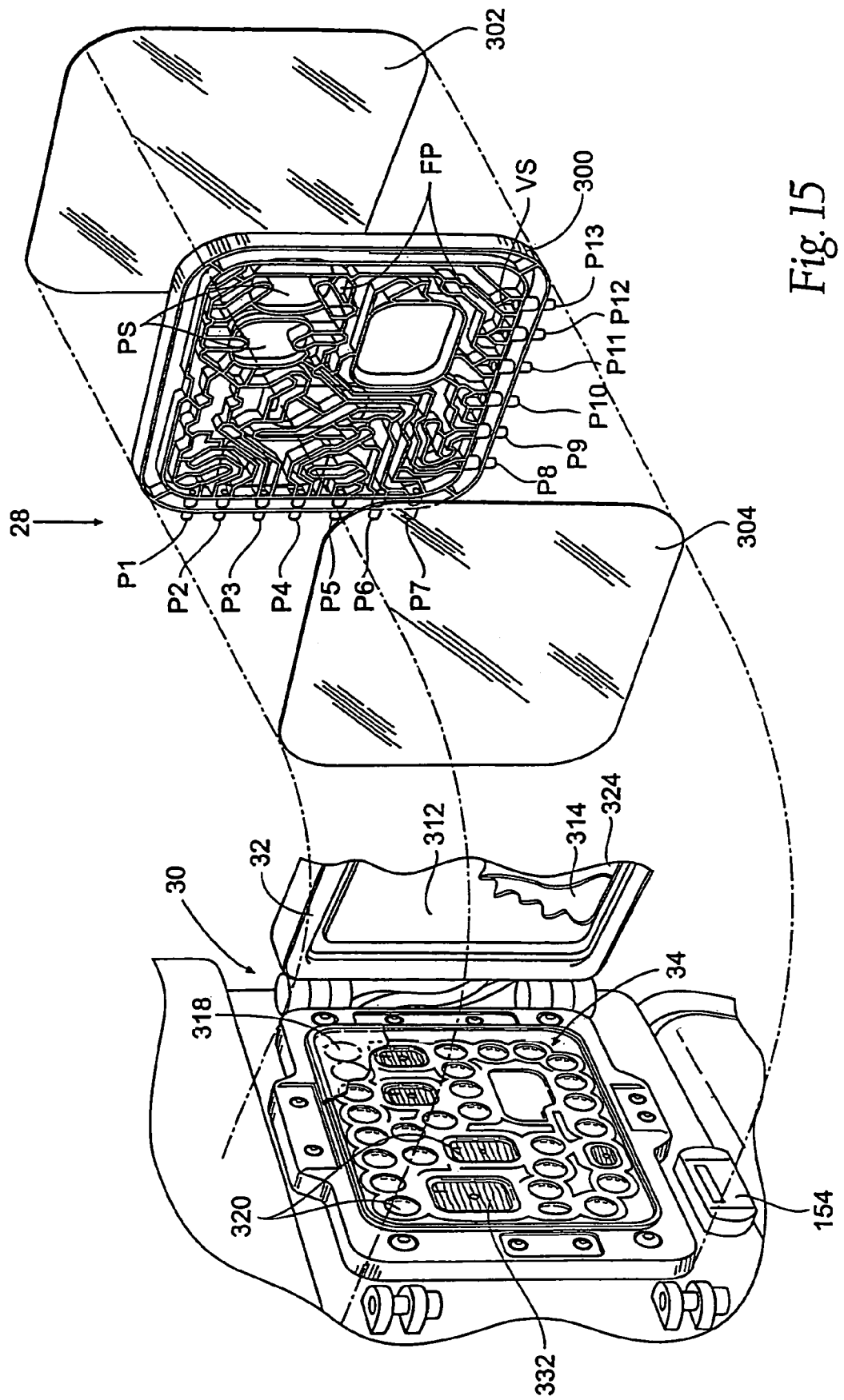
FIG. 15 is an exploded perspective view of the fluid pressure-actuated cassette that forms a part of the liquid and blood flow set shown in FIGS. 5 and 6 and its operative association with the pump and valve station on the device, also shown in FIGS. 5 and 6, which applies positive and negative pneumatic pressure to the cassette to circulate liquid and blood through the cassette.

As FIG. 15 shows, the cassette 28 has an array of interior cavities formed on both the front and back sides. The interior cavities define pneumatic pump stations (schematically designated PS in FIG. 15), which are interconnected by a pattern of fluid flow paths (schematically designated FP in FIG. 15) through an array of in line, pneumatic valve stations (schematically designated VS in FIG. 15).

The layout of the interior cavities can vary according to the different objectives of different blood processing procedures. Desirably, the interior cavities of the cassette 28 define a programmable blood processing circuit 306 (see FIGS. 16 and 17). The programmable circuit 306 can be conditioned by the controller 16 to perform a variety of different blood processing procedures in which, e.g., red blood cells are collected, or plasma is collected, or both plasma and red blood cells are collected, or the buffy coat is collected.

Figure 16:
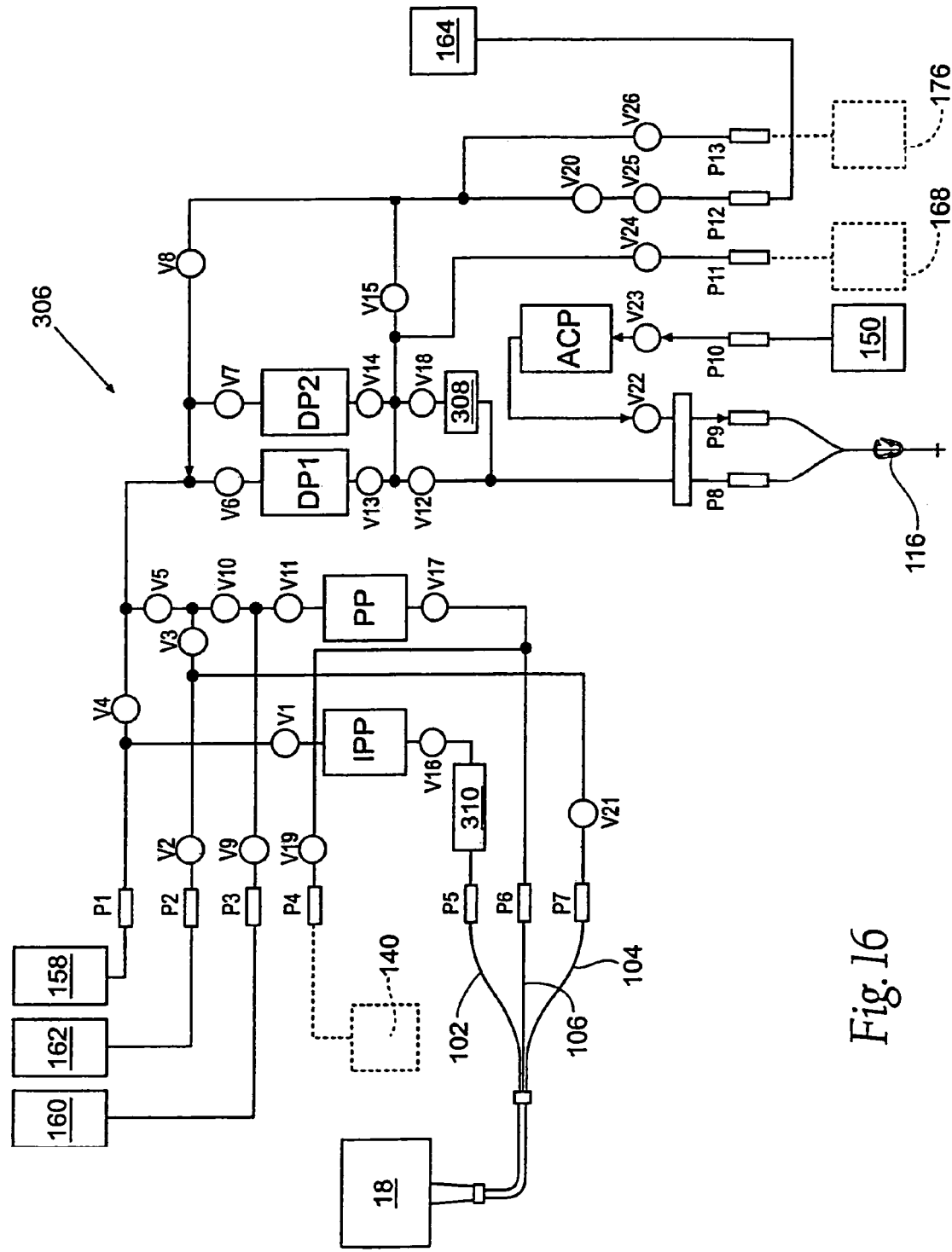
FIG. 16 is a schematic view of a fluid circuit that can be implemented in the cassette shown in FIG. 15 to enable the performance of different blood processing and collection procedures.
Figure 17:
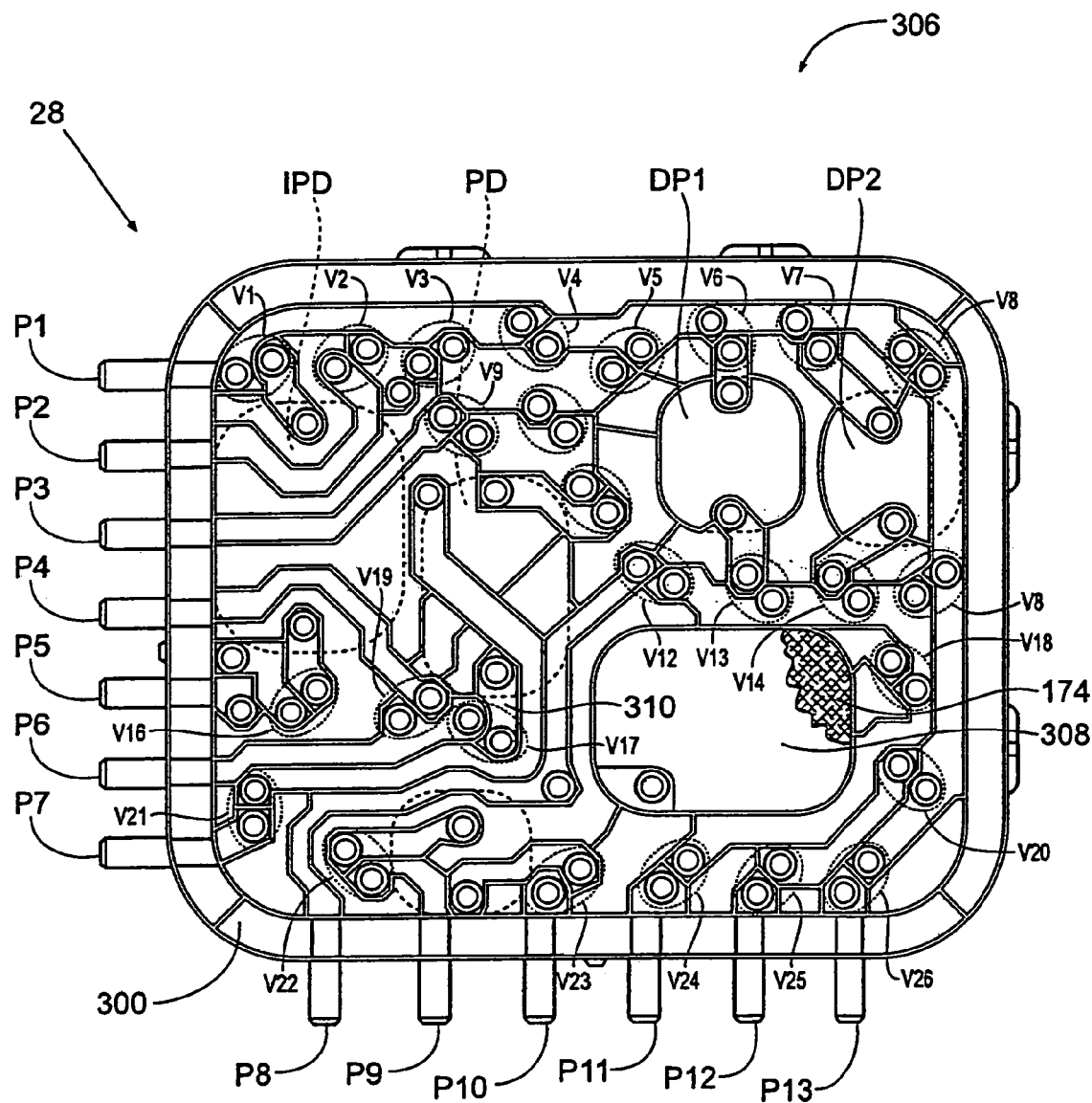
FIG. 17 is a plane view of a cassette in which the fluid circuit shown in FIG. 17 is implemented.

FIG. 16 diagrammatically shows a programmable fluid circuit 306 that can be implemented as an injection molded, pneumatically controlled cassette 28 of the type shown in FIG. 15. FIG. 17 shows the specific implementation of the fluid circuit 306 in the cassette body 300. As will be described, the cassette 28 interacts with the pneumatic pump and valve station 30 to provide a centralized, programmable, integrated platform, capable of performing different blood processing functions.

Figure 23:
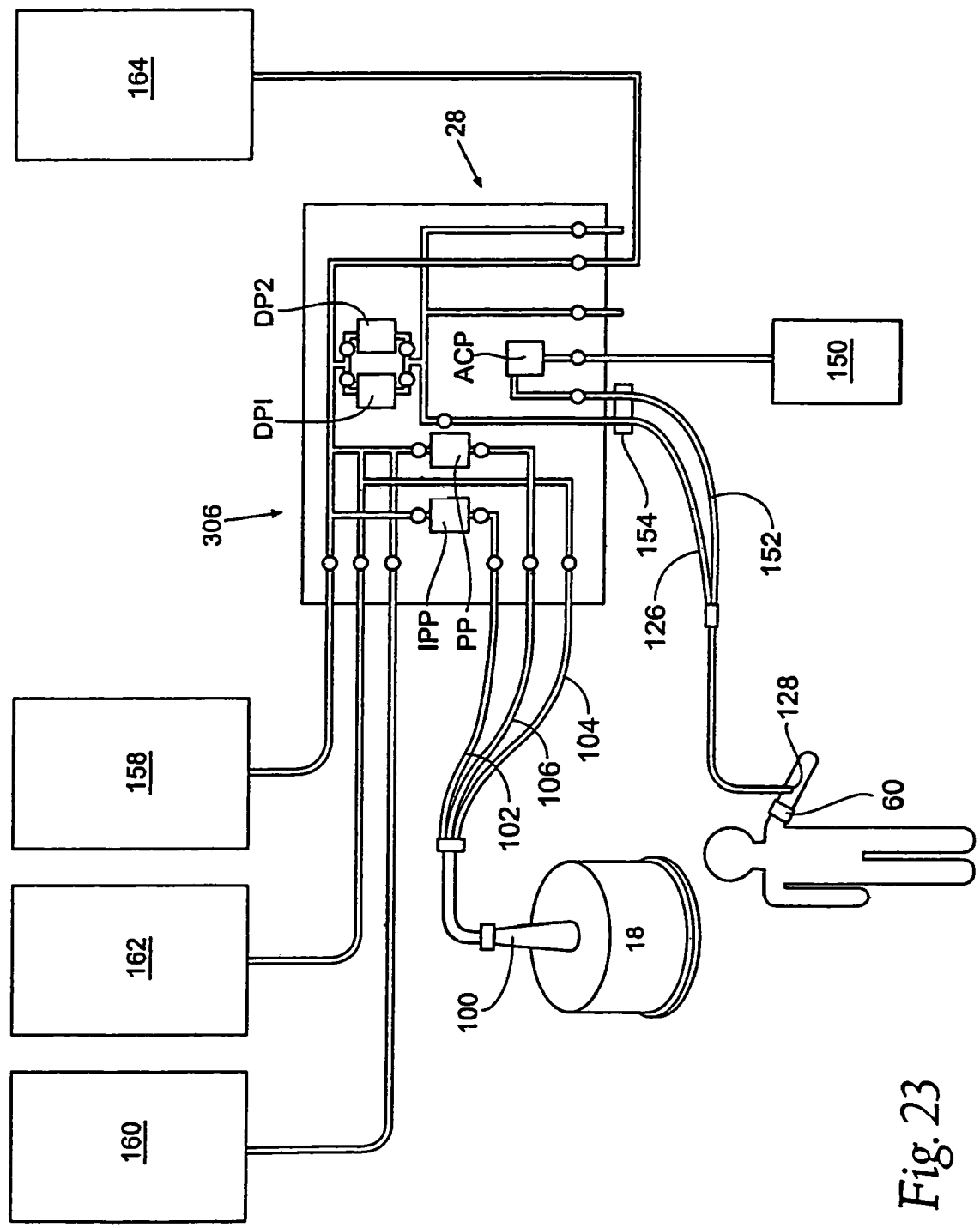
FIG. 23 is a schematic view of a cassette of a type shown in FIGS. 16 and 17 coupled to a liquid and blood flow set in a configuration that can be used for a plasma collection procedure.

The fluid circuit 306 includes dual pneumatic pump chambers DP1 and DP2 (see FIGS. 16 and 23). The pump chambers DP1 and DP2 are desirably operated by the controller 16 in tandem to serve as a general purpose, donor interface pump. The dual donor interface pump chambers DP1 and DP2 work in parallel. One pump chamber draws fluid, while the other pump chamber expels fluid. The dual pump chambers DP1 and DP2 thereby alternate draw and expel functions to provide a uniform outlet flow. The donor tube 126 having the attached phlebotomy needle 128 is coupled to pump chambers DP1 and DP2.

The fluid circuit 306 also desirably includes a pneumatic pump chamber ACP, which serves as a dedicated anticoagulant pump, to draw anticoagulant from an external container 150 and meter the anticoagulant into the blood drawn from the donor through an anticoagulant tube 152, which is coupled to the donor tube 126.

A donor clamp 154 external to the fluid circuit 306 (see also FIGS. 4 and 5) is operated by the controller 16 to close the donor tube 126 and anticoagulant tube 152 when specified conditions occur during blood processing that could affects the comfort or safety of the donor. The donor clamp 154 serves to isolate the donor from the fluid circuit 306 when these conditions occur. The manually operated clamp 116 or a hemostat is also desirably placed downstream of the donor tube-anticoagulant tube 152 junction for added donor safety.

The fluid circuit 306 shown in FIG. 16 also desirably includes a pneumatic pump chamber IPP that serves as a dedicated in-process whole blood pump, to convey whole blood from a reservoir 158 into the processing chamber 18. The dedicated function of the pump chamber IPP frees the donor interface pump chambers DP1 and DP2 from the added function of supplying whole blood to the processing chamber 18. Thus, the in-process whole blood pump chamber IPP can maintain a continuous supply of blood to the processing chamber 18, while the donor interface pump chambers DP1 and DP2 operate in tandem to simultaneously draw and return blood to the donor through the single phlebotomy needle. Processing time is thereby minimized.

The fluid circuit 306 also desirably includes a pneumatic pump chamber PP that serves as a plasma pump, to convey plasma from the processing chamber 18 into a collection container 160. The ability to dedicate separate pumping functions provides a continuous flow of blood into and out of the processing chamber 18, as well as to and from the donor.

The fluid circuit 306 includes an array of valves, designated V1 to V26 in FIG. 16, that connect the pump chambers DP1; DP2, IPP, PP, and ACP to an array of flow paths that transport blood and blood components to and from the donor and to and from the processing chamber. The functions of the valves V1 to V26 are summarized in the following table:

| Valve | Valve Function |
|---|---|
| V1 | Controls fluid flow through flow port 0 of IPP |
| V2 | Controls isolation of an external collection container 162 intended to collect red blood cells during processing |
| V3 | Controls conveyance of red blood cells to the external collection container 162 |
| V4 | Controls conveyance of whole blood to the external in process container 158 |
| V5 | Controls conveyance of red blood cells for return to the donor through the donor tube 126 |
| V6 | Controls fluid conveyance through one an end of DP1 |
| V7 | Controls fluid conveyance through an end of DP2 |
| V8 | Controls conveyance of processing solution (e.g., saline) through ends of DP1 and DP2 from an external solution container 162 |
| V9 | Controls isolation of the external collection container 160 intended to collect plasma during processing |
| V10 | Controls conveyance of plasma for return to the donor through the donor tube 126 |
| V11 | Controls fluid conveyance through an end of PP |
| V12 | Control fluid conveyance to and from donor tube 126 |
| V13 | Controls fluid conveyance through an end of DP1 |
| V14 | Controls fluid conveyance through an end of DP2 |
| V15 | Controls conveyance of processing solution (e.g., saline) through ends of DP1 and DP2 from the external solution container 164 |
| V16 | Controls fluid conveyance through an end of IPP |
| V17 | Controls fluid conveyance through an end of PP |
| V18 | Controls fluid conveyance through a chamber housing a filtration medium, intended to filter blood being returned to the donor through the donor tube 126 |
| V19 | Controls isolation of an external collection container 166 intended to collect buffy coat during processing (if called for by the blood processing protocol) |
| V20 | Controls isolation of the external container 164 holding processing fluid |
| V21 | Controls fluid conveyance of red blood cells through tube 104 from the processing chamber. |
| V22 | Controls fluid conveyance through an end of ACP |
| V23 | Controls fluid conveyance through and end of ACP |
| V24 | Controls isolation of an external container 168 that holds a blood additive solution (if called for by the blood processing protocol) |
| V25 | Controls isolation of the external container 164 holding processing fluid |
| V26 | Controls fluid conveyance to addition external blood collection container(s) 172 (if called for by the blood processing protocol) |

The flexible diaphragms 302 and 304 overlaying the front and back sides of the cassette body 300 rest against upstanding peripheral edges surrounding the pump chambers DP1, DP2, IPP, PP, and ACP; the valves V1 to V26, and array of connecting flow paths. The pre-molded ports P1 to P13 (see FIGS. 16 and 17) extend out along two side edges of the cassette body 300 to couple the fluid circuit 306 within the cassette body 300 to already described external containers and to the donor.

The cassette 28 is vertically mounted for use in the pump and valve station 30, as shown in FIG. 5. In this orientation (see FIG. 15 as well), the diaphragm 302 faces outward toward the door 32 of the valve station 30, ports P8 to P13 face downward, and the ports P1 to P7 are vertically stacked one above the other and face inward.

As will be described, localized application by the pump and valve station 30 of positive and negative fluid pressures upon the backside diaphragm 304 serves to flex the diaphragm 304 to close and open the valve stations V1 to V26 and/or to expel and draw liquid out of the pump chambers DP1, DP2, IPP, PP, and ACP.

As set forth in the above table, an additional interior cavity 308 is provided in the cassette body 300. The cavity 308 forms a station that holds a blood filter material 174 (see FIG. 17) to remove clots and cellular aggregations that can form during blood processing. As shown schematically in FIG. 16, the cavity 308 is placed in the circuit 306 between the port P8 and the donor interface pump stations DP1 and DP2, so that blood returned to the donor passes through the filter 174. The cavity 308 also serves to trap air in the flow path to and from the donor.

Another interior cavity 310 (see FIG. 16) is also provided in the cassette body 300. The cavity 310 is placed in the circuit 306 between the port P5 and the valve V16 of the in-process pumping station IPP. The cavity 310 serves as another air trap within the cassette body 300 in the whole blood flow path serving the separation chamber 18. The cavity 310 also serves as a capacitor to dampen the pulsatile pump strokes of the in-process pump IPP serving the separation chamber 18.

B. Pump and Valve Station

The cassette 28 interacts with a pneumatic actuated pump and valve station 30, which is mounted in the lid of the 40 of the case 36 (see FIG. 15).

The inside face 324 of the door 32 of the pump and valve station 30 (which is desirably metal, as will be explained later) carries an elastomeric gasket 312. The gasket 312 contacts the front side of the cassette body 300 when the door 32 is closed. An inflatable bladder 314 lays between the gasket 312 and the inside face 324 of the door. With the door 32 opened (see FIG. 3), the operator can place the cassette 28 into the pump and valve station 30. Closing the door 32 and securing the latch 316 (shown in FIGS. 3 to 5) brings the gasket 312 into facing contact with the diaphragm 302 on the front side of the cassette body 300. Inflating the bladder 314 presses the gasket 312 into intimate, sealing engagement against the diaphragm 302. The cassette body 300 is thereby secured in a tight, sealing fit within the pump and valve station 30.

The pump and valve station 30 includes a pneumatic manifold assembly 34, which is best shown in FIG. 15. In use, the diaphragm 304 is held by the bladder 314 in intimate engagement against the manifold assembly 34 when the door 32 of the pump station 20 is closed and the bladder 314 is inflated. Desirably, a valve face gasket 318 overlies the pneumatic manifold assembly 34, to serve as a spill shield. FIG. 3 shows the presence of the valve face gasket 318, while, in FIGS. 4 and 15, the valve face gasket 318 has been partially removed to better show the manifold assembly 34.

The manifold assembly 34 includes an array of actuator ports 320 arranged to mirror the array of pump chambers and valves on the cassette 28. Under the control of the controller 16, the manifold assembly 34 selectively distributes the different pressure and vacuum levels to the actuator ports 320, which apply the levels of pressure and vacuum systematically to the pump chambers and valve of the cassette 28 through the diaphragm 304, to route blood and processing liquids in an intended fashion through the fluid circuit 306. Under the control of the controller 16, the manifold assembly 34 also distributes pressure levels to the door bladder 314 (already described), as well as to the donor pressure cuff 60 (see FIG. 23) and to the donor clamp 154 (already described).

The manifold assembly 34 generates Phard, or Hard Pressure, and Pinpr, or In-Process Pressure, which are high positive pressures (e.g., +500 mmHg) applied for closing the cassette valves V1 to V26 and to drive the expression of liquid from the in-process pump IPP and the plasma pump PP. The magnitude of Pinpr is sufficient to overcome a minimum pressure of approximately 300 mm Hg, which is typically present within the processing chamber 18. Pinpr and Phard are operated at the highest pressure to ensure that upstream and downstream valves used in conjunction with pumping are not forced opened by the pressures applied to operate the pumps.

The manifold assembly 34 also generates Pgen, or General Pressure (+300 mmHg), which is applied to drive the expression of liquid from the donor interface pumps DP1 and DP2 and the anticoagulant pump ACP.

The manifold assembly 34 also generates Vhard, or Hard Vacuum (−350 mmHg), which is the deepest vacuum applied in the manifold assembly 34 to open cassette valves V1 to V26. The manifold assembly 34 also generates Vgen, or General Vacuum (−300 mmHg), which is applied to drive the draw function of each of the pumps DP1, DP2, IPP, PP, and ACP. Vgen is required to be less extreme than Vhard, to ensure that pumps DP1, DP2, IPP, PP, and ACP do not overwhelm upstream and downstream cassette valves V1 to V26.

Further details of the operation of the pump and valve station 30 can be found in U.S. Pat. No. 6,261,065, which has been incorporated herein by reference.

C. Capacitive Flow Sensing

The controller 16 desirably includes means for monitoring fluid flow through the pump chambers of the cassette 28. In the illustrated embodiment, the pump and valve station 30 carries small printed circuit board assemblies (PCBA's) 332. One PCBA 332 is associated with each pneumatic actuator port 320 that applies negative and positive pressure to the diaphragm 304 to draw fluid into and expel fluid from the cassette pump chambers DP1; DP2; IPP; PP; and ACP. The PCBA's 332 are each coupled to an electrical source and are each part of a capacitive circuit that is in electrical conductive interaction or contact with fluids within their respective pump chambers. The capacitive circuits comprise capacitors sandwiching each pump chamber. Each PCBA 332 forms one capacitor plate, and the metallic inside face 324 of the door 32 of the pump and valve station 30 forms the other capacitor plate. Between the plates are the pump chambers themselves. Fluid in the pump chambers are shielded from actual physical contact with the circuits by virtue of the cassette diaphragms 302 and 304, the valve face gasket 318 overlying the pneumatic manifold assembly 34, and the gasket 312 overlying the inside face 324 of the door 32. The passage of electrical energy through each PCBA 332 creates an electrical field within the respective pump chamber. Cyclic deflection of the diaphragm 304 associated with a given pump chamber to draw fluid into and expel fluid from the pump chamber changes the electrical field, resulting in a change in total capacitance of the circuit through the PCBA 332.

Capacitance increases as fluid is draw into the pump chamber, and capacitance decreases as fluid is expelled from pump chamber.

In this arrangement, the PCBA's 332 each includes a capacitive sensor (e.g., a Qprox E2S). The capacitive sensor registers changes in capacitance for the circuit 332 for each pump chamber. The capacitance signal for a given circuit 332 has a high signal magnitude when the pump chamber is filled with liquid, has a low signal magnitude signal when the pump chamber is empty of fluid, and has a range of intermediate signal magnitudes when the diaphragm occupies intermediate positions.

At the outset of a blood processing procedure, the controller 16 can calibrate the difference between the high and low signal magnitudes for each sensor to the maximum stroke volume of the respective pump chamber. The controller 16 can then relate the difference between sensed maximum and minimum signal values during subsequent draw and expel cycles to fluid volume drawn and expelled through the pump chamber. The controller 16 can sum the fluid volumes pumped over a sample time period to yield an actual flow rate.

The controller 16 can compare the actual flow rate to a desired flow rate. If a deviance exists, the controller 16 can vary pneumatic pressure pulses delivered to the actuators for the cassette pump chambers to minimize the deviance.

FIG. 15 shows the PCBA's 332 located entirely outside the cassette 28, being face-mounted within the associated actuator port 320. In one alternative embodiment, a component of the circuit 332 (e.g., one of the capacitor plates) can be placed inside the pump chamber of the cassette 28, with the electrical connection to the rest of the circuit routed outside the pump chamber. In another alternative embodiment, the circuit 332 and electrical connections can be implemented on flexible electrode circuits face-mounted on the manifold assembly 34 or as molded circuit board components integrated with the body of the manifold assembly 34. In the latter embodiment, electrical circuitry or routing is molded on thermoplastic parts, e.g., by lithographic patterning, over-molding, or by sealing a flexible circuit to a component part. The thermoplastic parts, which perform electrical functions, are integrated, e.g., by ultrasonic welding, to other components that perform the pneumatic functions of the manifold assembly 34, forming compact, multi-layer, multi-functional assemblies. In this arrangement, electrical connection with the external controller 16 and other external sensors can be achieved, e.g., by female electrical connectors soldered into place to receive electrical pins from the controller 16 and related sensors, and/or by use of consolidated ribbon cables.

IV. Use of System to Perform a Plasma Collection Procedure

Use of a blood flow set 12 in association with the device 14 and controller 16 to conduct a typical plasma collection procedure will now be described.

The plasma collection procedure includes a pre-collection cycle, a collection cycle, and a post-collection cycle. During the pre-collection cycle, the flow set 16 is primed with saline to vent air prior to venipuncture. During the collection cycle, whole blood drawn from the donor is processed to collect plasma, while returning red blood cells to the donor. During the post-collection cycle, excess plasma is returned to the donor, and the set 16 is flushed with air, as will be described in greater detail later.

A. The Blood Processing Chamber

Figure 18:
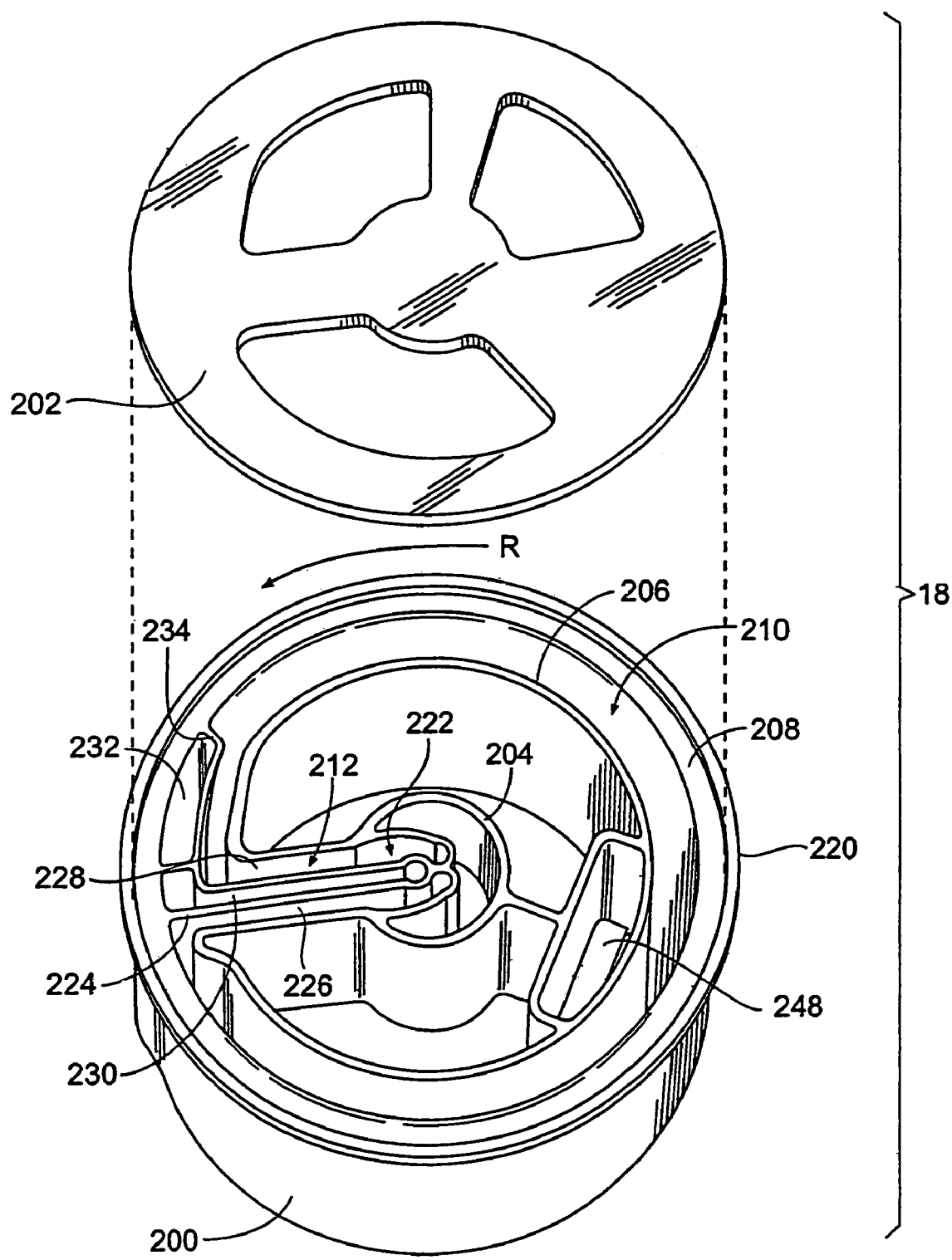
FIG. 18 is a top perspective view of the interior of a representative embodiment of the blood processing chamber of a type shown in FIG. 7, the interior of the chamber being configured to perform a plasma separation and collection procedure using the device shown in FIGS. 5 and 6.

FIG. 18 shows an embodiment of the centrifugal processing chamber 18, which can be used in association with the system 10 shown in FIG. 1 to perform a plasma collection procedure, yielding plasma that is free or essentially free of platelets, red blood cells, and leukocytes. The chamber 18 shown in FIG. 18 can also be used to perform a plasma/red blood cell collection procedure.

Figure 8:
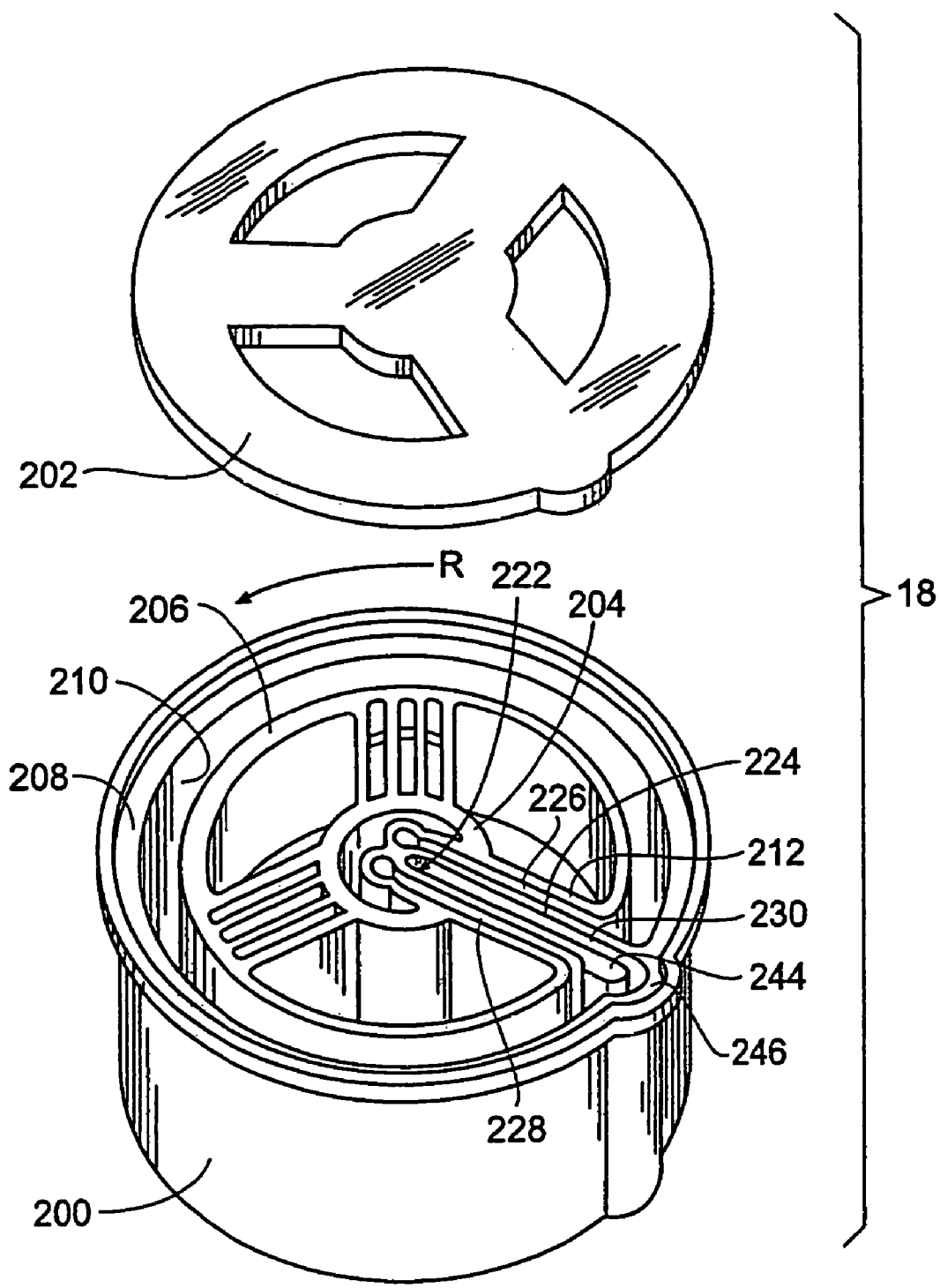
FIG. 8 is a perspective view of the interior of a representative embodiment of the blood processing chamber of a type shown in FIG. 7, the interior of the chamber being configured to perform a red blood cell separation and collection procedure using the device shown in FIGS. 5 and 6.

As previously described with respect to embodiment of a chamber shown in FIG. 8 (with like parts being assigned like reference numerals), the processing chamber 18 is desirably fabricated as separately molded base component 200 and a lid component 202. The molded hub 204 is surrounded radially by inside and outside annular walls 206 and 208 that define a circumferential blood separation channel 210. A molded wall 214 (see FIG. 19) forms an axial boundary of the channel 210. The lid component 202 forms another axial boundary of the channel 210. While both axial boundaries are shown to be generally flat (i.e., normal to the rotational axis), it should be appreciated that the axial boundaries can be tapered, rounded, V-shape, and the like. When assembled, the lid component 202 is secured to the top of the chamber 18, e.g., by use of a cylindrical sonic welding horn.

In the chamber 18 shown in FIG. 18, the inside annular wall 206 is open between one pair of stiffening walls. The opposing stiffening walls form an open interior region 222 in the hub 204, which communicates with the channel 210. Blood and fluids are introduced from the umbilicus 100 into and out of the separation channel 210 through this region 222.

In the embodiment shown in FIG. 18, a molded interior wall 224 is formed inside the region 222 that extends entirely across the channel 210, joining the outside annular wall 208. The wall 224 forms a terminus in the separation channel 210, which interrupts flow circumferentially along the channel 210 during separation.

Additional molded interior walls divide the region 222 into three passages 226, 228, and 230. The passages 226, 228, and 230 extend from the hub 204 and communicate with the channel 210 on opposite sides of the terminus wall 224. Blood and other fluids are directed from the hub 204 into and out of the channel 210 through these passages 226, 228, and 230.

As the processing chamber 18 is rotated (arrow R in FIG. 18), an umbilicus 100 (not shown) conveys whole blood into the channel 210 through the passage 226. The whole blood flows in the channel 210 in the same direction as rotation (which is counterclockwise in FIG. 18). Alternatively, the chamber 18 can be rotated in a direction opposite to the circumferential flow of whole blood, i.e., clockwise, although whole blood flow is the same direction as rotation is believed desirable for optimal blood separation.

The whole blood separates within the chamber 18 as a result of centrifugal forces in the manner shown in FIG. 12. Red blood cells are driven toward the high-G wall 208, while lighter plasma constituent is displaced toward the low-G wall 206. The buffy coat layer resides between the walls 206 and 208.

Circumferentially spaced adjacent the terminus wall 224 nearly 360-degrees from the whole blood inlet passage 226 are the plasma collection passage 228 and the red blood cell collection passage 230. In an upstream flow direction from these collection passages 228 and 230, a barrier 232 projects into the channel 210 from the high-G wall 208. The barrier 232 forms a constriction in the separation channel 210 along the low-G wall 206. In the circumferential flow direction of the blood, the constriction leads to the plasma collection passage 228.

Figure 20:
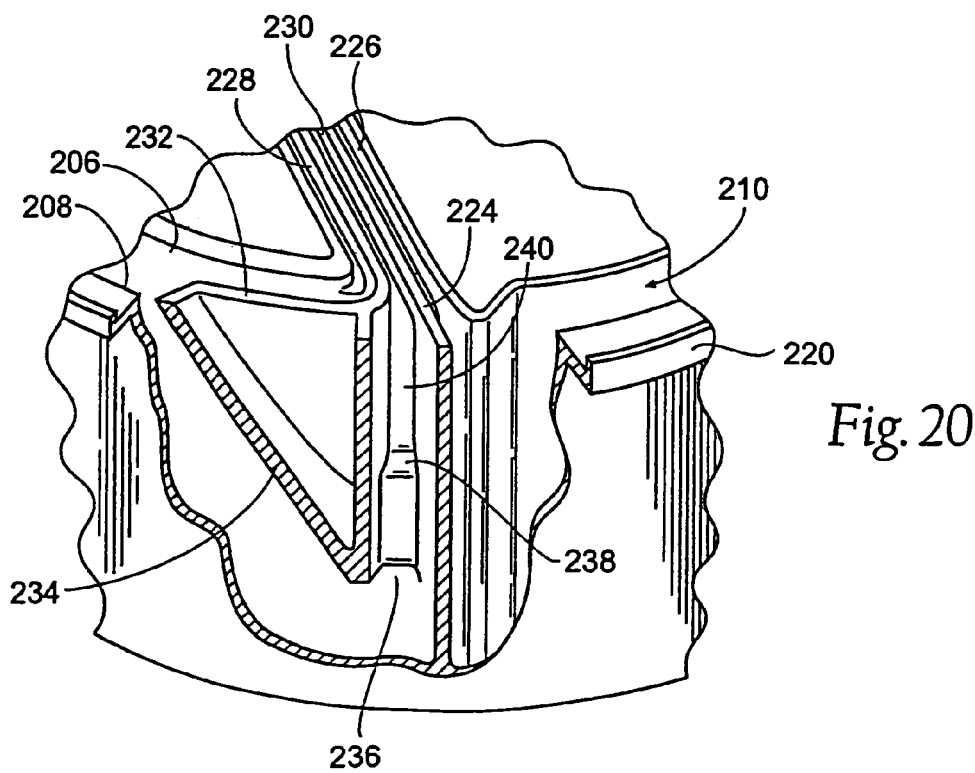
FIG. 20 is an enlarged side perspective view of an interior region in the blood processing chamber shown in FIG. 18, showing a barrier having a tapered surface that directs red blood cells from the separation zone in a path separate from plasma.
Figure 21:
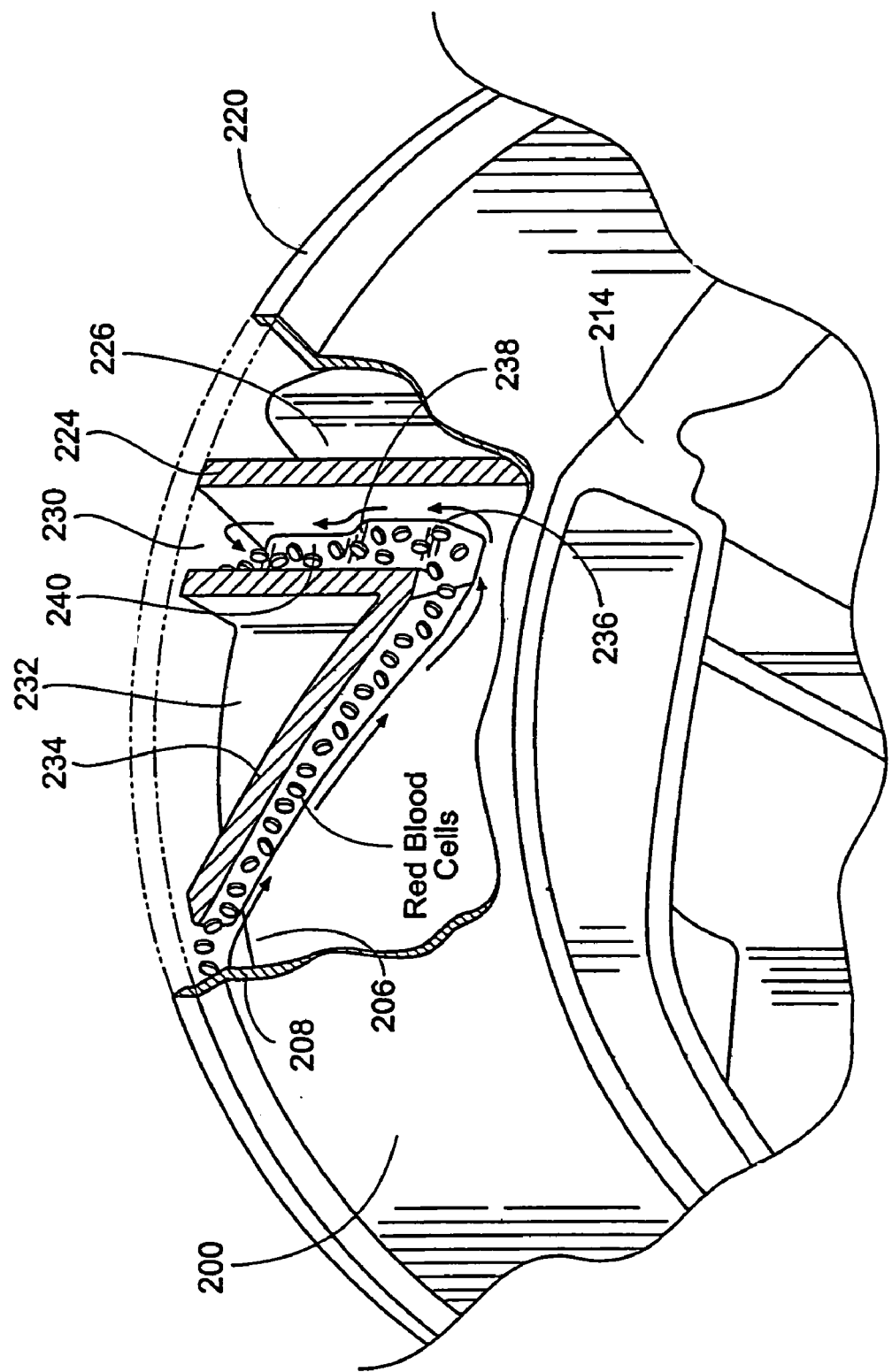
FIG. 21 is an enlarged bottom perspective view of the region shown in FIG. 20, showing the path that red blood cells take as they are directed from the separation zone by the barrier.

As FIGS. 20 and 21 show, the leading edge 234 of the barrier 232 is tapered toward an annular boundary of the channel 210 (which, in the illustrated embodiment, is the annular wall 214) in the direction toward the terminus wall 224. The tapered edge 234 of the barrier 232 leads to an opening 236, which faces the annular boundary of the separation channel 210. The opening 236 faces but is spaced axially away from the annular boundary closely adjacent to the high-G wall 208. The opening 236 communicates with the red blood cell collection passage 230.

A ledge 238 extends an axial distance within the opening 236 radially from the low-G wall 206. The ledge 238 constricts the radial dimension of the opening 236 along the high-G wall 208. Due to the ledge 238, only red blood cells and other higher density components adjacent to the high-G wall 208 communicate with the opening 236. The ledge 238 keeps plasma, which is not adjacent the high-G wall 208, away from communication with the opening 236. Due to the radial restricted opening 236 along the high-G wall 208, the plasma has nowhere to flow except toward the plasma collection passage 228. The plasma exiting the separation channel 210 is thereby free or essentially free of the higher density materials, which exit the separation channel 210 through the restricted high-G opening 236.

The ledge 238 joins an axial surface 240, which is generally aligned with the low-G wall 206. The axial surface 240 extends axially along the axis of rotation to the red blood cell collection passage 230. By virtue of the barrier 232, the ledge 238, and other interior walls, the red blood cell collection passage 230 is isolated from the plasma collection passage 228 (as FIG. 22 shows).

Figure 22:
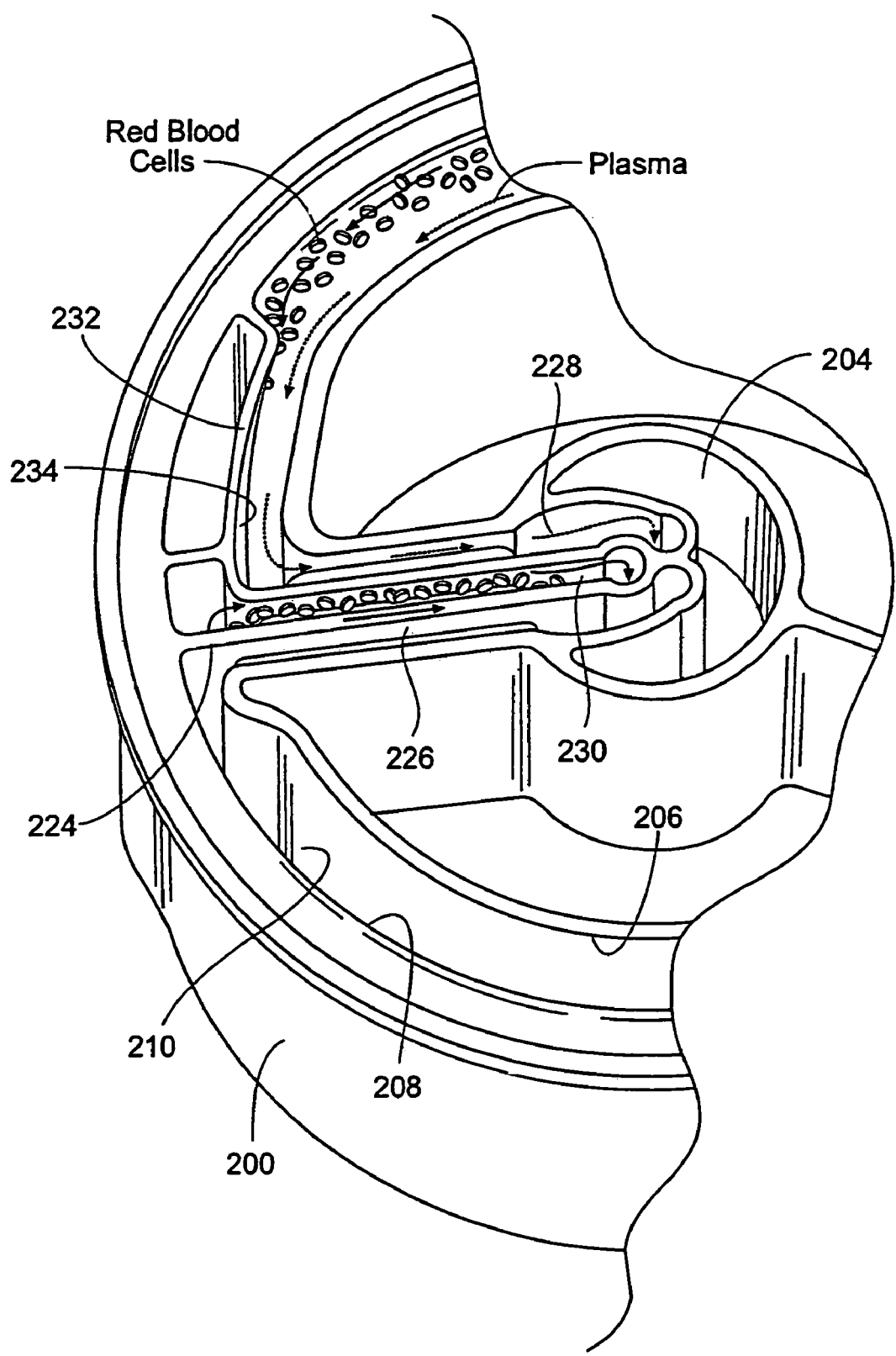
FIG. 22 is an enlarged top perspective view of the region shown in FIG. 20, showing the separate paths that red blood cells and plasma take as they are directed from the separation zone by the barrier.

As FIG. 22 also best shows, plasma residing along the low-G wall 206 is circumferentially directed by the barrier 232 and ledge 238 to the plasma collection passage 228 and into the umbilicus 100. The higher density fluid containing red blood cells and the buffy coat components (platelets and leukocytes), which reside closer to the high-G wall 208, are directed axially along the tapered edge 234 of the barrier 232 toward an annular boundary and the restricted high-G opening 236. From the high-G opening 236, the red blood cells and buffy coat components comprising the higher density fluid are directed over the radial ledge 238 toward the low-G wall 206, and then axially into the red blood cell collection passage 230 and into the umbilicus 100.

The tapered edge 234 that leads the higher density materials axially toward an annular boundary of the separation channel 210 for collection mitigates against abrupt changes in flow directions while the higher and lower density materials are directed toward their respective collection passages 230 and 228. Abrupt changes in flow direction could induce undesired vortex mixing of the buffy coat materials into the plasma. The presence of the radial ledge 238 in the opening 236 also promotes separation of the high density fluid from the plasma, maintaining a desirably high red blood cell hematocrit.

It should be appreciated that the barrier 232 could be configured oppositely relative to the direction of blood flow, so that the tapered edge 234 directs blood along the high-G wall 208 in an axial flow direction upward from a bottom annular boundary wall toward an upper boundary annular wall. In this arrangement, the high-G opening 236 would be located adjacent and axially spaced from the upper annular boundary wall, and the removal of blood could occur from the opposite side of the processing chamber, i.e., the bottom annular wall side. In a radial separation field established between high-G and low-G surfaces, the axial flow direction (either "up" or "down" along the axis of rotation) blood takes along a high-G surface toward an annular boundary is not important to achieving the separation objective; rather, it is the mitigation against abrupt changes in the flow direction while higher and lower density materials separated within the radial field are directed toward their respective collection passages.

The contours, ports, channels, and walls that affect the blood separation process may be preformed in the base component 200 in a single, injection molded operation, during which molding mandrels are inserted and removed through the open end of the base component 200. The lid component 202 comprises a simple flat part that can be easily welded to the open end of the base component 200 to close it after molding. Because all features that affect the separation process are incorporated into one injection molded component, any tolerance differences between the base 200 and the lid 202 will not affect the separation efficiencies of the chamber 18.

If the contours, ports, channels, and walls that are preformed in the base 200 create surfaces that do not readily permit the insertion and removal of molding mandrels through a single end of the base 200, the base 200 can be formed by separate molded parts, either by nesting cup shaped subassemblies or two symmetric halves.

Figure 19:
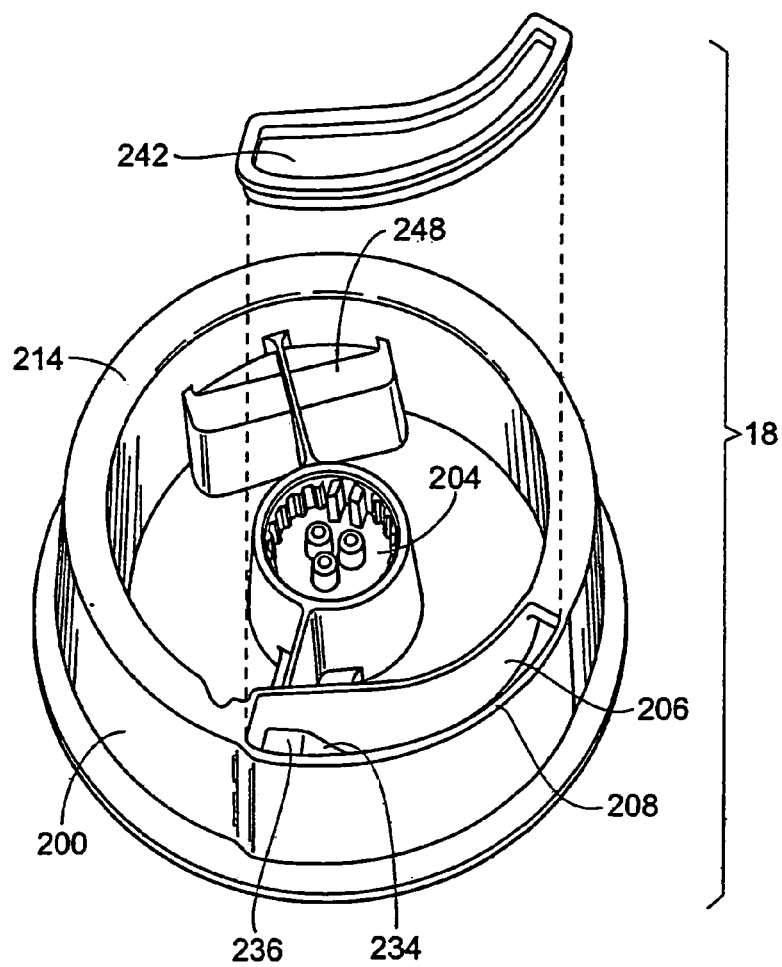
FIG. 19 is a bottom perspective view of the blood processing chamber shown in FIG. 18.

Alternatively, molding mandrels can be inserted and removed from both ends of the base 200. In this arrangement (see FIG. 19), the chamber 18 can be molded in three pieces; namely, the base 200, the lid 202 (which closes one end of the base 200 through which top molding mandrels are inserted and removed), and a separately molded insert 242 (which closes the other end of the base 200 through which bottom molding mandrels are inserted and removed, as shown in FIG. 19.

The chamber 18 can be counterbalanced for rotation in various ways. Interior structures can be molded on one side of the chamber 18 to counterbalance interior structures on the opposite side of the chamber 18. Wall thickness can be varied about the chamber 18 to achieve counterbalancing. Alternatively, as shown in FIG. 18, the chamber 18 can include a molded pocket 248 to carry a suitable counterbalancing weight.

B. The Cassette and Flow Set

FIG. 23 shows the cassette 28 previously described coupled to external processing containers in a configuration that can be used for a plasma collection procedure. For a plasma collection procedure, the containers include a plasma collection container 160, a red blood cell collection container or reservoir 162, a whole blood in process container 158, an anticoagulant container 150, and a processing fluid (e.g., saline) container 164.

1. Plasma Collection Cycle

During a typical collection cycle of the plasma collection procedure, whole blood drawn from the donor is processed to collect plasma, while returning red blood cells to the donor. The donor interface pumps DP1/DP2 in the cassette, the anticoagulant pump ACP in the cassette, the in-process pump IPP in the cassette, and the plasma pump PP in the cassette are pneumatically driven by the controller 16, in conjunction with associated pneumatic valves V1 to V26, to draw anticoagulated blood into the in-process container 158, while conveying the blood from the in-process container 158 into the processing chamber 18 at a controlled rate QWB for separation. This arrangement also removes plasma from the processing chamber 18 into the plasma container 160 at a controlled rate QP, while removing red blood cells from the processing chamber 18 into the red blood cell container 162 (at a rate QRBC=QWB−QP). This phase continues until a targeted volume of plasma is collected in the plasma collection container 160 (as monitored by a weigh sensor) or until a targeted volume of red blood cells is collected in the red blood cell collection container 162 (as also monitored by a weigh sensor).

If the volume of whole blood in the in-process container 158 reaches a predetermined maximum threshold before the targeted volume of either plasma or red blood cells is collected, the controller 16 terminates operation of the donor interface pumps DP1/DP2 to terminate collection of whole blood in the in-process container 158, while still continuing blood separation. If the volume of whole blood reaches a predetermined minimum threshold in the in-process container 158 during blood separation, but before the targeted volume of either plasma or red blood cells is collected, the controller 16 returns to drawing whole blood to thereby allow whole blood to enter the in-process container 158. The controller toggles between these two conditions according to the high and low volume thresholds for the in-process container 158, until the targeted volume of plasma has been collected, or until the target volume of red blood cells has been collected, whichever occurs first.

2. Red Blood Cell Return Cycle

During a typical return cycle (when the targeted volume of plasma has not been collected), the controller 16 operates the donor interface pumps DP1/DP2 within the cassette 28, the in-process pump IPP within the cassette, and the plasma pump PP within the cassette, in conjunction with associated pneumatic valves, to convey anticoagulated whole blood from the in-process container 158 into the processing chamber 18 for separation, while removing plasma into the plasma container 160 and red blood cells into the red blood cell container 162. This arrangement also conveys red blood cells from the red blood cell container 162 to the donor, while also mixing saline from the container 164 in line with the returned red blood cells. The in line mixing of saline with red blood cells raises the saline temperature and improves donor comfort. This phase continues until the red blood cell container 162 is empty, as monitored by the weigh sensor.

If the volume of whole blood in the in-process container 158 reaches a specified low threshold before the red blood cell container 162 empties, the controller 16 terminates operation of the in-process pump IPP to terminate blood separation. The phase continues until the red blood cell container 162 empties.

Upon emptying the red blood cell container 162, the controller 16 operates the donor interface pump station DP1 to draw whole blood from the in process container 158 to fill the donor tube 126, thereby purge red blood cells (mixed with saline) in preparation for another draw whole blood cycle. The controller 16 then conducts another collection cycle. The controller 16 operates in successive collection and return cycles until the weigh sensor indicates that a desired volume of plasma has been collected in the plasma collection container 160. The controller 16 terminates the supply and removal of blood to and from the processing chamber, while operating the donor interface pumps DP1/DP2 in the cassette 28 to convey red blood cells remaining in the red blood cell container 162 to the donor. The controller 16 next enters an air purge cycle, the details of which will be described later.

D. Control of the Interface

During a given plasma collection cycle, the controller 16 desirably operates the sensing station 46, to monitor the presence of targeted cellular blood species components (in particular, platelets or leukocytes, or both) in the plasma collection tube 106. The presence of these cellular components in the plasma, which are detected by the first sensor 146, indicates an over spill condition—i.e., indicating that the interface is close enough to the low-G wall of the processing chamber to allow all or some of these blood species components to be swept into the plasma collection tube 106 (see FIG. 13). This is not desirable, as the objective is to collect plasma free or substantially free of cellular blood components (i.e., a platelet-poor plasma product)

In response to an over spill condition (shown in FIG. 13), the controller 16 operates the in-process pump IPP to draw whole blood from the in-process container 158 into the processing chamber 18 at a predetermined flow rate. Red blood cells continue to exit the chamber 18 through the tube 104 for collection in the collection container 162. However, the controller 16 ceases operation of the plasma pump PP for a preestablished time period (e.g., 20 seconds). This action increases the volume of plasma in the chamber 18 relative to the volume of red blood cells, forcing the interface away from the low-G wall and back toward the middle of the separation chamber (as FIG. 12 shows). After the preestablished time period, the controller 16 resumes operation of the plasma pump PP for a short time period (e.g., 10 seconds), while diverting the plasma to the red blood cell collection container 162 for return to the donor. After this time period, if the spill has been corrected, clean plasma will be detected by the first sensor 146, and normal plasma collection can be resumed. If clean plasma is not sensed, indicating that the over spill has not been corrected, the controller 16 repeats the above-described sequence.

The above-described sequence does not rely upon ascertaining the actual physical position of the interface within the separation chamber, but instead relies upon the measurement resolution for the sensor 146 to discern the presence of cellular components should they move too close to the high-G wall and exit the chamber. When the prescribed maximum allowable platelet contamination is set to a desired low threshold, the platelet contamination threshold can lay below the measurement resolution of the sensor 146. Therefore, a control scheme that relies exclusively upon sensing an over spill condition may not be optimal.

Figure 14:
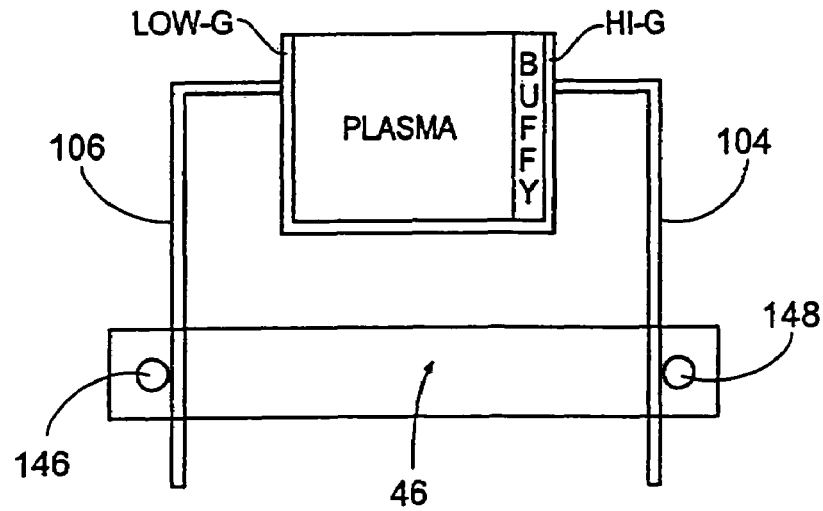
FIG. 14 is a diagrammatic view of the interior of the blood processing chamber of a type shown in FIG. 7, with the buffy coat layer having moved very close to the high-G wall, creating an undesired under spill condition that leads to a reduction of the hematocrit of red blood being collected.

The difference between the flow rate of whole blood entering the separation chamber (QWB) and the flow rate of plasma exiting the separation chamber 18 (QP) determines the flow rate of red blood cells exiting the chamber (QRBC) (i.e., (QRBC=(QWB)–(QP)). (QWB) is typically maintained at a fixed desired rate to optimize processing time, which for a plasma collection procedure generally about 70 ml/min. The ratio (QP)/(QWB) therefore correlates to the physical position of the interface within the separation chamber 18. At a given fixed (QWB), increases in (QP), thereby increasing the ratio, removes a greater volume of plasma and therefore moves' the interface toward the low-G wall (as FIG. 13 shows). Conversely, at a given fixed (QWB), decreases in (QP), thereby decreasing the ratio, removes a lesser volume of plasma and therefore moves the interface toward the high-G wall (as FIG. 14 shows).

The "ideal" ratio (QP)/(QWB) is one that keeps the interface in a desired position within the chamber (as FIG. 12 shows) to avoid an over spill condition in the first instance. However, the "ideal" ratio (QP)/(QWB) is a function of the hematocrit of the donor's whole blood, which cannot be readily controlled or measured during the course of a blood processing procedure.

It has been discovered that the magnitude of the hematocrit of red blood cell exiting the chamber 18 (HCTRBC) can be used to control the physical position of the interface within the separation chamber 18, and thereby minimize or avoid over spill conditions. More particularly, the hematocrit of red blood cells exiting the chamber 18 (HCTRBC) increases with increasing distance between the interface and the high-G wall (i.e., with increases in the ratio (QP)/(QWB)). Conversely, the hematocrit of red blood cell exiting the chamber 18 (HCTRBC) decreases with decreasing distance between the interface and the high-G wall (i.e., with decreases in the ratio (QP)/(QWB)). By adjusting the ratio (QP)/(QWB) to achieve a targeted hematocrit of red blood cells exiting the chamber 18 (HCTRBC), a targeted physical position of the interface relative to the high-G wall can be achieved, without inducing an under spill or over spill condition.

As before described, the sensor 148 for the red blood cell collection tube 104 is desirably adapted and configured to optically detect hematocrit HCTRBC and changes in the hematocrit of red blood cells exiting the processing chamber 18 over time. Alternatively, various conventional means for sensing red blood cell hematocrit can also be used.

An optimal set point for HCTRBC (SET_HCTRBC) can be selected based upon analysis of empirical clinical data generated during system operation, which correlates measured optimal plasma product quality (in terms of platelet, red blood cell, and leukocyte contamination, and, in particular, the absence thereof) and measured optimal collection time. The data demonstrates that, at a determinable high threshold HCTRBC, platelets will cease exiting the chamber 58 with red blood cells. At this given high threshold value HCTRBC, platelets tend to remain with the plasma in the chamber 18, and thereby be subject to mixing with the plasma. Based upon this discovery, SET_HCTRBC is set to approach, but not exceed, this high threshold red blood cell hematocrit value. In a representative implementation, SET_HCTRBC equals about 80±5.

Adjusting the ratio (QP)/(QWB) to achieve (SET_HCTRBC) during a given plasma collection procedure serves to optimize plasma collection parameters for that procedure, as well as mediate against or avoid over spill conditions. Using SET_HCTRBC as a control allows (QP) to be maximized to optimize procedure time and maximize red blood cell hematocrit, while inducing platelets to leave the chamber with the red blood cells to avoid an over spill condition.

In this arrangement, the controller 16 periodically compares sensed HCTRBC (sensed by the sensor 148) to SET_HCTRBC, and adjusts the ratio (QP)/(QWB) to minimize the difference between sensed HCTRBC and SET_HCTRBC. Control based upon SET_HCTRBC keeps the interface in a location within the separation chamber that is empirically determined to optimize plasma purity and collection time, while avoiding or minimizing over spill conditions.

In a representative implementation, the ratio (QP)/(QWB) is desirably set at the outset of a given plasma collection procedure to a value that is somewhat less than an "ideal" (QP)/(QWB). In a representative implementation, the "ideal" (QP)/(QWB) is multiplied by a decrement factor of about 95% to set the initial ratio (QP)/(QWB). In this implementation, the "ideal" (QP)/(QWB) is set equal to (1−Hi/Ho), where Hi is the hematocrit of anticoagulated whole blood entering the separation chamber 18, and Ho is SET_HCTRBC. Hi is derived based upon the actual or estimated hematocrit of the donor (Donor_HCT) and the dilution of the whole blood as a result of addition of anticoagulant. Hi can be derived, e.g., by multiplying Donor_HCT by (1 minus the anticoagulant-to-whole blood ratio/100).

As the procedure progresses, sensed HCTRBC is periodically compared to SET_HCTRBC, and the initial ratio (QP)/(QWB) is incremented or decremented to minimize the difference. Preferably, to avoid an over spill condition, the increments to the ratio (QP)/(QWB) are determined taking into account the difference between sensed HCTRBC and SET_HCTRBC as well as the rate at which the difference is changing. Conventional PID control techniques can be used. Desirably, the ratio (QP)/(QWB) is incremented or decremented within a set minimum and maximum range of values based upon the "ideal" ratio (QP)/(QWB).

Should an over spill be encountered, it is corrected in the manner discussed above and processing then proceeds.

As above described, "ideal" (QP)/(QWB) is a function, at least in part, of the anticoagulated whole blood hematocrit of the donor(Hi). The donor's whole blood hematocrit can be physically measured at the outset of a processing procedure, or be based upon an empirically determined default value (e.g., 0.41 for a female donor and 0.43 for a male donor).

Since the system 10 includes a blood processing chamber 18 of known maximum capacity, the controller 16 can empirically derive the anticoagulated whole blood hematocrit of the donor on line at the outset of a given blood processing procedure.

After venipuncture has been performed and the blood inlet and return pathways primed with whole blood, the controller 16 conditions the centrifuge station 20 to undergo a ramp-up phase. During the ramp-up phase, the processing chamber 18 is accelerated to blood collection velocity. Whole blood is pumped into the separation chamber 18. The red blood cell exit tube is closed, while the plasma exit tube is opened. The controller 16 retains this state until the sensor on the plasma tube detects the presence of red blood cells. This occurrence indicates that the processing chamber 18 has been filled with anticoagulated whole blood. With this occurrence, the controller 16 registers the volume of whole blood that has been conveyed into processing chamber 18. The volume of whole blood required to fill the processing chamber 18 will vary inversely with the donor's anticoagulated whole blood hematocrit. Since the volume of the molded processing chamber 18 is fixed and known, the anticoagulated whole blood hematocrit value for the donor can be directly derived from the measured volume of anticoagulated whole blood required to fill it at the outset of a given processing procedure.

V. Use of the System to Perform a Double Red Blood Cell Collection Procedure

Use of the set 12 in association with the device 14 and controller 16 to conduct a typical double unit red blood cell collection procedure will now be described for illustrative purposes.

A. The Blood Processing Chamber

FIG. 8 shows an embodiment of the centrifugal processing chamber 18, which can be used in association with the system 10 shown in FIG. 1 to perform the intended red blood cell collection procedure. The chamber 18 shares many technical features of the chamber shown in FIG. 18 and previously described, and common reference numerals will be used for this reason. As previously described, the processing chamber 18 is fabricated in two separately molded pieces; namely, the base 200 and the lid 202. The hub 204 is surrounded radially by inside and outside annular walls 206 and 208 that define a circumferential blood separation channel 210. A molded annular wall 214 (see FIG. 7) closes the bottom of the channel 210. The lid 202 closes the top of the channel 210. When assembled, the lid 202 is secured to the top of the chamber 18, e.g., by use of a cylindrical sonic welding horn.

As previously described, the inside annular wall 206 is open between one pair of stiffening walls. The opposing stiffening walls form an open interior region 222 in the hub 204, which communicates with the channel 210. Blood and fluids are introduced from the umbilicus 100 into and out of the separation channel 210 through this region 222. A molded interior wall 224 formed inside the region 222 extends entirely across the channel 210, joining the outside annular wall 208. The wall 224 forms a terminus in the separation channel 210, which interrupts flow circumferentially along the channel 210 during separation.

Additional molded interior walls divide the region 222 into three passages 226, 228, and 230. The passages 226, 228, and 230 extend from the hub 204 and communicate with the channel 210 on opposite sides of the terminus wall 224. Blood and other fluids are directed from the hub 204 into and out of the channel 210 through these passages 226, 228, and 230.

As previously described, the chamber 18 can be counterbalanced for rotation in various ways.

As the processing chamber 18 shown in FIG. 8 is rotated (arrow R in FIG. 8), the umbilicus 100 conveys whole blood into the channel 210 through the passage 226. The whole blood flows in the channel 210 in the same direction as rotation (which is counterclockwise in FIG. 8). Alternatively, the chamber 18 can be rotated in a direction opposite to the circumferential flow of whole blood, i.e., clockwise, although a whole blood flow in the same direction as rotation is believed to be desirable for blood separation efficiencies.

The whole blood separates as a result of centrifugal forces in the manner shown in FIG. 12. Red blood cells are driven toward the high-G wall 208, while lighter plasma constituent is displaced toward the low-G wall 206.

As FIG. 8 shows, a dam 244 projects into the channel 210 toward the high-G wall 208. The dam 244 prevents passage of plasma, while allowing passage of red blood cells into a channel 246 recessed in the high-G wall 208. The channel 246 directs the red blood cells into the umbilicus 100 through the radial passage 230. The plasma constituent is conveyed from the channel 210 through the radial passage 228 into umbilicus 100.

Because the red blood cell exit channel 246 extends outside the high-g wall 208, being spaced further from the rotational axis than the high-g wall, the red blood cell exit channel 246 allows the positioning of the interface between the red blood cells and the buffy coat very close to the high-g wall 208 during blood processing, without spilling the buffy coat into the red blood cell collection passage 230 (creating an over spill condition). The recessed exit channel 246 thereby permits red blood cell yields to be maximized (in a red blood cell collection procedure) or an essentially platelet-free plasma to be collected (in a plasma collection procedure).

As before described, the contours, ports, channels, and walls that affect the blood separation process may be preformed in the base 200 in a single, injection molded operation, during which molding mandrels are inserted and removed through the open end of the base 200. If the contours, ports, channels, and walls that are preformed in the base 200 create surfaces that do not readily permit the insertion and removal of molding mandrels through a single end of the base 200, the base 200 can be formed by separate molded parts, either by nesting cup shaped subassemblies or two symmetric halves, or by removal of molding materials through both ends of the base 200 and use of inserts 242, as FIG. 19 shows.

B. The Cassette

Figure 24:
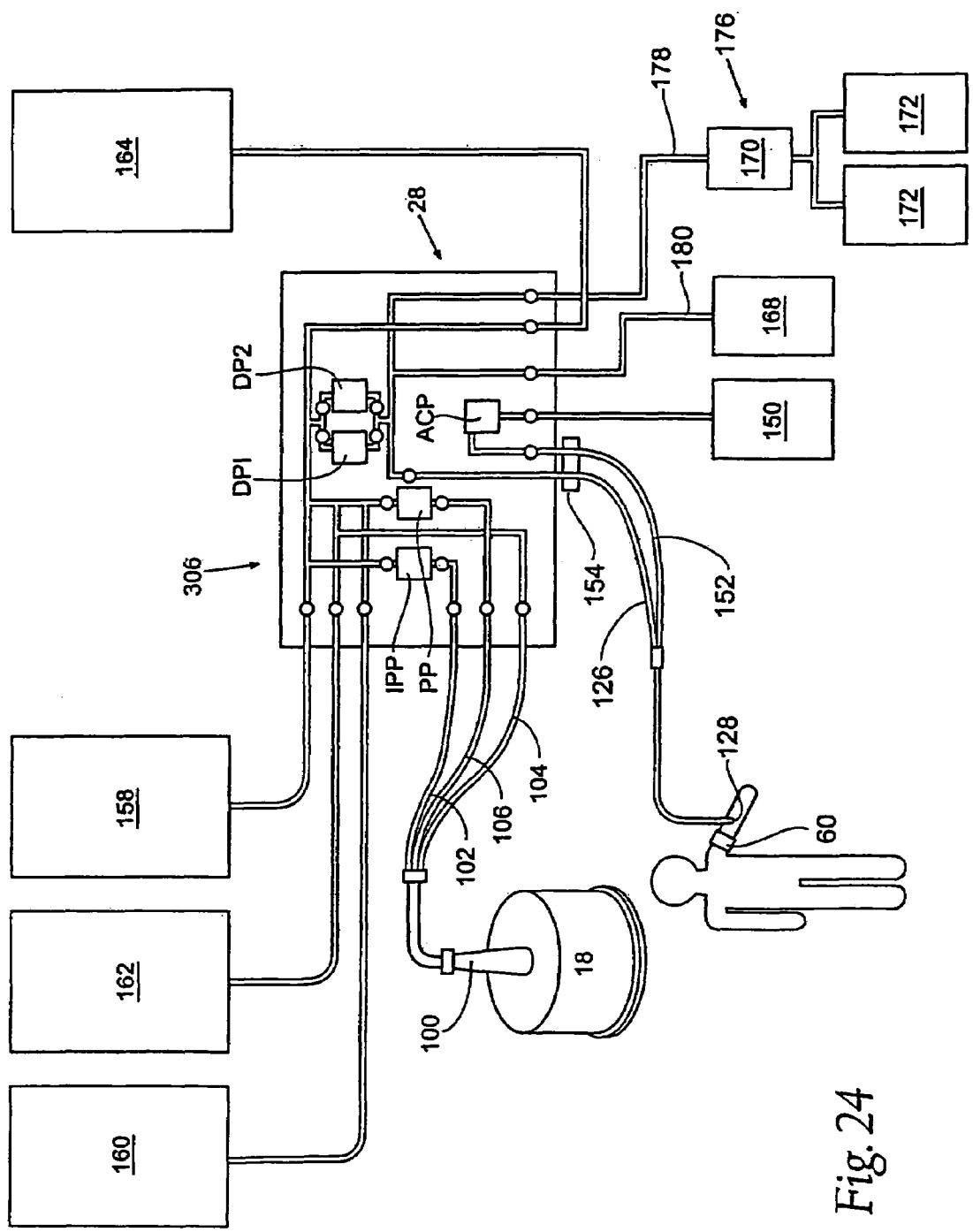
FIG. 24 is a schematic view of a cassette of a type shown in FIGS. 16 and 17 coupled to a liquid and blood flow set in a configuration that can be used for a double unit red blood cell collection procedure, the blood flow set also being shown in FIGS. 5 and 6 after being loaded on the blood processing device.

The interior configuration of pump chambers, valves, and fluid paths for cassette 28 used for the double unit red blood cell procedure is the same as the cassette 28 used for the plasma procedure, and common: reference numbers are used for this reason. FIG. 24 shows the cassette 28 previously described coupled to external processing containers in a configuration that can be used for a double unit red blood cell collection procedure. For a double unit red blood cell collection procedure, the containers include the same array of containers used for the plasma collection procedure; namely, a plasma collection container 160, a red blood cell collection container or reservoir 162, a whole blood in-process container 158, an anticoagulant container 150 and a processing fluid (e.g., saline) container 164. For a double unit red blood cell collection procedure, additional containers are used; namely, a red blood cell additive solution container 168 and a leukocyte reduction collection assembly 176 comprising a leukocyte removal filter 170 and one or more red blood cell storage containers 172 and associated tubing 178. FIGS. 5 and 6 show the mounting of cassette 28 and collection containers shown in FIG. 24 on the device for a double unit red blood cell collection procedure.

1. Collection Cycle

During a typical collection cycle of the double unit red blood cell collection procedure, whole blood drawn from the donor is processed to collect two units of red blood cells, while returning plasma to the donor. The donor interface pumps DP1/DP2 in the cassette, the anticoagulant pump ACP in the cassette, the in-process pump IPP in the cassette, and the plasma pump PP in the cassette are pneumatically driven by the controller 16, in conjunction with associated pneumatic valves, to draw anticoagulated blood into the in-process container 158, while conveying the blood from the in-process container 158 into the processing chamber 18 for separation. This arrangement also removes plasma from the processing chamber into the plasma container 160, while removing red blood cells from the processing chamber into the red blood cell container 162. This phase continues until an incremental volume of plasma is collected in the plasma collection container 160 (as monitored by a weigh sensor) or until a targeted volume of red blood cells is collected in the red blood cell collection container 162 (as monitored by a weigh sensor).

If the volume of whole blood in the in-process container 158 reaches a predetermined maximum threshold before the targeted volume of either plasma or red blood cells is collected, the controller 16 terminates operation of the donor interface pumps DP1/DP2 to terminate collection of whole blood in the in-process container 158, while still continuing blood separation. If the volume of whole blood reaches a predetermined minimum threshold in the in-process container 158 during blood separation, but before the targeted volume of either plasma or red blood cells is collected, the controller 16 returns to drawing whole blood to thereby allow whole blood to enter the in-process container 158. The controller toggles between these two conditions according to the high and low volume thresholds for the in-process container 158, until the requisite volume of plasma has been collected, or until the target volume of red blood cells has been collected, whichever occurs first.

2. Return Cycle

During a typical return cycle (when the targeted volume of red blood cells has not been collected), the controller 16 operates the donor interface pumps DP1/DP2 within the cassette 28, the in-process pump IPP within the cassette, and the plasma pump PP within the cassette, in conjunction with associated pneumatic valves, to convey anticoagulated whole blood from the in-process container 158 into the processing chamber 18 for separation, while removing plasma into the plasma container 160 and red blood cells into the red blood cell container 162. This arrangement also conveys plasma from the plasma container 160 to the donor, while also mixing saline from the container 164 in line with the returned plasma. The in line mixing of saline with plasma raises the saline temperature and improves donor comfort. This phase continues until the plasma container 160 is empty, as monitored by the weigh sensor.

If the volume of whole blood in the in-process container 158 reaches a specified low threshold before the plasma container 160 empties, the controller 16 terminates operation of the in-process pump IPP to terminate blood separation. The phase continues until the plasma container 160 empties.

Upon emptying the plasma container 160, the controller 16 conducts another collection cycle. The controller 16 operates in successive collection and return cycles until the weigh sensor indicates that a desired volume of red blood cells have been collected in the red blood cell collection container 162. The controller 16 terminates the supply and removal of blood to and from the processing chamber, while operating the donor interface pumps DP1/DP2 in the cassette 28 to convey plasma remaining in the plasma container 160 to the donor. The controller 16 next operates the donor interface pumps DP1/DP2 in the cassette to convey the blood contents remaining in the in-process container 158 to the donor as well as convey saline to the donor, until a prescribed replacement volume amount is infused, as monitored by a weigh sensor.

3. Forced Under Spill (Final Red Blood Cell Purge)

In an alternative, embodiment, the controller 16 shortens the overall procedure time by causing a forced under spill of red blood cells from the separation chamber into the red blood cell collection container near the end of the procedure. The deliberately forced under spill purges residual red blood cell volume from the separation chamber at the end of a procedure, thereby simplifying and shortening the time of collection and the final return cycle.

In this embodiment, the controller 16 periodically or constantly monitors the volume of red blood cells remaining to be collected during a given procedure. The controller 16 commences the forced under spill condition when the volume of red blood cells remaining to be collected equals or approximates the volume of red blood cells occupying the separation chamber 18. The volume of red blood cells occupying the separation chamber can be derived based upon (i) the area of the separation chamber 18 (KA) (which is a known quantity based upon geometry of the chamber); (ii) the change in interface position during a red blood cell purge (KI) (which is also a known quantity based on geometry of the chamber); (iii) inlet anticoagulated whole blood hematocrit (Hi), the derivation of which has been previously described, or which can comprise a default value dependent upon gender; (iv) outlet red blood cell hematocrit HCTRBC, the derivation of which has also been previously described; and (v) the absolute volume of red blood cells present in the chamber 18 at the start of the red blood cell purge sequence (KRBC) (which is a constant based upon the geometry of the separation chamber 18). Representative algorithms for deriving the volume of red blood cells occupying the separation chamber based upon the above factors (Forced Under SpillRBC) are:

Forced Under Spill$RBC=(KRBC)+\Delta IP*HCTRBC$ where: $\Delta IP$ is the in process blood volume needed to achieve the under spill $(KI)/[(1-(Hi))/HCTRBC/(KA)]$ During the forced under spill, the red blood cell collection tube 104 is closed and the plasma collection tube 106 is opened. In this state, the platelet and leukocyte layer of the interface is conveyed from the chamber 18 along with the plasma for return to the donor. This reduces leukocyte contamination of the red blood cells. When the controller 16 detects that red blood cells have entered the plasma collection tube 106 (which the sensor 146 will detect), the controller closes the plasma collection tube and opens the red blood cell collection tube. This state allows the red blood cells that have accumulated in the separation chamber to be conveyed to the red blood cell collection container. Typically, the blood cell collection target is achieved during this state. If that target is not reached, the controller 16 reverts to a normal red blood cell collection state.

Upon completion of a red blood cell collection procedure, the controller 16 enters an air purge cycle, the details of which will be described later.

4. Leukofiltration

When the collection of red blood cells and the return of plasma and residual blood components have been completed, the controller 16 can switch, either automatically or after prompting the operator, to an in-line leukofiltration cycle. During this cycle, red blood cells are removed from the red blood cell collection reservoir 162 and conveyed into the red blood cell storage containers 172 through the leukocyte removal filter 170. At the same time, a desired volume of red blood cell storage solution from the container 168 is mixed with the red blood cells.

The leukofilter 170 can be variously constructed. The filter can, e.g., comprise a housing inclosing a filtration medium that can comprise a membrane or be made from a fibrous material, such as melt blown or spun bonded synthetic fibers (e.g., nylon or polyester or polypropylene), semi-synthetic fibers, regenerated fibers, or inorganic fibers. If fibrous, the medium removes leukocytes by depth filtration. If a membrane, the medium removes leukocytes by exclusion. The housing can comprise rigid plastic plates sealed about their peripheries. Alternatively, the housing can comprise flexible sheets of medical grade plastic material, such as polyvinyl chloride plasticized with di-2-ethylhexyl-phthalate (PVC-DEHP). The filter 170 can be held during use in a retaining fixture 182 on the base of the device.

In the first stage of the leukofiltration cycle, the controller 16 operates donor interface pumps DP1/DP2 in the cassette to draw air from the red blood cell storage containers 172, the filter 170, and the tubing 178, and to transfer this air into the red blood cell collection reservoir 162. This stage minimizes the volume of air residing in the red blood cell storage containers 172 before the leukocyte removal process begins. The stage also provides a volume of air in the red blood cell collection container 162 that can be used purge red blood cells from the filter 170 into the red blood cell collection containers 172 once the leukocyte removal process is completed.

In the next stage, the controller 16 operates the donor interface pumps DP1/DP2 in the cassette 28 to draw a priming volume of storage solution from the solution container 168 into the red blood cell collection reservoir 162. This stage primes the tubing 180 between the container 168 and the cassette 28, to minimize the volume of air pumped into the final red blood cell storage containers 172.

In the next stage, the controller 16 operates the donor interface pumps DP1/DP2 in the cassette 28 to alternate pumping red blood cells from the red blood cell collection reservoir 162 into the red blood cell collection containers 172 (through the filter 170), with pumping of red blood cell storage solution from the container 168 into the red blood cell collection containers 172 (also through the filter 170). This alternating process mixes the storage solution with the red blood cells. The controller 16 counts the pneumatic pump strokes for red blood cells and the storage solution to obtain a desired ratio of red cell volume to storage solution volume (e.g., five pump strokes for red blood cells, followed by two pump strokes for storage solution, and repeating the alternating sequence). This alternating supply of red blood cells and storage solution continues until the weigh scale for the red blood cell collection reservoir 162 indicates that the reservoir 162 is empty.

When the red blood cell collection reservoir 162 is empty, the controller 16 operates the donor interface pumps DP1/DP2 to pump a predetermined volume of air from the red blood cell collection reservoir 162 through the filter 170. The volume of air is predetermined based upon the volume of air that was drawn into the red blood cell collection reservoir 308 before the leukocyte removal process began. The air serves to purge red blood cells from the filter 170, to minimize the presence of residual red blood cells in the tubing, cassette 28, and filter 170. This step also assures that the red blood cell collection reservoir 162 is completely empty.

The controller 16 next pumps additional storage solution through the filter 170 and into the red blood storage containers 172, as required to ensure that a desired ratio between storage solution volume and red blood cell volume exists. Then, as a final step, the controller 16 pumps a last, predetermined volume of storage solution through the filter 170 to rinse any still-remnant red blood cells from the filter 170 and into the storage containers 172. This final step maximizes post-filtration percent red blood cell recovery. The controller 16 desirably waits a predetermined time period (e.g., 20 seconds) to allow the filter 170 to complete draining.

Further details of the leukofiltration cycle and the leukofiltration filter 170 can be found in Co-Pending U.S. patent application Ser. No. 09/976,832, filed Oct. 13, 2001, and entitled "Blood Separation Systems and Methods that Alternate Flow of Blood Component and Additive Solution through an In-Line Leukofilter," which is incorporated herein by reference.

VI. Air Purge

At the end of a given blood collection procedure, the chamber 18 will contain residual volumes of red blood cells and plasma. It is desirable to return these residual volumes of blood components to the donor. This is particularly true in the case of red blood cells. The ability to return as many red blood cells as possible minimizes donor red blood cell loss and shortens the subsequent deferral period, during which collection of red blood cell from the donor is not permitted.

It has been discovered that the most efficient way to flush red blood cells from the separation chamber for return to the donor is by sending sterile air through the separation chamber. The use of sterile air, instead of a liquid, to flush red blood cells from the separation chamber after blood processing also lessens the weight of potentially bio-hazardous wastes that must be disposed of after blood processing.

Sterile air is purged from the system and parked in the in-process whole blood reservoir during the initial priming cycle, prior to a given blood processing procedure. This becomes the source of sterile air to subsequently flush red blood cells from the separation chamber after completion of the blood processing procedure.

During a first phase of the air flush, the red blood cell collection tube 104 is closed. Air is pumped through the whole blood inlet tube 102 into the separation chamber 18 while residual red blood cells are drawn by operation of the plasma pump PP through the plasma outlet tube 106 from the chamber 18. This phase continues until air is detected in the plasma tube 106. A second phase of the air flush then commences.

During the second phase, the plasma outlet tube 106 is closed, and the red blood cell tube 104 is opened. The separation chamber 18 is ramped into rotation to achieve a relatively modest rotational rate (e.g., 300 RPM), sufficient to displace red blood cells toward the high-G wall of the chamber 18 for removal, and to displace air residing in the separation chamber 18 toward the low-G wall of the separation chamber 18. The second phase continues until air is detected in the red blood cell tube 104. At this point, the air flush is terminated.

The detection of air in the red blood cell tube 104 and the plasma tube 106 can be accomplished using a conventional ultrasonic air detector. However, it has been discovered that the same sensors 146 and 148 used for optically detecting cellular components in the plasma and red blood cell tubes 106 and 104 can also be used to detect the presence of air in these tubes 106 and 104.

As previously described, the sensor 146 in the plasma tube 106 uses red and green light transmission to determine the concentrations of platelets and/or red blood cells in plasma exiting the chamber 18. The sensor 148 in the red blood cell tube 104 uses infrared (805 nm) reflectance and transmission to determine the hematocrit of red blood cells exiting the separation chamber 18. The sensors 146 and 148 are operated by the controller 16, which periodically actuates the sensors 146 and 148 and samples the outputs. A given sensor output is the average of multiple samples.

It is been determined that the present of air bubbles passing by either sensor 146 or 148 creates a pronounced variance among the measurement samples taken by the sensor, which significantly exceeds the variance used to validate sample averages during normal operation. A set threshold variance among samples taken during a sample period can be correlated to the presence of air during the air flush cycle. The variance of multiple samples taken during a given sampling period can be determined, e.g., by summing the difference between each sample and the sample average, squaring the sum of the differences, and dividing this quantity by the number of samples minus one.

In the case of the plasma line sensor 146, if the variance for either red or green transmittance measurements exceeds a threshold variance of about 4000 (which is greater than the variance by which the validity of samples are gauged for normal interface sensing purposes), the controller 16 generates an air bubble detection signal for the plasma tube 106. The controller 16 shifts from first phase to the second phase of the air flush protocol.

In the case of the red blood cell line sensor 148, if the variance of either infrared transmittance or infrared reflectance measurements exceeds a threshold variance of about 2000 (which is also greater than the variance by which the validity of samples are gauged for normal interface sensing purposes), the controller 16 generates an air bubble detection signal for the red blood cell tube 104. The controller 16 terminates the second phase of the air flush protocol.

VII. Cassette Integrity Checks

Installation of the blood flow set 12 involves correct placement of the cassette 28 in the pump and valve station 30, correct routing of the donor tube 126 and anticoagulant tube 152 through the donor clamp 154, and the correct placement of a clamp 116 or a hemostat downstream of the donor tube-anticoagulant tube 152 junction. The correct placement of the cassette, correct routing of these tubes 126 and 152 through the donor clamp 154, and the presence of a clamp 116 or a hemostat is desirably checked in every procedure prior to connecting the donor to the flow set.

A pneumatic seal between cassette diaphragm 304 and the pneumatic manifold assembly 34 is necessary to ensure proper functioning of fluid pressure-actuated valves and pumps, as well as the integrity of the fluid flow channels within the cassette. In addition to a pneumatic seal, the amount of trapped air between cassette diaphragm 304 and valve face gasket 318 of the pneumatic manifold assembly 34 should be minimized for effective operation of fluid valves and pumps. Inflation of the door bladder 314 prior to complete installation of cassette 28 against the manifold assembly 34 can compromise sealing. Defects in cassette sealing surfaces, like knicks and dings, as well as improper loading of cassette 28 in the cassette holder 26 can also compromise sealing. These conditions also are desirably detected prior to connecting the donor to the flow set 12.

For these reasons, the controller 16 desirably undertakes a series of cassette installation and integrity checks. In a representative implementation, these installation and integrity checks include (1) a cassette presence check, which verifies the presence of cassette 28 in the pump and valve station 30 prior to inflation of door bladder 314; (2) a burp routine to minimize trapped air between cassette diaphragm 304 and valve face gasket 318; (3) a valve cross-talk check, which verifies proper seating of cassette 28 against the manifold assembly 34 and the lack of leaks in the valve face gasket 318; (4) a dry cassette integrity test, which verifies—using air—the correct routing of the donor tube 126 and the anticoagulant tube 152 through donor clamp 154; and (5) a wet cassette integrity test, which verifies—using a liquid (e.g., saline)—the absence of cassette defects which could compromise sealing of valves and integrity of fluid channels.

A. Cassette Presence Check

This test verifies that a cassette 28 is installed and the door 32 of the pump and valve station 30 is closed prior to connecting a donor and starting a desired blood processing session.

With reference to FIG. 15, the operator installs the cassette 28 in the pump and valve station 30 and closes the station door 32. If the cassette 28 is present, the available volume for expansion of door bladder 314 is reduced. Therefore, the time required to reach a given pressure level is reduced. This property is used during the cassette presence check to verify the presence of cassette 28 in the pump and valve station 30.

The controller 16 directs the manifold assembly 34 to apply vacuum to open all cassette valves and pumps. The controller 16 then directs the manifold assembly 34 to apply pneumatic pressure to the door bladder 314. The controller 16 registers the build-up of pressure in the bladder 314, while also tracking elapsed time. If the pressure in the bladder 314 equals or exceeds a prescribed threshold pressure (PBLAD) (e.g., 800 mmHg) within a prescribed time period (e.g., 30 seconds), the controller 18 deems that the cassette 28 is present within the station. Otherwise, the controller 16 alarms and prompts the operator to load the cassette 28.

Once the presence of the cassette 28 is verified, the controller 18 proceeds to the next integrity test, which is the burp routine.

B. Burp Routine

The burp routine minimizes the amount of air trapped between valve face gasket 318 and cassette diaphragm 304, after the door 32 has been closed (in general, see FIG. 15). Trapped air can adversely affect the performance of valves and pumps in the cassette 28.

The controller 16 invokes the burp routine after the presence of the cassette 28 has been verified. During the burp routine, the door bladder 314 is inflated to a prescribed lesser pressure level (e.g., less than about 800 mmHg), which seats the cassette 28 against the manifold assembly 34, but does not cause a pneumatic seal with the valve face gasket 318. While the door bladder 314 is at this lesser pressure, the controller 16 then directs the manifold assembly 34 to regulate PHARD and then PGEN for prescribed time periods. This regulation of different pressures against the valve face gasket 318 causes the valve face gasket 318 to puff. This action will expel residual air trapped between the cassette diaphragm 304 and the valve face gasket 318. This action is conducted for a predetermined time period, after which the door bladder pressure is regulated to its full, designated sealing pressure (e.g., about 900 mmHg). The controller 18 proceeds to the next integrity test, which is the valve cross-talk test.

C. Valve Cross-Talk Test

The objective of the valve cross-talk test is to detect leaks in the valve face gasket 318 prior to start of a saline prime of the flow set 12. The controller 16 directs the manifold assembly 34 to set the door bladder 314 to sealing pressure. Adjacent valves and pump chambers are grouped by the controller 16 into pressure and vacuum categories, e.g., as follows (refer to FIG. 25A for a schematic overview view of the arrangement of these valves):

| | |
|---|---|
| Pressure | V1; V3; V5; V7; V10; V12; V14; V16; V17; V18; V21; V24; V26; DP1; DP2; and ACP |
| Vacuum | V2; V4; V6; V8; V9; V11; V13; V15; V19; V20; V22; V23; V25; IPP; and PP |

The controller 16 directs the manifold assembly 34 to sequentially apply PHARD, PGEN to the pressure regions and to apply VHARD and VGEN to the vacuum regions. The pressure leak rate for each region at each pressure/vacuum level is determined and compared to an acceptable specified level (e.g., less than about 2 to 3 mmHg/sec). The controller generates an alarm if any region experiences a leak rate equal to or greater than the specified acceptable level, which indicates leaks in the valve face gasket 318.

If all regions experience a leak rate less than the specified acceptable level, the controller 18 proceeds to the next integrity test, which is the dry cassette integrity test.

D. Dry Cassette Integrity Test

The dry cassette integrity check detects misload conditions dealing with donor tube 126 and anticoagulant tube 152 prior to performing a saline prime of the flow set. The misload conditions can be any one or a combination of (1) the donor tube 126 and/or anticoagulant tube 152 bypassing the donor clamp 154; (2) the donor tube 126 and/or the anticoagulant tube 152 being pinched; (3) the absence of the clamp 116 or a hemostat at the donor tube 126/anticoagulant tube 152 junction. In addition to misload conditions, the test can also detect defects in the flow set, such as pin holes or broken ports in the donor tube 126, anticoagulant tube 152, or anticoagulant container 150, which may have occurred after quality assurance testing following manufacture, e.g., during shipment and handling prior to use.

The dry cassette integrity test pressurizes selected regions of the cassette 28 using air. The dry cassette integrity test uses air instead of liquid, so that proper cassette installation can be ascertained before fluid is introduced into the cassette 28. Thus, if a misload is detected, the cassette 28 can be readily reinstalled in an unused, sterile condition.

Figure 25A:
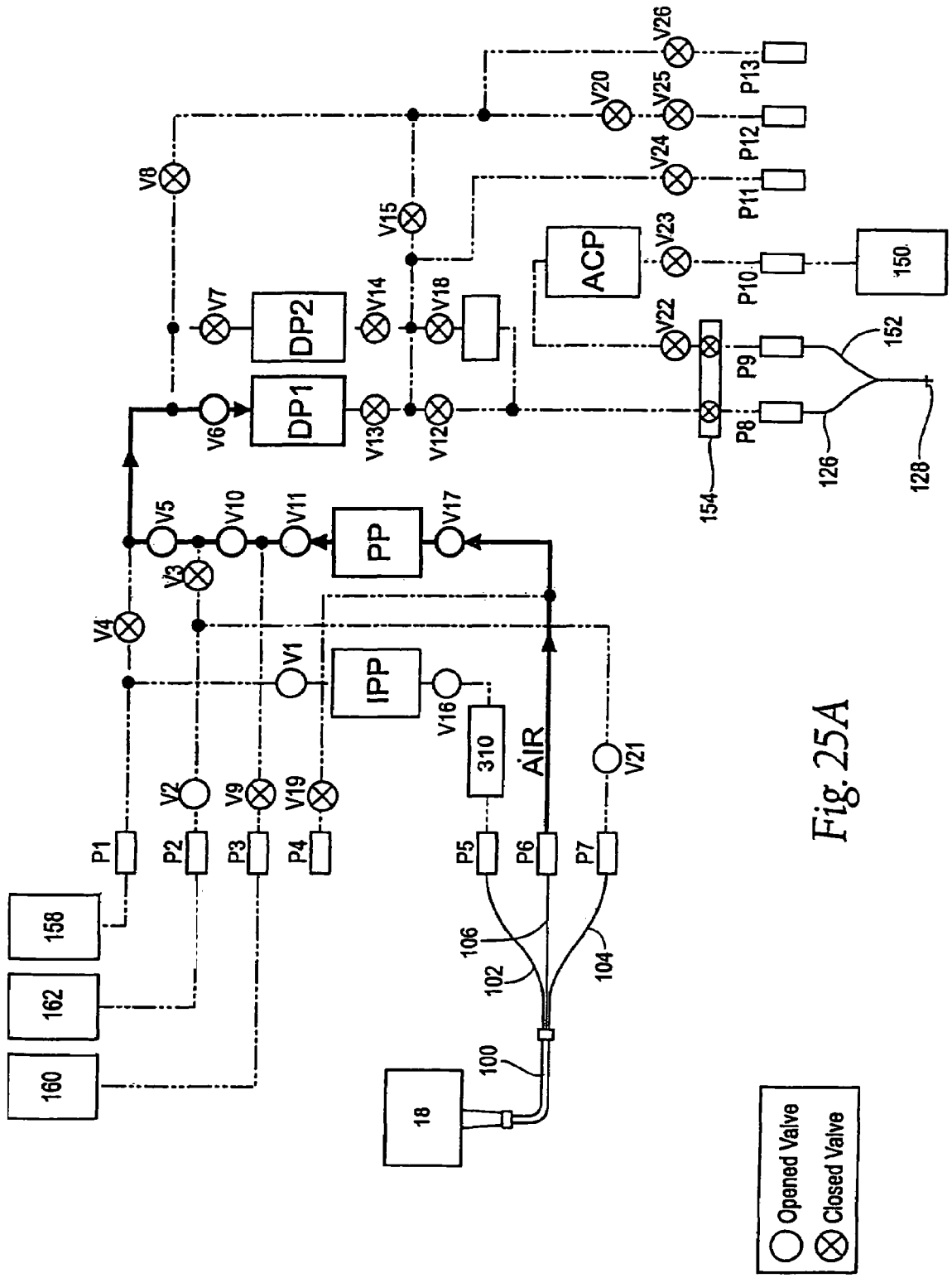
FIGS. 25A and 25B are schematic views of the fluid circuit shown in FIG. 16 being conditioned by application of positive and negative pneumatic pressures to transport air in a controlled manner that verifies that tubing intended to convey blood and liquids to and from the donor has been properly installed on the device, as shown in FIGS. 5 and 6.

During a dry cassette integrity test (as schematically depicted in FIGS. 25A/25B and 26A/26B), the controller 16 directs the manifold assembly 34 to actuate designated pump chambers in the cassette 28 to draw air from the umbilicus 100 into a selected region, and to close designated valves to hold pressure within the region. The initial pressure is sensed in a pump chamber communicating with the region. The pump chamber is coupled to the targeted tube through the donor clamp 154, which is set to a closed condition. The manifold assembly 34 is directed to apply positive pressure to the pump chamber serving the region, to try to expel air from the pump chamber. A final pressure is sensed after a specified time period. If the targeted donor tube 126 or anticoagulant tube 152 is properly loaded in the donor clamp 154, the donor clamp 154 should prevent air flow and thereby prevent a pressure drop from occurring. If a pressure drop ratio (final pressure/initial pressure) is experienced that is greater than a predetermined threshold, the donor clamp 154 is not preventing air flow, and a misload is deemed to exist.

In a representative implementation, the dry cassette integrity test comprises two phases. In the first phase, misload conditions dealing with the donor tube 126 are detected. In the second phase, misload conditions of the anticoagulant tube 152 are detected.

1. Phase 1 (Misload Condition of Donor Tube)

The condition of the fluid circuit 306 at the outset of Phase 1, is shown in FIG. 25A.

During Phase 1, the controller 16 regulates PGEN, PHARD, VGEN, and VHARD to system pressure levels. The donor clamp 154 is opened, and the entire cassette 28 is vented to the blood processing chamber 18. All cassette valves are then closed, except for the valves in a path that allows air to be drawn from the umbilicus into the donor pump chamber DP1 by operation of the plasma pump PP. In the fluid circuit 306, this path can be created, e.g., by opening V2/V21 (opening the red blood cell tube 104 from the umbilicus 100 to the red blood cell container 162); opening V1/V16 (opening the whole blood tube 102 into the umbilicus 100 to the in-process container 158 through the in-process pump PPP; and opening V5/V6/V10/V11/V17 (opening the plasma tube 106 from the umbilicus 100 to the donor pump DP1 through the plasma pump PP). The donor clamp 154 is closed, as are the other valves in the fluid circuit 306.

The controller 16 directs the manifold assembly 34 to actuate the plasma pump PP for a designated number of pump strokes. This draws air from the umbilicus 100 into donor pump DP1 (as shown by the arrow AIR path in FIG. 25A).

Figure 25B:
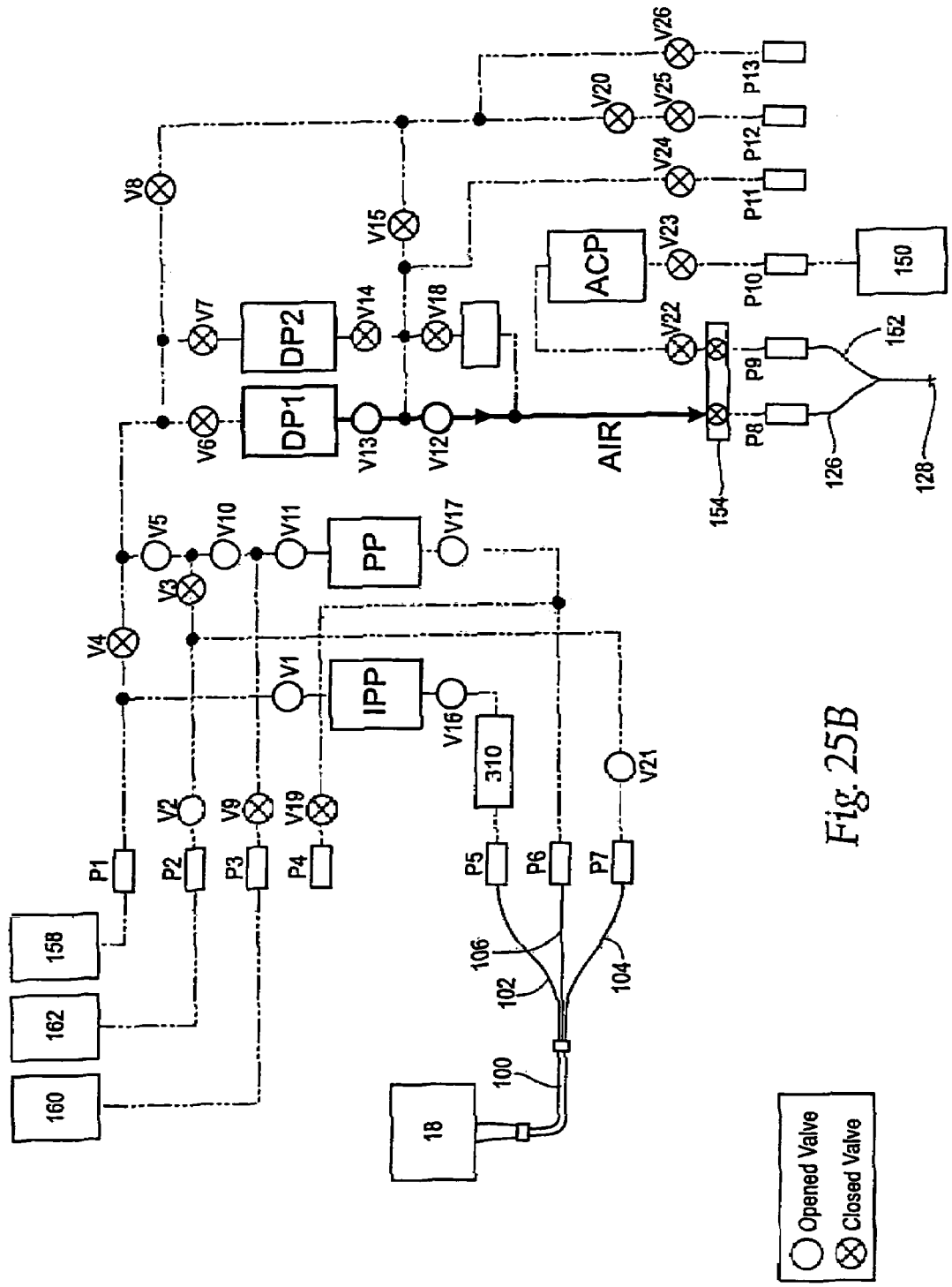

The controller 16 then directs the manifold assembly 34 to close V6, which closes the air path from the umbilicus 100. The controller then directs the manifold assembly 34 to open valves V12/V13/V18, which opens a path from the donor pump PP1 to the donor tube 126, regulated only by the donor clamp 154, which remains closed. The condition of the fluid circuit 306 at this stage of Phase 1 is shown in FIG. 25B.

The controller 16 next directs the manifold assembly 34 to hold PGEN and VHARD, vent VGEN, and, after a prescribed delay period, record the initial PGEN1 in the donor pump DP1.

The controller 16 then directs the manifold assembly 34 to apply pressure to DP1 for a prescribed period of time. This directs air from the donor pump DP1 toward the donor clamp 154, as shown by the arrow AIR path in FIG. 25B. The controller 16 records existing PGEN2.

If the ratio PGEN2/PGEN1 is less than a specified value, the controller 16 deems that leakage of air has occurred through the donor clamp 154, and that the donor tube 126 is not properly installed in the donor clamp 154. The controller 16 prompts the operator to reinstall the cassette 28. If the ratio PGEN2/PGEN1 is equal to or greater than the specified value, the controller 16 deems that leakage of air through the donor clamp 154 did not occur, and that the donor tube 126 is properly installed in the donor clamp 154. In this instance, the controller 16 moves to Phase 2 of the dry cassette integrity test.

2. Phase 2 (Misload Conditions of Anti-coagulant Tube)

Figure 26A:
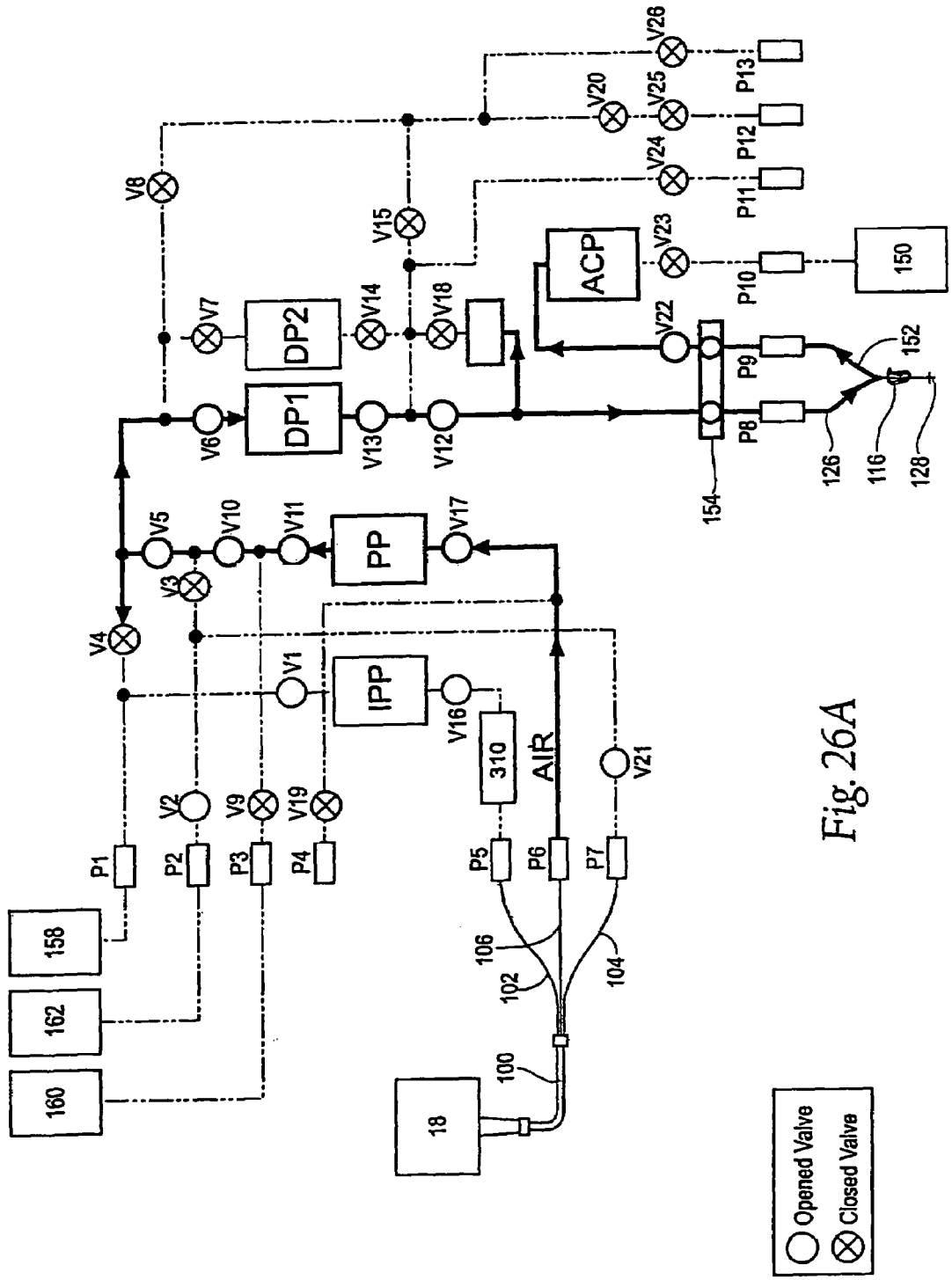
FIGS. 26A and 26B are schematic views of the fluid circuit shown in FIG. 16 being conditioned by application of positive and negative pneumatic pressures to transport air in a controlled manner that verifies that tubing intended to convey anticoagulant into blood drawn from the donor has been properly installed on the device, as shown in FIGS. 5 and 6.

The condition of the fluid circuit 306 at the outset of Phase 2 is shown in FIG. 26A.

At the outset of Phase 2, the controller regulates PGEN, PHARD, VGEN, and VHARD to system pressure levels. The donor clamp 154 is opened, and the entire cassette 28 is vented to the blood processing chamber 18. All cassette valves are closed, except for the valves that establish a path that allows air to be drawn from the umbilicus 100 into the anticoagulant pump chamber ACP through the plasma pump PP, donor pump PP1, and the donor clamp 154. In the fluid circuit 306, this path can be created, e.g., by opening V2/V21 (opening the red blood cell tube 104 from the umbilicus 100 to red blood cell container 162); opening V1/V16 (opening the whole blood tube 102 into the umbilicus 100 from in-process container 158 through the in-progress pump PPP; opening V5/V6/V10/V11/V17 (opening the plasma tube 106 from the umbilicus 100 to donor pump DP1 through the plasma pump PP); and opening V12/V13/V22 (opening the donor tube 126 from the donor pump PP1, through donor tube 126 and anticoagulant tube 152 into anticoagulant pump chamber ACP). The clamp 116 or a hemostat is also clamped closed. The controller 16 directs the manifold assembly 34 to actuate the plasma pump PP for a designated number of pump strokes. This draws air from the umbilicus 100 into anticoagulant pump ACP, through the junction of the donor tube 126 and anticoagulant tube 152 (as shown by the arrow AIR path in FIG. 26A). The controller 16 then directs the manifold assembly 34 to close V22 and the donor clamp 154, keeping the remainder of the path to the umbilicus 100 open.

Figure 26B:
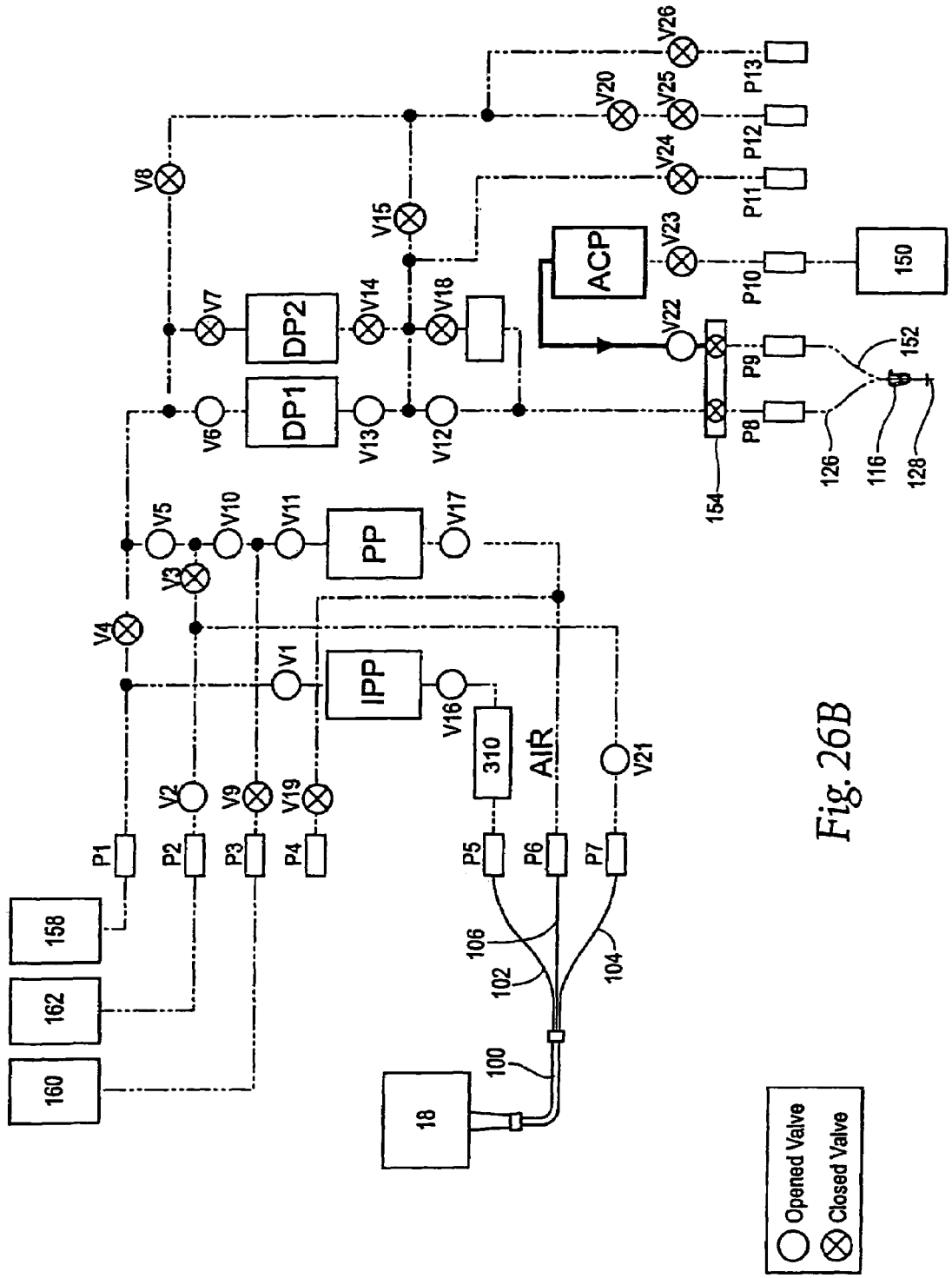

The controller 16 next directs the manifold assembly 34 to hold PGEN and VHARD, vent VGEN, and, after a prescribed delay period, record the initial PGEN1. The controller 16 then directs the manifold assembly 34 to apply pressure to ACP while opening V22 for a prescribed period of time. Air flow beyond V22 through the anticoagulant tube 152 is regulated only by the donor clamp 154, which remains closed. The controller 16 records existing PGEN2. The condition of the fluid circuit 306 at this stage of Phase 2 is shown in FIG. 26B, with the arrow AIR path from ACP to the donor clamp 154 indicated.

If the ratio PGEN2/PGEN1 is less than a specified value, the controller deems that leakage of air occurred through the donor clamp 154, and that the anticoagulant tube 152 is not properly installed in the donor clamp 154. The controller prompts the operator to reinstall the cassette 28. If the ratio PGEN2/PGEN1 is equal to or greater than the specified value, the controller deems that leakage of air through the donor clamp 154 did not occur, and that the anticoagulant tube 152 is properly installed in the donor clamp 154. In this instance, the controller moves to the final integrity check, which is the wet cassette integrity check.

E. Wet Cassette Integrity Check

The wet cassette integrity check is designed to detect defects related to product quality and donor safety that may occur in the cassette 28 itself. The check is conducted after the fluid circuit has been completely primed with a priming fluid, e.g., saline. The check uses capacitive sensing to determine the ability of the fluid circuit to maintain a pneumatic seal in selected test regions when the fluid pathways are filled with the priming fluid.

During the wet cassette integrity tests, a selected test region that includes at least one pump chamber is created. The test region is pneumatically sealed from the remainder of the fluid circuit 306 by closing valves about the boundary of the test region. During the test, the pump chamber is filled with priming fluid. The controller 16 conditions the manifold assembly 34 to attempt to empty the priming fluid from the pump chamber into the enclosed test region. Using capacitive sensing, the controller 16 assesses the volume of fluid remaining in the chamber after the emptying attempt is made. If the volume of fluid remaining in the pump chamber after the attempt is greater than a predetermined minimum volume, the controller 16 deems that the test region was pneumatically sealed sufficiently to resist leakage of fluid from the test region. If the volume of fluid remaining in the pump chamber after the attempt is equal to or less than the predetermined minimum volume, the controller 16 deems that leakage of fluid out of the test region has occurred, and a defect alarm is generated. The testing desirably creates and tests a sequence of test regions in succession.

The boundary of the various test regions can be defined by evaluating the various possible sealing failure modes that the circuit can experience.

Figure 27:
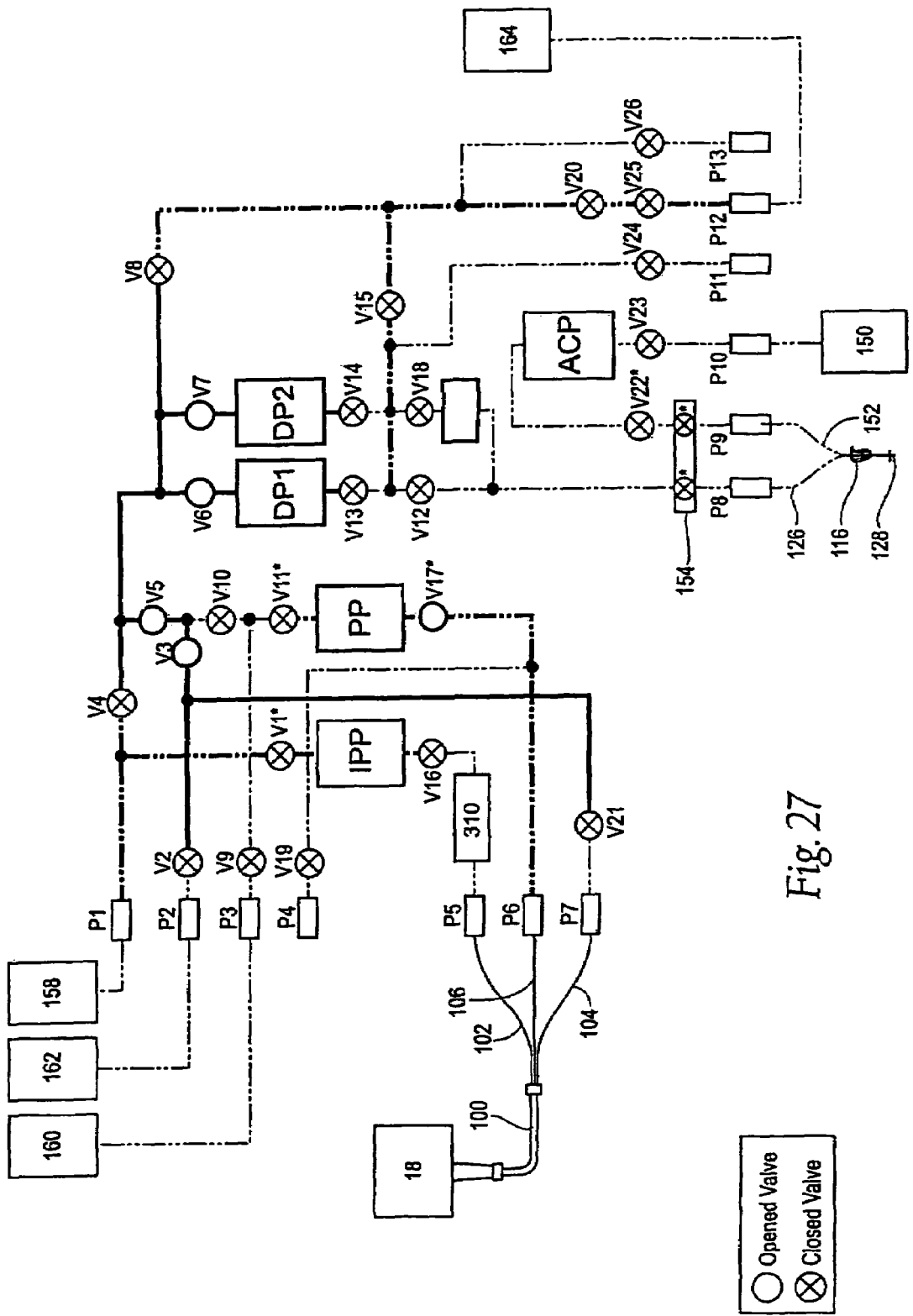
FIGS. 27 to 29 are schematic views of the fluid circuit shown in FIG. 16 being conditioned by application of positive and negative pneumatic pressures to transport a liquid in a controlled manner that verifies the physical integrity of the cassette prior to use.

In a representative implementation, the controller 16 opens the following valves to create a first targeted test region: V3; V5; V6; V7; V15; V20; V25. FIG. 27 shows the test region in bold solid lines. The test region includes the donor pump DP1 and DP2, and the test region includes a path through which blood and blood components are conveyed to and from the donor.

The controller 16 operates the donor pump DP1/DP2 and actuates the appropriate valves to draw saline from the saline container 164 into the test region, to pressurize the test region with saline to a predetermined sensed pressure. The pump chambers DP1/DP2 are filled with saline in the process.

In FIG. 27, the test region is pneumatically sealed by boundary valves V2, V4, V10, V8, V13, and V14. The controller 16 desirably opens additional valves downstream of the boundary valves to provide leak paths that fluid exiting the test region through the boundary valves can follow, thereby creating a more sensitive test of the specific boundary valves themselves. In FIG. 27, the following valves downstream of the boundary valves can be opened to provide leak paths: V1; V11; V17; V22; V23; the anticoagulant pump ACP; the plasma pump PP; the in-process pump IPP; and the donor clamp 154. The possible fluid leak paths are shown in phantom lines in FIG. 27, with the valves outside of the boundary valves that can be opened in the leak paths marked with an asterisk (*).

The controller 16 isolates the pump chambers DP1/DP2 by closing valves V6/V7/V13/V14 and, by capacitive sensing, records the pump fill volumes for each chamber. The controller 16 opens the region under test to the donor pump by opening valves V6 and V7 and close donor pump chambers DP1 and DP2 for a predetermined shortened push time to move fluid into the test region. The controller 16 then closes valves V6 and V7 and waits for a sample delay period. The controller 16 then obtains capacitance sensor readings. If the final values for either pump chamber is less than a threshold minimum value (which can, e.g., represents a baseline volume above a completely empty chamber), fluid leakage from the test region has occurred. An alarm is generated. If the final values for both pump chambers are equal to or greater than the threshold minimum, fluid leakage has not occurred, and the test proceeds.

Figure 28:
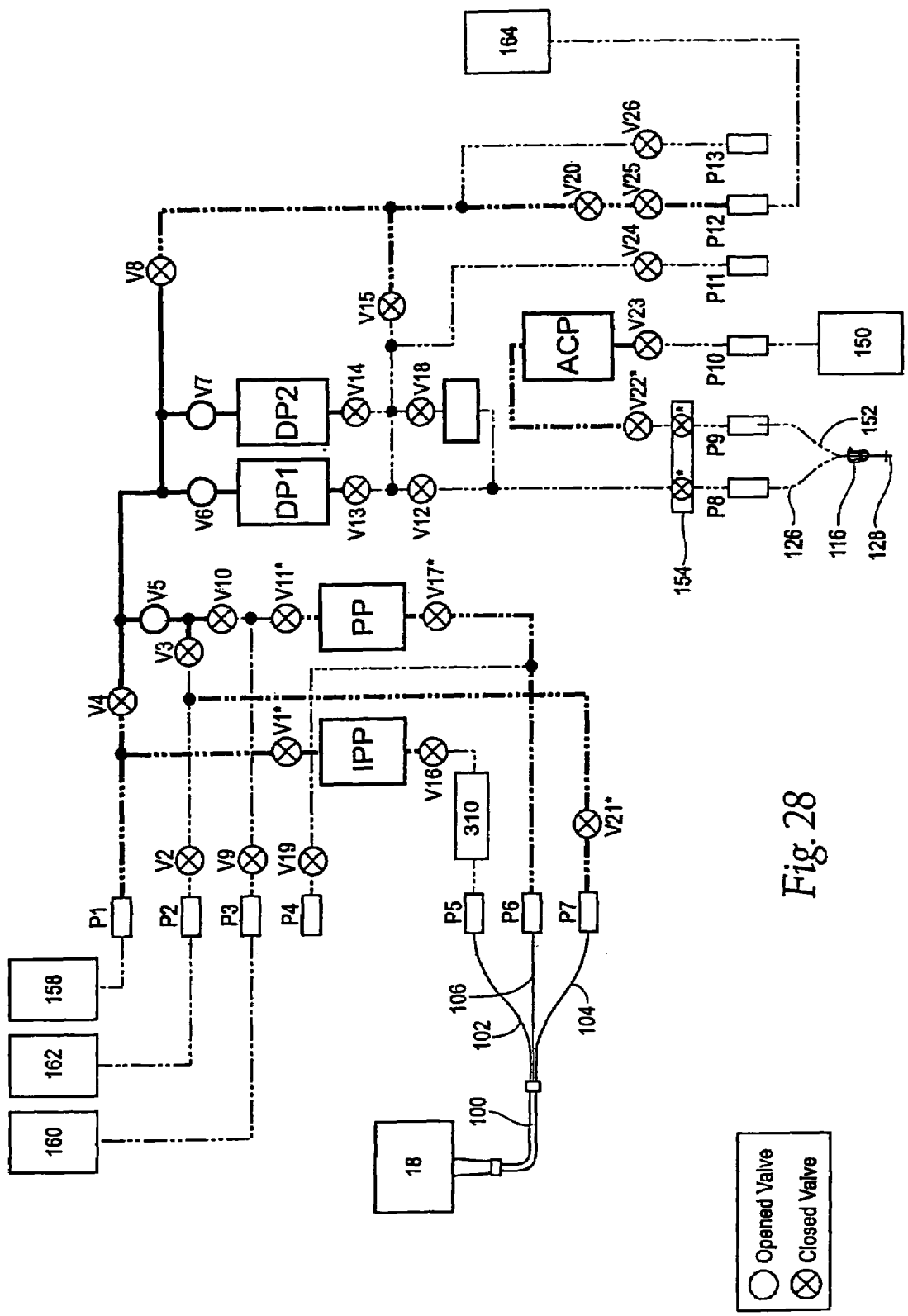

The integrity of another test region can be tested by opening the following valves: V5; V6; V7; V15; V20; V25. FIG. 28 shows this test region in bold solid lines. The controller 16 can open the following valves downstream of the boundary valves to provide fluid leak paths to create a more sensitive test: V11; V17; V21; V22; V23; the anticoagulant pump ACP; the plasma pump PP; the in-process pump IPP; and donor clamp 154. The fluid leak paths are shown in phantom lines in FIG. 28, with the valves outside of the boundary valves that can be opened in the leak paths marked with an asterisk (*).

The donor pump DP1/DP2 is actuated for a predetermined number of pump strokes to pressurize the region under test with saline from the external saline container 164. During this time, the donor pump chambers DP1 and DP2 are filled with saline from the saline container 164. The controller 16 isolates the pump chambers DP1/DP2 by closing valves V6/V7/V13/V14 and, by capacitive sensing, records the pump fill volumes for each chamber. The controller 16 opens the region under test to the donor pump DP1/DP2 by opening valves V6 and V7 and close donor pump chambers DP1 and DP2 for a predetermined shortened push time to move fluid into the test region. The controller 16 then closes valves V6 and V7 and waits for a sample delay period. The controller 16 then obtains capacitance sensor readings. If the final values for either pump chamber is less than a threshold (which represents a baseline volume above an empty chamber), fluid leakage into the test region has occurred. An alarm is generated. If the final values for both pump chambers are equal to or greater than a threshold (which represents a baseline volume above an empty chamber), fluid leakage has not occurred, and the test proceeds.

Figure 29:
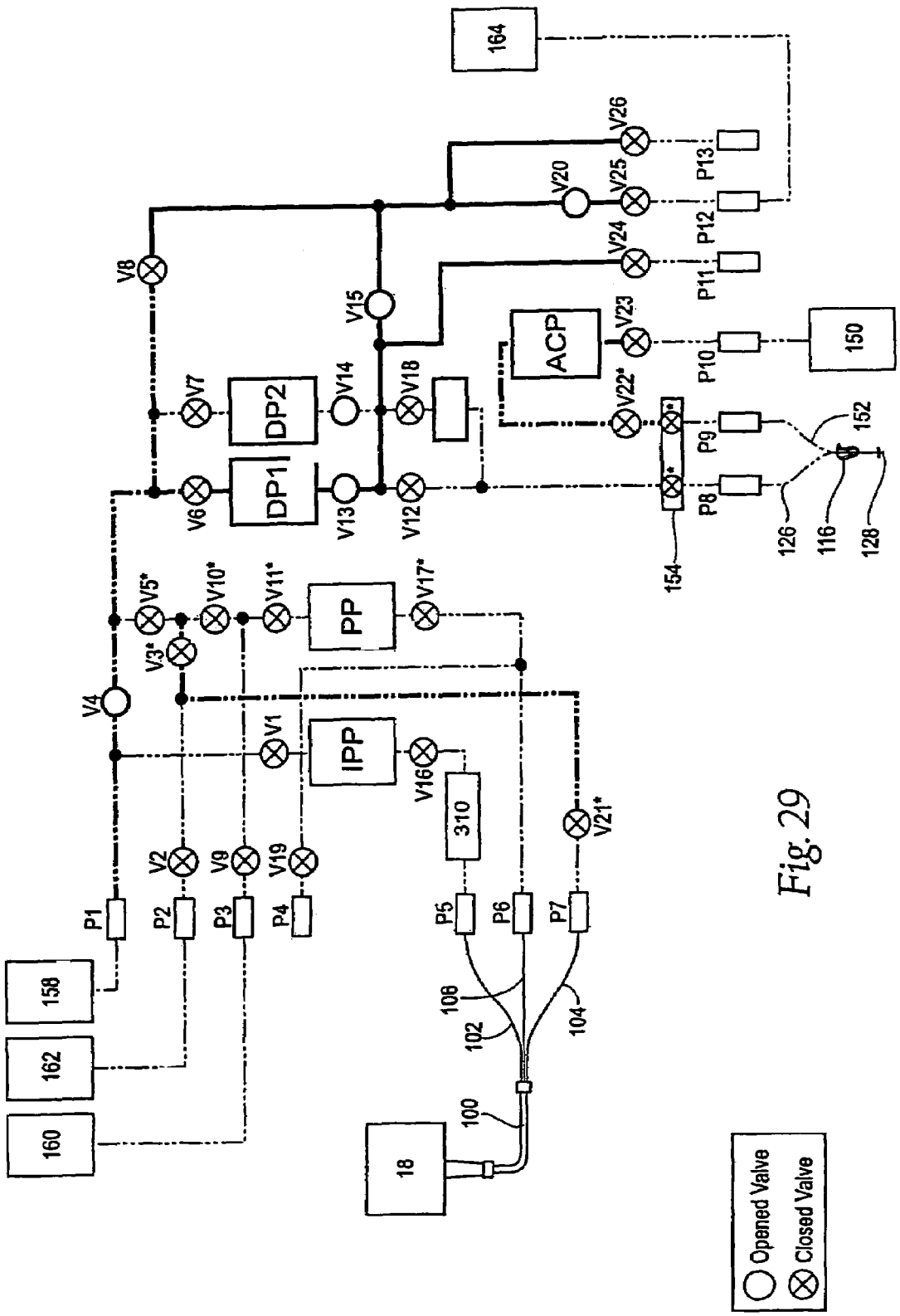

The integrity of another test region can be tested by opening the following valves, the following valves are opened to create yet another test region: V4; V13; V14; V15; and V20. FIG. 29 shows the test region in bold solid lines. As in the preceding test regions, the following valves downstream of the boundary valves can opened to create leak paths: V3; V5; V10; V11; V21; V22; V23; the anticoagulant pump ACP; the plasma pump PP; the in-process pump IPP; and the donor clamp 154. The fluid leak paths are shown in bold phantom lines in FIG. 29, with the valves outside of the boundary valves that can be opened in the leak paths marked with an asterisk (*).

The donor pump DP1/DP2 is actuated for a predetermined number of pump strokes to pressurize the region under test with saline from the in-process container 158, by passing the umbilicus 100. During this time, the donor pump chambers DP1 and DP2 are filled with saline. The controller 16 isolates the pump chambers DP1/DP2 by closing valves V6/V7/V13/V14 and, by capacitive sensing, records the pump fill volumes for each chamber. The controller 16 opens the region under test to the donor pump by opening valves V13 and V14 and close donor pump chambers DP1 and DP2 for a predetermined shortened push time to move fluid into the test region. The controller 16 then close valves V13 and V14 and waits for a sample delay period. The controller 16 then obtains capacitance sensor readings. If the final values for either pump chamber is less than a threshold (which represents a baseline volume above an empty chamber), fluid leakage into the test region has occurred. An alarm is generated. If the final values for both pump chambers are equal to or greater than a threshold (which represents a baseline volume above an empty chamber), fluid leakage has not occurred, and the three-phase test of the representative implementation is concluded.

Of course, other test regions could be established and tested according to the above-described rationale.

Following the battery of cassette integrity tests, venipuncture and blood processing using the system 10 can proceed.

VIII. CONCLUSION

The many features of the invention have been demonstrated by describing their use in separating whole blood into component parts for storage and blood component therapy. This is because the invention is well adapted for use in carrying out these blood processing procedures. It should be appreciated, however, that the features of the invention equally lend themselves to use in other processing procedures.

For example, the systems and methods described, which make use of a programmable cassette in association with a blood processing chamber, can be used for the purpose of washing or salvaging blood cells during surgery, or for the purpose of conducting therapeutic plasma exchange, or in any other procedure where blood is circulated in an extracorporeal path for treatment. Furthermore, the systems and methods described are not limited to the processing of human or animal blood drawn from vascular circulatory systems, but can also be used to process or separate suspensions created outside vascular circulatory systems and containing cellular blood components or matter recombinantly produced or collected from naturally occurring sources.

Features of the invention are set forth in the following claims.

I claim:

1. A process system comprising
a separation device that, in use, performs a separation process including separation of red blood cells from blood or a suspension containing red blood cells,
an outlet line coupled to the separation device at a selected location to allow intentional removal of substantial separated red blood cells from the separation device, at least in part, while the separation process occurs,
a sensor associated with the outlet line to sense hematocrit of red blood cells removed from the separation device and to generate a sensed hematocrit output, and
a controller including an application control manager coupled to the separation device and programmed to deliberately remove red blood cells from the separation device through the outlet line at a targeted red blood cell removal rate that is greater than zero by controlling removal of red blood cells from the separation device based, at least in part, upon the sensed hematocrit output.

2. A system according to claim 1
wherein the separation device performs the separation process by generating a centrifugal separation field.

3. A system according to claim 1
wherein the controller controls removal of red blood cells by adjusting flow rate of red blood cells in the outlet line based, at least in part, upon the sensed hematocrit output.

4. A system according to claim 1
wherein the controller compares the sensed hematocrit output to a predetermined red blood cell hematocrit value and controls removal of red blood cells based, at least in part, upon the comparison.

5. A system according to claim 1
wherein the controller monitors deviation between the sensed hematocrit output and a predetermined red blood cell hematocrit value and controls removal of red blood cells based, at least in part, upon the deviation.

6. A system according to claim 5
wherein the controller controls removal of red blood cells based, at least in part, upon magnitude of the deviation.

7. A system according to claim 5
wherein the controller controls removal of red blood cells based, at least in part, upon change of the deviation over time.

8. A system according to claim 1
wherein the sensor optically senses the hematocrit of red blood cells removed from the separation device to generate the sensed hematocrit output.

9. A processing system comprising
a separation device that, in use, performs a separation process including separation of red blood cells and plasma from blood or from a suspension containing red blood cells and plasma,
an inlet line coupled to the separation device to convey blood or the suspension into the separation device at a controlled blood flow rate Qb, at least in part, while the separation process occurs,
a plasma outlet line coupled to the separation device to convey plasma from the separation device at a controlled plasma flow rate Qp, at least in part, while the separation process occurs,
a red blood cell outlet line coupled to the separation device at a selected location to allow intentional removal of substantial separated red blood cells from the separation device at a red blood cell flow rate Qrbc, at least in part, while the separation process occurs, whereby Qrbc=Qb−Qp,
a sensor associated with the red blood cell outlet line to sense hematocrit of red blood cells removed from the separation device and to generate a sensed hematocrit output, and
a controller including an application control manager coupled to the separation device and programmed to deliberately remove red blood cells from the separation device through the red blood cell outlet line at a targeted red blood cell removal rate that is greater than zero by controlling a ratio between Qb and Qp based, at least in part, upon the sensed hematocrit output.

10. A system according to claim 9
wherein the separation device performs the separation process by generating a centrifugal separation field.

11. A system according to claim 9
wherein the controller sets Qb at a selected magnitude and varies Qp to control the ratio.

12. A system according to claim 9
wherein the controller controls the ratio based, at least in part, upon deviation between the sensed hematocrit output and a predetermined red blood cell hematocrit value.

13. A system according to claim 12
wherein the controller controls the ratio based, at least in part, upon magnitude of the deviation.

14. A system according to claim 12
wherein the controller controls the ratio based, at least in part, upon change of the deviation over time.

15. A system according to claim 9
wherein the sensor optically senses the hematocrit of red blood cells removed from the separation device to generate the sensed hematocrit output.

16. A processing method comprising the steps of performing a separation process including separation of red blood cells from blood or a suspension containing red blood cells, intentionally removing substantial separated red blood cells from the separation device at a selected location, at least in part, while the separation process occurs, sensing hematocrit of red blood cells removed from the separation device at the selected location to generate a sensed hematocrit output, and controlling removal of red blood cells from the separation device to achieve a targeted red blood cell removal rate that is greater than zero based, at least in part, upon the sensed hematocrit output.

17. A method according to claim 16 wherein the separation process includes generating a centrifugal separation field.

18. A method according to claim 16 wherein the controlling step includes adjusting the flow rate of red blood cells removed from the separation device based, at least in part, upon the sensed hematocrit output.

19. A method according to claim 16 wherein the controlling step includes comparing the sensed hematocrit output to a predetermined red blood cell hematocrit value and controlling removal of red blood cells based, at least in part, upon the comparison.

20. A method according to claim 16 wherein the controlling step includes monitoring deviation between the sensed hematocrit output and a predetermined red blood cell hematocrit value and controlling removal of red blood cells based, at least in part, upon the deviation.

21. A method according to claim 20 wherein the controlling step includes controlling removal of red blood cells based, at least in part, upon magnitude of the deviation.

22. A method according to claim 20 wherein the controlling step includes controlling removal of red blood cells based, at least in part, upon change of the deviation over time.

23. A method according to claim 16 wherein the sensing step includes optically sensing the hematocrit of red blood cells removed from the separation device to generate the sensed hematocrit output.

* * * * *